US011401554B2

(12) United States Patent
Dube et al.

(10) Patent No.: US 11,401,554 B2
(45) Date of Patent: *Aug. 2, 2022

(54) GENETIC MARKERS FOR PREDICTING RESPONSIVENESS TO THERAPY WITH HDL-RAISING OR HDL MIMICKING AGENT

(71) Applicant: Hoffmann-La Roche Inc., Little Falls, NJ (US)

(72) Inventors: Marie-Pierre Dube, Montreal (CA); Jean-Claude Tardif, Montreal (CA)

(73) Assignee: Hoffman-La Roche Inc., Little Falls, NJ (US)

( * ) Notice: Subject to any disclaimer, the term of this patent is extended or adjusted under 35 U.S.C. 154(b) by 77 days.

This patent is subject to a terminal disclaimer.

(21) Appl. No.: 16/773,040

(22) Filed: Jan. 27, 2020

(65) Prior Publication Data

US 2020/0239960 A1    Jul. 30, 2020

Related U.S. Application Data

(63) Continuation of application No. 15/415,112, filed on Jan. 25, 2017, now Pat. No. 10,584,385, which is a continuation of application No. PCT/EP2015/067098, filed on Jul. 27, 2015.

(30) Foreign Application Priority Data

Jul. 30, 2014    (EP) .................... 14179048

(51) Int. Cl.
   *C12Q 1/68*     (2018.01)
   *C12Q 1/6883*   (2018.01)
   *A61K 31/167*   (2006.01)

(52) U.S. Cl.
   CPC .......... *C12Q 1/6883* (2013.01); *A61K 31/167* (2013.01); *C12Q 2600/106* (2013.01); *C12Q 2600/118* (2013.01); *C12Q 2600/156* (2013.01)

(58) Field of Classification Search
   None
   See application file for complete search history.

(56) References Cited

U.S. PATENT DOCUMENTS

| | | |
|---|---|---|
| 6,426,365 B1 | 7/2002 | Shinkai et al. |
| 6,753,346 B2 | 6/2004 | Shinkai et al. |
| 7,271,196 B2 | 9/2007 | Shinkai et al. |
| 7,276,536 B2 | 10/2007 | Urata et al. |
| 7,375,112 B2 | 5/2008 | Friesen et al. |
| 7,435,839 B2 | 10/2008 | Martinez-Force et al. |
| 7,435,849 B2 | 10/2008 | Hoffmann et al. |
| 7,579,379 B2 | 8/2009 | Shinkai et al. |
| 7,728,171 B2 | 6/2010 | Hoffmann et al. |
| 7,858,823 B2 | 10/2010 | Hoffmann et al. |
| 7,863,474 B2 | 1/2011 | Hoffmann et al. |
| 7,956,198 B2 | 6/2011 | Sattigeri et al. |
| 7,977,509 B2 | 7/2011 | Hoffmann |
| 8,071,803 B2 | 12/2011 | Lohri |
| 8,143,442 B2 | 3/2012 | Harnett et al. |
| 8,232,281 B2 | 7/2012 | Dugi et al. |
| 8,664,403 B2 | 3/2014 | Mair et al. |
| 8,765,989 B2 | 7/2014 | Costello et al. |
| 8,975,438 B2 | 3/2015 | Birrer et al. |
| 9,000,045 B2 | 4/2015 | Shinkai et al. |
| 9,107,836 B2 | 8/2015 | Krabichler et al. |
| 9,909,178 B2 | 3/2018 | Dube et al. |
| 10,584,385 B2 | 3/2020 | Dube et al. |
| 10,711,303 B2 | 7/2020 | Dube et al. |
| 2005/0009870 A1 | 1/2005 | Sher et al. |
| 2005/0014786 A1 | 1/2005 | Sun et al. |
| 2005/0054659 A1 | 3/2005 | Ellsworth et al. |
| 2005/0080087 A1 | 4/2005 | Pendri et al. |
| 2005/0143381 A1 | 6/2005 | Yu et al. |
| 2005/0171110 A1 | 8/2005 | Yu et al. |
| 2005/0171140 A1 | 8/2005 | O'Connor et al. |
| 2005/0261201 A1 | 11/2005 | Polvino et al. |
| 2007/0213271 A1 | 9/2007 | Zavitz et al. |
| 2007/0213274 A1 | 9/2007 | Salonen |
| 2008/0221161 A1 | 9/2008 | Pinkerton et al. |
| 2008/0255084 A1 | 10/2008 | Webb |
| 2009/0035306 A1 | 2/2009 | Pinkerton et al. |
| 2009/0054304 A1 | 2/2009 | Herbert et al. |
| 2009/0105124 A1 | 4/2009 | Smith et al. |
| 2010/0183598 A1 | 7/2010 | Schultz et al. |
| 2011/0250197 A1 | 10/2011 | Sattigeri et al. |
| 2012/0093922 A1 | 4/2012 | Manku et al. |
| 2012/0121698 A1 | 5/2012 | Manku et al. |
| 2012/0148662 A1 | 6/2012 | Gross et al. |
| 2012/0213827 A1 | 8/2012 | Chatterji et al. |
| 2012/0258123 A1 | 10/2012 | Laaksonen et al. |

(Continued)

FOREIGN PATENT DOCUMENTS

| | | |
|---|---|---|
| JP | 2006288279 A | 10/2006 |
| WO | 2003/014306 A2 | 2/2003 |

(Continued)

OTHER PUBLICATIONS

International Search Report and Written Opinion for International Application No. PCT/EP2014/055790, dated Jun. 25, 2014, 12 pages.
U.S. Office Actions, dated Feb. 10, 2017 and Aug. 10, 2017, in U.S. Appl. No. 14/863,148.
U.S. Office Action, dated Dec. 20, 2019, in U.S. Appl. No. 16/109,447.
U.S. Office Action, dated Jul. 11, 2019, in U.S. Appl. No. 15/415,112.
International Search Report and Written Opinion for International Application No. PCT/EP2015/067098, dated Oct. 15, 2015.
International Search Report and Written Opinion for International Application No. PCT/EP2018/073158, dated Dec. 3, 2018.
International Search Report and Written Opinion for International Application No. PCT/EP2019/071506, dated Jan. 17, 2020.
U.S. Office Action, dated Jul. 12, 2019, in U.S. Appl. No. 16/115,135.
International Search Report and Written Opinion for International Application No. PCT/EP2020/056102, dated Jun. 26, 2020.

(Continued)

*Primary Examiner* — Jehanne S Sitton

(57) ABSTRACT

Genotyping methods and compositions for selecting patients with cardiovascular disease who will benefit from treatment with HDL-raising or HDL mimicking agent, in particular with a CETP inhibitor/modulator.

13 Claims, 10 Drawing Sheets

(56) References Cited

U.S. PATENT DOCUMENTS

| | | |
|---|---|---|
| 2012/0301439 A1 | 11/2012 | Apte |
| 2013/0195879 A1 | 8/2013 | Bylock |
| 2013/0197257 A1 | 8/2013 | Harnett et al. |
| 2013/0236468 A1 | 9/2013 | Bylock |
| 2014/0031332 A1 | 1/2014 | Laaksonen et al. |
| 2014/0121229 A1 | 5/2014 | Urata et al. |
| 2014/0171502 A1 | 6/2014 | Mair et al. |
| 2014/0364493 A1 | 12/2014 | Okamoto et al. |
| 2016/0244826 A1 | 8/2016 | Dube et al. |
| 2017/0233812 A1 | 8/2017 | Dube et al. |
| 2018/0155784 A1 | 6/2018 | Dube et al. |
| 2019/0070178 A1 | 3/2019 | Dube et al. |
| 2019/0226020 A1 | 7/2019 | Dube et al. |
| 2020/0222406 A1 | 7/2020 | Dube et al. |

FOREIGN PATENT DOCUMENTS

| | | |
|---|---|---|
| WO | 2004/067763 A2 | 8/2004 |
| WO | 2006/099142 A2 | 9/2006 |
| WO | 2010/040571 A2 | 4/2010 |
| WO | 2010/066593 A1 | 6/2010 |
| WO | 2011/008996 A2 | 1/2011 |
| WO | 2012/012870 A1 | 2/2012 |
| WO | 2012/035017 A1 | 3/2012 |
| WO | 2012/059447 A1 | 5/2012 |
| WO | 2012/076443 A1 | 6/2012 |
| WO | 2012/110469 A1 | 8/2012 |
| WO | 2012/112720 A2 | 8/2012 |
| WO | 2012136272 A1 | 10/2012 |
| WO | 2013/113799 A1 | 8/2013 |
| WO | 2013/131901 A1 | 9/2013 |
| WO | 2013/164257 A1 | 11/2013 |
| WO | 2014/027334 A2 | 2/2014 |
| WO | 2014/154606 A1 | 10/2014 |
| WO | 2015/091410 A1 | 6/2015 |
| WO | 2016/016157 A1 | 2/2016 |
| WO | 2019/043018 A1 | 3/2019 |
| WO | 2020/030814 A1 | 2/2020 |

OTHER PUBLICATIONS

Berndt, S. I, et al., "Genome-wide meta-analysis identifies 11 new loci for anthropometric traits and provides insights into genetic architecture," Nat Genet. May 2013, 45(5):501-512. doi:10.1038/ng.2606.

Bertrand, M-J. et al., "Pharmacogenomic approaches to lipid-regulating trials," Current Opinion in Lipidology, Dec. 2016, vol. 27, Issue 6, pp. 557-562.

Chen, D. et al., "Discovery of pentacyclic triterpene 3β-ester derivatives as a new class of cholesterol ester transfer protein inhibitors," European Journal of Medicinal Chemistry, 139 (2017) 201-213.

Chen, Y. et al., "Evacetrapib Reduces Preβ-1 HDL in Patients with Atherosclerotic Cardiovascular Disease or Diabetes," Atherosclerosis, Jun. 2019; 285: 147-152.

Database Embase [Online], Database Accession No. EMB-20160694852, Bertrand, M-J. et al., "Pharmacogenomic approaches to lipid-regulating trials," 2017, 2 pages.

Denisova, D. V., "A Review of Recent Scientific Advances in Atherosclerosis Research," Based on reports from the 81st EAS Congress in Lyon, Jun. 2-5, 2013, Atherosclerosis. Journal of Research and Practice, 2013, vol. 9, No. 2, pp. 63-68.

Dessauer, C. W. et al., "International Union of Basic and Clinical Pharmacology. CI. Structures and Small Molecule Modulators of Mammalian Adenylyl Cyclases," Pharmacological Reviews, vol. 69, Apr. 2017, pp. 93-139.

Dullaart, R. P. F. et al., "Type 2 diabetes mellitus is associated with differential effects on plasma cholesteryl ester transfer protein and phospholipid transfer protein activities and concentrations," Scandinavian Journal of Clinical & Laboratory Investigation, vol. 64, No. 3, pp. 205-216 (Jun. 2004).

Fayad, Z. A. et al., "Safety and efficacy of dalcetrapib on atherosclerotic disease using novel non-invasive multimodality imaging (dal-PLAQUE): a randomised clinical trial," Lancet, 378(9802):1547-1559 (Oct. 2011).

Fei, Y. et al., Abstract P5.021, "Increase in cardiovascular events in patients treated with CETP inhibitors is associated with RS1967309 SNP in ADCY9 gene," Abstracts/Atherosclerosis Supplements 32 (2018), pp. 144-145, Jan. 2018, Retrieved from the Internet: <URL:https://www.atherosclerosis-supplements.com/action/showPdf?pii=S1567-5688%2818%2930443-4>, [retrieved on Jun. 15, 2020].

Haunsø, A. et al., "Small ligands modulating the activity of mammalian adenylyl cyclases: a novel mode of inhibition by calmidazolium," Mol. Pharmacol., Mar. 2003, 63(3):624-631.

Heinig, K. et al., "Determination of dalcetrapib by liquid chromatography—tandem mass spectrometry," Journal of Pharmaceutical and Biomedical Analysis, 66:314-324 (2012).

Hopewell, J. C., "Impact of ADCY9 on Response to Anacetrapib Among 20,000 Participants in the HPS3/TIMI55-REVEAL Trial," Featured Clinical Research III, Presented at: American College of Cardiology Scientific Session, Mar. 16-18, 2019, New Orleans, 17 pages.

Holmes, M. V. et al., "CETP inhibition and ADCY9 genotype: evidence of a qualitative pharmacogenetic interaction in cardiovascular disease?", bioRxiv preprint first posted online Jun. 6, 2018, 7 pages.

Holmes, M. et al., "REVEALing the effect of CETP inhibition in cardiovascular disease," Nat. Rev. Cardiol., vol. 14, No. 11, Nov. 2017, pp. 635-636.

Inazu, A. et al., "Cholesteryl ester transfer protein and atherosclerosis," Curr. Opin. Lipidol. (2000) 11(4):389-396.

Kallend, D., "CETP, the human genome and cardiovascular outcomes," Swiss Med. Wkly, 140(21-22):294-296 (2010).

Kim, S. H. et al., "Combined pharmacogenetic effect of ADCY9 and ADRB2 gene polymorphisms on the bronchodilator response to inhaled combination therapy," J Clin Pharm Ther. (2011) 36:399-405.

Lehtinen, A. B. et al., "Genetic Mapping of Vascular Calcified Plaque Loci on Chromosome 16p in European Americans from the Diabetes Heart Study," Annals of Human Genetics 75(2):222-235 (Mar. 11, 2011).

Ludwig, M-G. et al., "Characterization of the human adenylyl cyclase gene family: cDNA gene structure, and tissue distribution of the nine isoforms," Journal of Receptors and Signal Transduction, vol. 22, Nos. 1-4, Jan. 2002, pp. 79-110.

Masson, W. et al., "Therapy with cholesteryl ester transfer protein (CETP) inhibitors and diabetes risk," Diabetes & Metabolism, vol. 44, No. 6, pp. 508-513 (Dec. 2018).

Nissen, S. E. et al., "ADCY9 Genetic Variants and Cardiovascular Outcomes With vacetrapib in Patients With High-Risk Vascular Disease a Nested Case-Control Study," JAMA Cardiol. 2018;3(5):401-408. doi:10.1001/iamacardio.2018.0569.

Rautureau, Y. et al., "ADCY9 (Adenylate Cyclase Type 9) Inactivation Protects From Atherosclerosis Only in the Absence of CETP (Cholesteryl Ester Transfer Protein)," Circulation, Oct. 16, 2018;138(16):1677-1692, originally published Apr. 19, 2018. doi: 10.1161/CIRCULATIONAHA.117.031134.

Database Embase [Online], Database Accession No. EMB-619083510, Rautureau, Y. et al., "Adenylate cyclase type 9 promotes atherosclerosis in mice," 2017, 1 page.

Rautureau, Y. et al., "Abstract 184: Adenylate Cyclase Type 9 Promotes Atherosclerosis in Mice," Poster Abstract Presentations, Session Title: Poster Session I, Originally published Aug. 25, 2017, Arteriosclerosis, Thrombosis, and Vascular Biology, 37:A184, 2 pages.

Database Embase [Online], Database Accession No. EMB-619083770, Rautureau, Y. et al., "Potentiation of endothelium-dependent vasodilation by adenylate cyclase type 9 inactivation is associated with increased endothelial cell signaling in mouse femoral arteries," 2017, 2 pages/.

Rautureau, Y. et al., "Abstract 616: Potentiation of Endothelium-Dependent Vasodilation by Adenylate Cyclase Type 9 Inactivation is Associated With Increased Endothelial Cell Signaling in Mouse Femoral Arteries," Poster Abstract Presentations, Session Title:

(56) References Cited

OTHER PUBLICATIONS

Poster Session III, Originally published Aug. 25, 2017, Arteriosclerosis, Thrombosis, and Vascular Biology, 37:A616.
Database Embase [Online], Database Accession No. EMB-619219200, Rautureau, Y. et al., "Adenylate cyclase type 9 (ADCY9) regulates vasomotor tone in mice," 2017, 1 page.
Rautureau, Y. et al., "Abstract 18757: Adenylate Cyclase Type 9 (Adcy9) Regulates Vasomotor Tone in Mice," Atherosclerosis, Vascular Biology and Development, Session Title: Endothelium, Vascular Tone and Nitric Oxide, Originally published Mar. 29, 2018, Circulation, 134:A18757, 2 pages.
Regieli, J. J. et al., "CETP genotype predicts increased mortality in statin-treated men with proven cardiovascular disease: an adverse pharmacogenetic interaction," European Heart Journal, 29(22):2792-2799 (May 30, 2008).
Schwartz, G. G. et al., "Effects of Dalcetrapib in Patients with a Recent Acute Coronary Syndrome," The New England Journal of Medicine 367(22):2089-2099 (Nov. 29, 2012).
Schwartz, G. G. et al., "Rationale and design of the dal-OUTCOMES trial: Efficacy and safety of dalcetrapib in patients with recent acute coronary syndrome," American Heart Journal, 158(6):896-901 (Dec. 1, 2009).
Seifert, R. et al., "Inhibitors of membranous adenylyl cyclases," Trends in Pharmacological Sciences, Feb. 2012, vol. 33, No. 2, pp. 64-78.
Stalenhoef, A. F. H. et al., "Efficacy and safety of dalcetrapib in type 2 diabetes mellitus and/or metabolic syndrome patients, at high cardiovascular disease risk," Diabetes, Obesity and Metabolism, vol. 14, No. 1, pp. 30-39 (2012).
Tardif, J-C et al., "CETP: Pharmacogenomics-Based Response to the CETP Inhibitor Dalcetrapib," Arterioscler. Thromb. Vasc. Biol., 37(3):396-400 (Mar. 2017). doi: 10.1161/ATVBAHA.116.307122. Epub Jan. 26, 2017.
Tardif, J-C et al., "Genotype-Dependent Effects of Dalcetrapib on Cholesterol Efflux and Inflammation. Concordance with Clinical Outcomes," Circulation: Cardiovascular Genetics, (2016) 9(4):340-348. DOI: 10.1161/CIRCGENETICS.116.001405.
Tardif, J-C et al., "Pharmacogenomic Determinants of the Cardiovascular Effects of Dalcetrapib," Circ. Cardiovasc. Genet., 8(2):372-382 (2015).
Tsygan, V. N. et al., "Pharmacokinetics of cardiovascular diseases," Vestnik of the Russian Military Medical Academy Journal, 3(19):134-142 (2007) (with English Abstract).
U.S. National Library of Medicine, National Center for Biotechnology Information, PubChem Open Chemistry Database [Online], Compound Summary for CID=6918540, Dalcetrapid, <URL: https://pubchem.ncbi.nlm.nih.gov/compound/6918540>, Create Date: Jul. 28, 2006, Retrieved from the Internet on Nov. 30, 2018, 25 pages.
Williams, S. A. et al., "Improving Assessment of Drug Safety Through Proteomics. Early Detection and Mechanistic Characterization of the Unforeseen Harmful Effects of Torcetrapib," Circulation. 2018;137:999-1010.
Wamique, M. et al., "CETP gene and its role in diabetes mellitus type II—A review," Journal of Community Medicine & Health Education, vol. 6, No. 3, 1000425 (Jan. 2016), 3 pages.
Wikipedia, "Cholesterinester-Transferprotein," Oct. 2018, Retrieved from the Internet: <URL:https://de.wikipedia.org/w/index.php? title=Cholesterinester-Transferprotein&oldid=182083305>, [retrieved on Jun. 15, 2020], 6 pages.
Schmidt et al., "Cholesteryl Ester Transfer Protein as a Drug Target for Cardiovascular Disease," medRxiv 2020.09.07.20189571; doi: https://doi.org/101101/2020.09.07.20189571.
Favad et al., "Rationale and design of dal-PLAQUE: a study assessing efficacy and safety of dalcetrapib on progression or regression of atherosclerosis using magnetic resonance imaging and 18F-fluorodeoxyglucose positron emission tomography/computed tomography," Am Heart J, Aug. 2011;162(2): pp. 214-221.
Wu et al., "Synthesis of Dalcetrapib," Chinese Journal of Pharmaceuticals, vol. 44, 2013, pp. 421-423. (The English abstract included.).

A. Cardiovascular events in the dal-OUTCOMES dalcetrapib arm

B. SNPs in the *ADCY9* region

A.

B.

GENETIC MARKERS FOR PREDICTING RESPONSIVENESS TO THERAPY WITH HDL-RAISING OR HDL MIMICKING AGENT

CROSS-REFERENCE TO RELATED APPLICATIONS

This application is a Continuation of U.S. application Ser. No. 15/415,112, filed Jan. 25, 2017, now U.S. Pat. No. 10,584,385, which is a Continuation of International Application No. PCT/EP2015/067098 filed on Jul. 27, 2015, which is entitled to the priority of EP Application No. 14179048.5 filed on Jul. 30, 2014, the disclosures of which are incorporated herein by reference.

FIELD OF THE INVENTION

The field of the invention relates to the treatment or prophylaxis of subject with cardiovascular disorder.

BACKGROUND OF THE INVENTION

Although 20 years ago, one treatment fits all was the approach taken which led to formidable "blockbuster" drugs. Today with the sequencing of the human genome and advances in molecular profiling technologies, approaches to drug development are taking a more stratified or personalized approach. These advances increasingly allow for classification of individuals into subpopulations that are at risk of a specific disease, respond to a specific treatment, don't respond to a specific treatment or are at high risk of an adverse event when treated. As such genetic tests can be used to inform diagnosis, prognosis and treatment selection. Numerous studies have shown a relationship between genotype and response to pharmaceutical therapies. This approach has been widely embraced over the past years, particularly in oncology where numerous personalized medicine approaches have been successfully developed and have provided major improvement in clinical outcomes.

In cardiovascular disorders the stratification of the population by genotype for a specific therapeutic intervention has been limited. One of the objectives of the present invention is to demonstrate that the population suffering from cardiovascular disorders might behave differently and consequently may respond differently to a specific treatment. Lowing LDL is an important therapeutic strategy in the management of cardiovascular disease. Indeed statin drugs, which lower LDL, such as Crestor, Lipitor, Pravachol, and Zocar are widely used and among the most prescribed drugs. For some time it has also been generally accepted that increasing HDL could also be therapeutic in cardiovascular disease. Several HDL-raising drugs have been developed including: niacin and CETP inhibitors such as torcetrapib, anacetrapib, evacetrapib and dalcetrapib.

Cholesterylester transfer protein (CETP) also called plasma lipid transfer protein is a hydrophobic glycoprotein that is synthesized in several tissues but mainly in the liver. CETP promotes bidirectional transfer of cholesteryl esters and triglyceride between all plasma lipoprotein particles. The first evidence of the effect of CETP activity on plasma lipoproteins was provided by observations in people with genetic deficiencies of CETP. The first CETP mutation was identified in Japan in 1989 as a cause of markedly elevated HDL-C. Ten mutations associated with CETP deficiency have since been identified in Asians and one in Caucasians. It was found in Japan that 57% of subjects with levels of HDL-C>100 mg/dL have mutations of the CETP gene. In addition, 37% of Japanese with levels HDL-C between 75-100 mg/dL have mutations of the CETP gene. Subsequently, studies of animals treated with an anti-CETP antibody showed that CETP inhibition resulted in a substantial increase in the concentration of HDL-C. Consistent with these observations in CETP deficient patients and rabbits treated with an anti-CETP antibody, it has since been found that treatment of humans with CETP inhibitor drugs increases the concentration of HDL cholesterol and apoA-I (the major apolipoprotein in HDLs). Numerous epidemiologic studies have correlated the effects of variations in CETP activity with coronary heart disease risk including studies of human mutations (Hirano, K. I. Yamishita, S. and Matsuzawa Y. (2000) Curr. Opin. Lipido. 11(4), 389-396).

Atherosclerosis and its clinical consequences, including coronary heart disease (CHD), stroke and peripheral vascular disease represents an enormous burden on health care systems internationally. Drugs that inhibit CETP (CETP inhibitors) have been under development for some time with the expectation that they will be useful for treating or preventing atherosclerosis. A number of classes of CETP inhibitor drugs have been shown to increase HDL, decrease LDL in humans and to have therapeutic effects for treating atherosclerosis and cardiovascular disease including dalcetrapib, torcetrapib, anacetrapib, evacetrapib, BAY 60-5521 and others (Table 1).

TABLE 1

Overview of Lead CETP Inhibitor Drugs and Clinical Status

| Structure | Compound | Clinical phase |
|---|---|---|
| 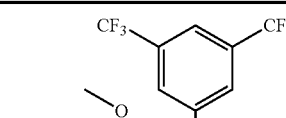 | Torcetrapib | Phase III discontinued in 2006 |

TABLE 1-continued

Overview of Lead CETP Inhibitor Drugs and Clinical Status

| Structure | Compound | Clinical phase |
|---|---|---|
| 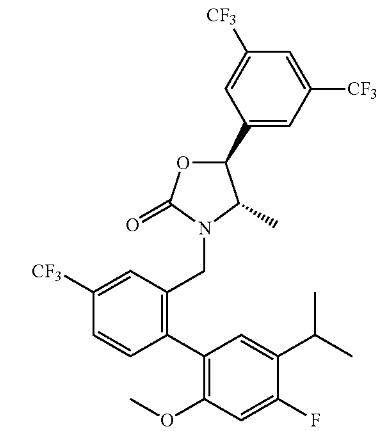 [SMILES: COc1cc(F)c(C(C)C)cc1-c1ccc(C(F)(F)F)cc1CN1C(=O)O[C@@H](c2cc(C(F)(F)F)cc(C(F)(F)F)c2)[C@@H]1C] | Anacetrapib | Phase III |
| 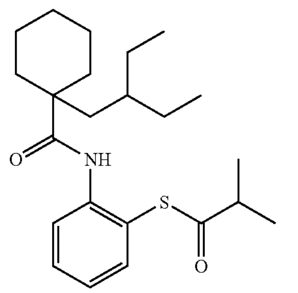 [SMILES: CCC(CC)CC1(C(=O)Nc2ccccc2SC(=O)C(C)C)CCCCC1] | Dalcetrapib | Phase III trial halted May 2012 |
| 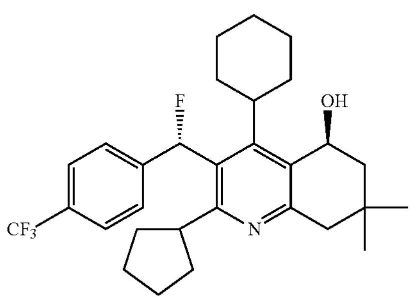 [SMILES: CC1(C)Cc2nc(C3CCCC3)c([C@@H](F)c3ccc(C(F)(F)F)cc3)c(C3CCCCC3)c2[C@@H](O)C1] | BAY 60-5521 | Phase I |

However there is evidence that these drugs may not be safe and effective in all patients. The clinical trial for torcetrapib was terminated in Phase III due to incidence of mortality in patient to whom torcetrapib and atorvastatin were administered concomitantly compared to patients treated with atorvastatin alone. The clinical trial for dalcetrapib was also halted in Phase III in this case due to a lack of efficacy relative to statins alone. Additional CETP inhibitors are still being pursued in clinical trials and earlier stage development. In general treatment strategies using CETP inhibitors that provide better efficacy, reduced off-target effects would be clinically beneficial. There is a need for biomarkers, methods and approaches for predicting response to CETP inhibitors and accessing risk of adverse events associated with administration of CETP inhibitors.

CETP inhibitors are useful for the treatment and/or prophylaxis of atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia.

Clinical trials have shown that patient response to treatment with pharmaceuticals is often heterogeneous. There a pressing need to improve drug development, clinical development and the therapeutic impact of drugs for individuals or sub-populations of patients. Single nucleotide polymorphisms (SNPs) can be used to identify patients most suited to therapy with particular pharmaceutical agents (this is often termed "pharmacogenomics"). Similarly, SNPs can be used to exclude patients from certain treatment due to the patient's increased likelihood of developing toxic side effects or their likelihood of not responding to the treatment. Pharmacogenomics can also be used in pharmaceutical research to assist the drug development and selection process. Linder et al, Clinical Chemistry 43:254 (1997); Marshall, Nature Biotechnology 15: 1249 (1997); International Patent Application WO 97/40462, Spectra Biomedical; and Schafer et al, Nature Biotechnology 16:3 (1998).

The dalcetrapib mortality and morbidity trial (dal-OUTCOMES) was a double-blind, randomized, placebo-controlled, parallel group, multi-centre study in stable CHD patients recently hospitalized for acute coronary syndrome (ACS). The study was conducted to test the hypothesis that CETP inhibition will reduce the risk of recurrent cardiovascular events in patients with recent ACS by raising levels of HDL-C through CETP inhibition. Eligible patients entered a single-blind placebo run-in period of approximately 4 to 6 weeks to allow for patients to stabilize and for completion of planned revascularization procedures. At the end of the run-in period, eligible patients in stable condition were randomized in a 1:1 ratio to 600 mg of dalcetrapib or placebo on top of evidence-based medical care for ACS. Dalcetrapib is an inhibitor of cholesterol-ester transfer protein (CETP). It has been shown to induce dose-related decreases in CETP activity and increases in HDL-C levels in several animal species and in humans. Decreasing CETP activity, through different approaches, has demonstrated anti-atherosclerotic effects in several animal models. The trial was interrupted in May 2012 by the DSMB on grounds of futility. The dal-OUTCOMES study resulted in unexpected observations related to cardiovascular disease progression. Despite a marked increase in HDL-c, patients on treatment did not show a significant reduction in cardiovascular events and the study was terminated.

Following the termination of dal-OUTCOMES study, it was hypothesized that a subgroup of the patients under study were responding differently to dalcetrapib and that dalcetrapib could be having a significant therapeutic effect in a sub-population of patients. A pharmacogenomic study of the dal-OUTCOMES study population was conducted to study the inter-individual variation in dalcetrapib response and to identify genetic markers for predicting therapeutic response to dalcetrapib, or other CETP inhibitors, for patient stratification and for treatment selection.

SUMMARY OF THE INVENTION

The present invention provides genotyping methods, reagents and compositions for selecting individuals who can benefit from treatment with HDL-raising or HDL mimicking agent, in particular with a CETP inhibitor/modulator, in particular wherein the individuals have cardiovascular disorder. The invention also provides methods of treating patients with a cardiovascular disorder comprising genotyping and selection of patients who may benefit from treatment with HDL-raising or HDL mimicking agent, in particular with a CETP inhibitor/modulator. Surprisingly the pharmacogenomic study of the dal-OUTCOMES patient cohort found single nucleotide polymorphisms (SNPs), genetic markers, associated with an individual's response to dalcetrapib and useful for predicting therapeutic response to HDL-raising or HDL mimicking agent (in particular a CETP inhibitor/modulator) and in treating patients with HDL-raising or HDL mimicking agent (in particular CETP inhibitor/modulator).

The invention further provides methods for treating or preventing a cardiovascular disorder, comprising administering to a subject in need thereof an amount of an HDL-raising or HDL mimicking agent that is effective to treat or prevent the cardiovascular disorder, wherein the subject has a polymorphism at rs11647778 in the subject's ADCY9 gene. In some embodiments, the subject has a genotype of CC at rs11647778. In certain embodiments, the HDL-raising or HDL mimicking agent is niacin, fibrates, glitazone, dalcetrapib, anacetrapib, evacetrapib, DEZ-001, ATH-03, DRL-17822 (Dr. Reddy's), DLBS-1449, RVX-208, CSL-112, CER-001 or ApoA1-Milnano.

Genetic markers detected in the genotyping methods of the invention include: 20 SNPs that occur in the Adenylate Cyclase Type 9 (ADCY9) gene on chromosome 16, rs11647778 and optionally rs1967309, rs12595857, rs2239310, rs11647828, rs8049452, rs12935810, rs74702385, rs17136707, rs8061182, rs111590482, rs4786454, rs2283497, rs2531967, rs3730119, rs2531971, rs2238448, rs12599911, rs12920508, or rs13337675, in particular rs11647778 or rs1967309, which are both in strong linkage disequilibrium together ($r^2$=0.79) and strongly associated with response to an HDL-raising or HDL mimicking agent, in particular a CETP inhibitor/modulator.

Other gene markers of the invention include a SNP in the ADCY9 gene that are either in linkage disequilibrium with rs11647778 or rs1967309 or provided an association signal with clinical events with a statistical P<0.05 and may provide useful surrogate biomarkers of rs11647778 or rs1967309. In one embodiment a surrogate biomarker, consisting of a SNP inherited in linkage disequilibrium with rs11647778 or rs1967309, are detected and the genotype of rs11647778 or rs1967309 are inferred.

The present invention relates to methods of genotyping patients and/or treating patients with HDL-raising drug, in particular a CETP inhibitor. In particular embodiments, the methods comprise assessing the genotype of a patient at rs11647778. Three genotypes at rs11647778 are predictive of an individual's response to an HDL-raising drug, in particular a CETP inhibitor: CC, CG and GG. Of these the CC genotype is associated with an improved therapeutic response in patients treated with an HDL-raising drug, the CG genotype is associated with a partial response and the GG genotype is associated with a lack of response (non-response). For the purpose of the present invention: patients who carry the CC genotype can benefit from treatment with an HDL-raising drug; patients who carry the CG genotype can benefit from treatment with an HDL-raising drug and patients who carry the GG genotype cannot benefit from treatment with an HDL-raising drug. Two genotypes at rs11647778, CC and CG indicate a therapeutic response to a CETP inhibitor, in particular dalcetrapib, in patients with cardiovascular disorder. In particular, CC genotype for rs11647778 is indicative of greater therapeutic response to a CETP inhibitor, in particular dalcetrapib, in patients with cardiovascular disorder.

The present invention relates to nucleic acid molecules containing polymorphisms or gene variants, variant proteins encoded by these nucleic acid molecules, reagents for detecting the polymorphic nucleic acid molecules, and methods of using the nucleic acid molecules and proteins as well as methods of using reagents for their detection (e.g., primers and probes for use in the genotyping methods of the invention).

In one embodiment the invention provides: methods of detecting the gene variants of the invention and detection reagents, such as probes or primers, for use in these methods.

The invention specifically provides, genetic markers associated with therapeutic response to a HDL-raising or HDL mimicking agent, in particular a CETP inhibitor/modulator, and synthetic nucleic acid molecules (including DNA and RNA molecules) containing the gene variants of the invention. The invention further provides variant proteins encoded by nucleic acid molecules containing such gene variants, antibodies to the encoded variant proteins, computer-based and data storage systems containing the novel gene variant or SNP information, methods of detecting these SNPs in a test sample, methods of identifying individuals who respond therapeutically when administered a HDL-raising or HDL mimicking agent, in particular a CETP inhibitor/modulator, based on the presence or absence of one or more of the gene variants of the invention or the detection of one or more encoded variant products (e.g., variant mRNA transcripts or variant proteins), and methods of treating individuals who have a cardiovascular disease who carry one of more of the gene variants of the invention.

Exemplary embodiments of the present invention further provide methods for selecting or formulating a treatment regimen (e.g., methods for determining whether or not to administer HDL-raising or HDL mimicking agent, in particular CETP inhibitor/modulator treatment to an individual).

Various embodiments of the present invention also provide methods for selecting individuals to whom a HDL-raising or HDL mimicking agent (in particular CETP inhibitor/modulator) can be therapeutically administered based on the individual's genotype, and methods for selecting individuals for participation in a clinical trial of a HDL-raising or HDL mimicking agent (in particular a CETP inhibitor/modulator) based on the genotypes of the individuals (e.g., selecting individuals to participate in the trial who are most likely to respond positively and/or excluding individuals from the trial who are unlikely to respond positively to treatment based on their genotype(s), in particular their genotype is CC at rs11647778, TT at rs2238448, and/or AA at rs1967309, or selecting individuals who are unlikely to respond positively for participation in a clinical trial of alternative drug that may benefit them.

The nucleic acid molecules of the invention can be inserted in an expression vector, to produce a variant protein in a host cell. Thus, the present invention also provides for a vector comprising a SNP-containing nucleic acid molecule of the invention, genetically-engineered host cells containing the vector, and methods for expressing a recombinant variant protein using such host cells. In another specific embodiment, the host cells, SNP-containing nucleic acid molecules, and/or variant proteins can be used as targets in a method for screening or identifying therapeutic agents that are HDL-raising or HDL mimicking agent (in particular CETP inhibitor/modulator).

Exemplary SNPs of ADCY9 that can be determined/evaluated in the herein provided method for identification of an improved response to dalcetrapib or for treating or preventing a cardiovascular disease in a patient are those where the mutation results in a change in the nucleotide sequence at position 4,062,592, 4,065, 583, 4,059,439 and 4,051,380, (genome assembly GRCh37.p5) also known as single nucleotide polymorphisms with identifiers rs12595857, rs1967309, rs2238448, and rs11647778, respectively, as shown in SEQ. ID. NO. 2 1, 19 and 21.

The present invention is based on the identification of genetic polymorphisms that are predictive of an increased likelihood that treatment with a HDL-raising or HDL mimicking agent, in particular CETP inhibitor/modulator may benefit patients with cardiovascular disorders.

DETAILED DESCRIPTION OF THE INVENTION

Figure 1:
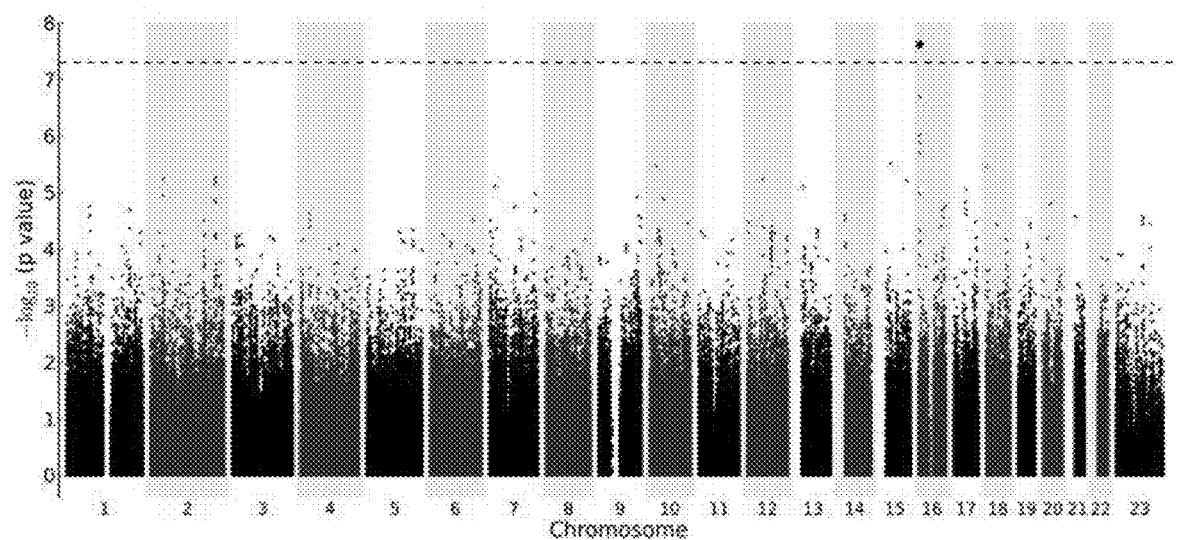
FIG. 1: SNP rs1967309 is strongly associated with a reduction of cardiovascular events (coronary heart disease death, resuscitated cardiac arrest, non-fatal myocardial infarction, non-fatal ischemic stroke, unstable angina or unanticipated coronary revascularization) in patients treated with the CETP inhibitor dalcetrapib. The figures show the results of the genome-wide association study of patients from the dalcetrapib arm of the dal-OUTCOMES trial. A shows results in a Manhattan plot with a strong signal in the ADCY9 gene region on chromosome 16. Each dot represents a P value for association of SNPs with minor allele frequencies >0.05 tested with Cox proportional hazards model for the occurrence of cardiovascular events during treatment and adjusted for sex and 5 principal components for genetic ancestry. B shows results for single-nucleotide polymorphisms in the ADCY9 region along with 6 imputed SNPs with P<10'. The x axis shows the genomic location of the ADCY9 gene on chromosome 16. The left y axis shows the negative $\log_{10}$ of P values for the comparison between cardiovascular events versus no events weighted for imputation probability in a logistic regression model framework. The right y axis shows the recombination rate. The degree of linkage disequilibrium is presented on a grayscale gradient according to $r^2$ as estimated from the reference CEU samples from HapMap.
Figure 1:
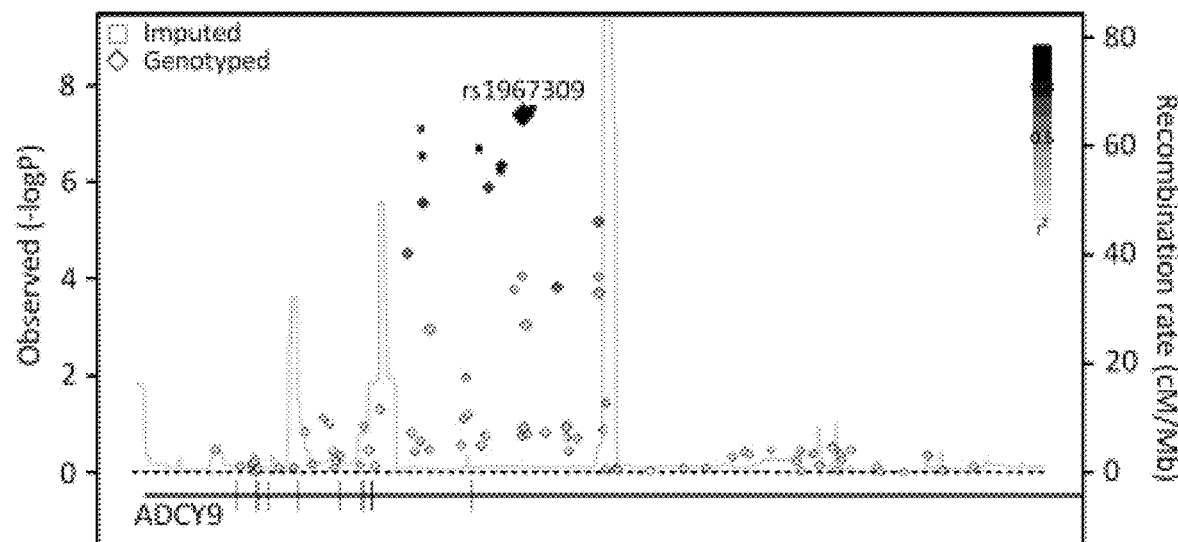
Figure 2:
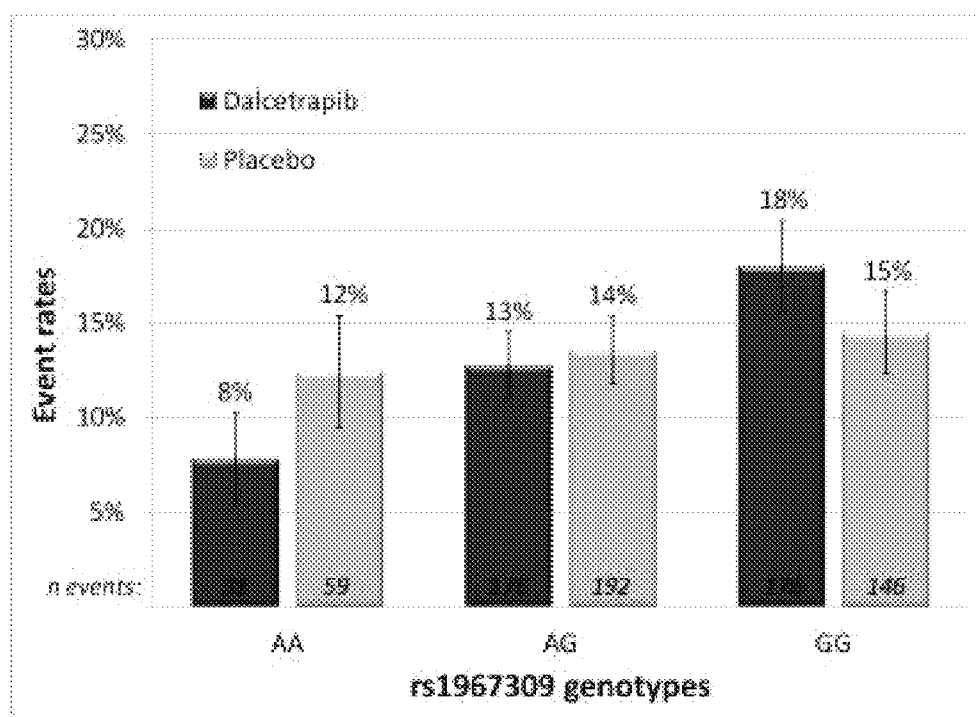
FIG. 2: Frequency of cardiovascular events (dal-OUTCOMES primary composite event or unanticipated coronary revascularization) by study termination in the dalcetrapib and placebo treatment arms separately and by rs1967309 genotypes in the ADCY9 gene. Percentages of events are reported with 95% CI.

Various features and embodiments of the present invention are disclosed herein, however other features of the invention, modifications and equivalents will be apparent to a person skilled in the relevant art, based on the teachings provided. The invention described is not limited to the examples and embodiments provided, various alternatives equivalents will be appreciate by those skilled in the art. As used herein, the singular forms "a", "an" and "the" include the plural unless the context clearly dictates otherwise. For example, "a" cell will also include "cells".

The term "about" when used in connection with a referenced numeric indication means the referenced numeric indication plus or minus up to 10% of that referenced numeric indication. For example, "about 100" means from 90 to 110.

An "allele" is defined as any one or more alternative forms of a given gene. In a diploid cell or organism the members of an allelic pair (i.e. the two alleles of a given gene) occupy corresponding positions (loci) on a pair of homologous chromosomes and if these alleles are genetically identical the cell or organism is said to be "homozygous", but if genetically different the cell or organism is said to be "heterozygous" with respect to the particular gene.

A "gene" is an ordered sequence of nucleotides located in a particular position on a particular chromosome that encodes a specific functional product and may include untranslated and untranscribed sequences in proximity to the coding regions. Such non-coding sequences may contain regulatory sequences needed for transcription and translation of the sequence or introns etc. or may as yet to have any function attributed to them beyond the occurrence of the SNP of interest.

"genotyping" refers to the determination of the genetic information an individual carries at one or more positions in the genome. For example, genotyping may comprise the determination of which allele or alleles an individual carries for a single SNP or the determination of which allele or alleles an individual carries for a plurality of SNPs. For example, at rs1967309 the nucleotides may be a A in some individuals and a G in other individuals. Those individuals who have a A at the position have the A allele and those who have a G have the G allele. In a diploid organism the individual will have two copies of the sequence containing the polymorphic position so the individual may have a A allele and a G allele or alternatively, two copies of the A alleles or two copies of the G allele. Those individuals who have two copies of the G allele are homozygous for the G allele, those individuals who have two copies of the A allele are homozygous for the A allele, and those individuals who have one copy of each allele are heterozygous. The alleles are often referred to as the A allele, often the major allele, and the B allele, often the minor allele. The genotypes may be AA (homozygous A), BB (homozygous B) or AB (heterozygous). Genotyping methods generally provide for identification of the sample as AA, BB or AB.

The term "comprising" is intended to mean that the compositions and methods include the recited elements, but do not exclude others.

"HDL-raising or HDL mimicking agent" refers to compounds which increase HDL levels by either one of the following mechanisms: CETP inhibition/modulation, PPAR agonism, LXR agonism, HM74 agonism (niacin receptor) thyrotropin hormone receptor agonism, Inhibitors of lipases and HDL catabolism ApoA1 inducers, compounds which provide at least one of the HDL athero-protective activities such as compounds that would increase cellular lipid efflux (cholesterol and/or phospholipids), have antioxidant and anti-inflammatory activities. In particular HDL mimicking agent is ApoA1 and ApoA1 derivatives (such as apoA1 Milano, ApoA1 Paris) and other analogues, reconstituted HDL containing ApoA1 and or ApoAII and the appropriate lipids such as phospholipids. ApoE, derivatives, analogues, and peptidomimetics of amphipathic lipoproteins. Examples of "HDL-raising or HDL mimicking agent" are niacin, fibrates, glitazone, dalcetrapib, anacetrapib, evacetrapib, DEZ-001 (formerly known as TA-8995)(Mitsubishi Tanabe Pharma), ATH-03 (Affris), DRL-17822 (Dr. Reddy's), DLBS-1449 (Dexa Medica), RVX-208 (Resverlogix), CSL-112 (C1s Behring), CER-001 (Cerenis), ApoA1-Milnano (Medicine Company). Particular examples of "HDL-raising or HDL mimicking agent" are niacin, fibrates, glitazone, dalcetrapib, anacetrapib, evacetrapib, torcetrapib preferably niacin, fibrates, glitazone, dalcetrapib, anacetrapib or evacetrapib. More particularly HDL-raising or mimicking agent is selected from a CETP inhibitor/modulator. Examples of CETP inhibitor/modulators are dalcetrapib, anacetrapib, evacetrapib, DEZ-001 (formerly known as TA-8995)(Mitsubishi Tanabe Pharma), ATH-03 (Affris), DRL-17822 (Dr. Reddy's), DLBS-1449 (Dexa Medica). More particularly examples of CETP inhibitor/modulators are dalcetrapib, anacetrapib, evacetrapib and torcetrapib, preferably dalcetrapib, anacetrapib and evacetrapib. Most particularly the HDL-raising or mimicking agent according to the invention would refer to a CETP inhibitor/modulator, especially when the CETP inhibitor/modulator is dalcetrapib.

"CETP inhibitor/modulator" refers to a compound which decreases CETP activity (assessed by standard transfer assays) by inhibiting CETP and/or inducing conformational changes of the CETP polypeptide once bound to the CETP polypeptide. The CETP conformational changes of the CETP polypeptide allow CETP activity to proceed between HDL particles and increase its recycling/turnover bay increasing the production of nascent pre-beta HDL formation. Preferably the CETP inhibitor/modulator refers to all compounds that would bind to cysteine 13 of the CETP polypeptide. More preferably, the "CETP inhibitor/modulator" is selected from S-[2-[1-(2-ethylbutyl)cyclohexylcarbonylamino]-phenyl] 2-methylthiopropionate, 1-(2-Ethylbutyl)-cyclohexanecarboxylic acid (2-mercapto-phenyl)-amide and or bis [2-[1-(2-ethylbutyl) cyclohexylcarbonylamino]phenyl] disulfide. Most preferably, "CETP inhibitor/modulator" is S-[2-[1-(2-ethylbutyl)cyclohexylcarbonylamino]-phenyl]2-methylthiopropionate as a prodrug or 1-(2-Ethyl-butyl)-cyclohexanecarboxylic acid (2-mercapto-phenyl)-amide as its active metabolite.

"Anacetrapib" refers to ((4S,5R)-5-[3,5-bis(trifluoromethyl)phenyl]-3-{[4'-fluoro-2'-methoxy-5'-(propan-2-yl)-4-(trifluoromethyl) [1,1'-biphenyl]-2-yl]methyl}-4-methyl-I,3-oxazolidin-2-one) also known as MK 0859, CAS 875446-37-0 or a compound of formula ($X_A$).

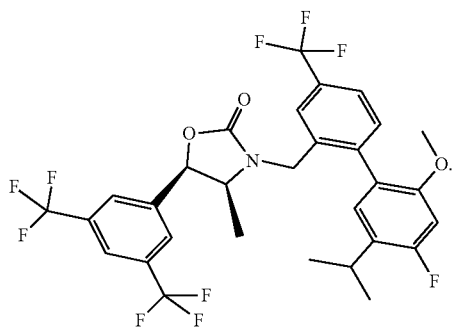

(X$_A$)

Anacetrapib as well as methods of making and using the compound, are described in WO2006/014413, WO2006/014357, WO2007005572.

"Evacatrapib" refers Trans-4-({(5S)-5-[{[3,5-bis(trifluoromethyl)phenyl]methyl}(2-methyl-2H-tetrazol-5-yl) amino]-7,9-dimethyl-2,3,4,5-tetrahydro-1H-benzazepin-1-yl}methyl) cyclohexanecarboxylic acid also known as LY2484595, CAS1186486-62-3 or a compound of formula ($X_B$)

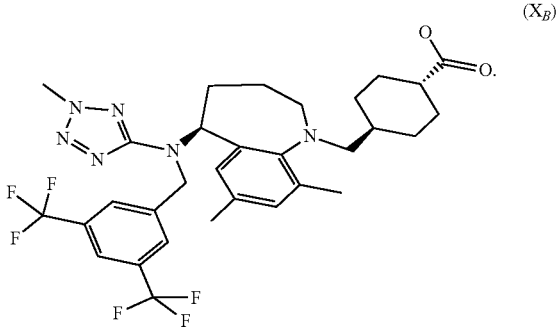

(X$_B$)

Evacetrapib as well as methods of making and using the compound are described in WO2011002696.

"Torcetrapib" refers to (2R,4S)-4-[(3,5-bistrifluoromethylbenzyl)methoxycarbonylamino]-2-ethyl-6-trifluoromethyl-3,4-dihydro-2H-quinoline-1-carboxylic acid ethyl ester, also known as CP-529,414, CAS 262352-17-0 or a compound of formula ($X_C$)

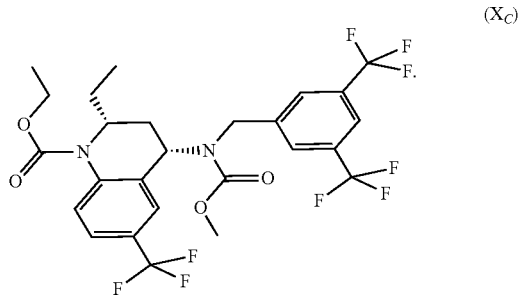

(X$_C$)

Torcetrapib as well as methods of making and using the compound are described in WO0017164 or WO0140190.

"BAY 60-5521" refers to (5S)-5-Quinolinol, 4-cyclohexyl-2-cyclopentyl-3-[(S)-fluoro[4-(trifluoromethyl)phenyl]methyl]-5,6,7,8-tetrahydro-7,7-dimethyl-, also known as CAS 893409-49-9 or a compound of formula (XD)

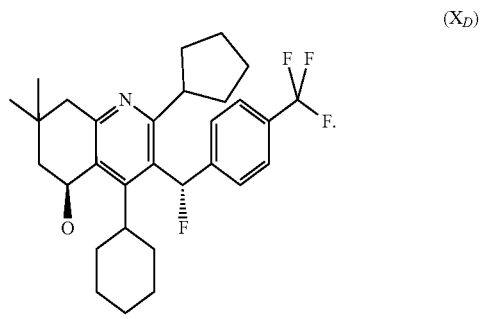

(X$_D$)

BAY 60-5521 as well as methods of making and using the compound are described in WO2006063828.

"Treatment" refers to both therapeutic treatment and prophylactic or preventative measures. Those in need of treatment include those already with the disorder as well as those in which the disorder is to be prevented or delayed.

The term "polymorphism" "polymorphism site" Polymorphic site" or "single nucleotide polymorphism site" (SNP site) or "single nucleotide polymorphism" refers to a location in the sequence of a gene which varies within a population. A polymorphism is the occurrence of two or more forms of a gene or position within a gene "allele", in a population, in such frequencies that the presence of the rarest of the forms cannot be explained by mutation alone. Preferred polymorphic sites have at least two alleles. The implication is that polymorphic alleles confer some phenotype variability on the host. Polymorphism may occur in both the coding regions and the noncoding region of genes. Polymorphism may occur at a single nucleotides site or may involve an insertion or a deletion. The location of such a polymorphism may be identified by its nucleotide position in the gene, on the chromosome or on the transcriptor by the amino acids that is altered by the nucleotide polymorphism. Individual polymorphisms are also assigned unique identifiers ("Reference SNP", "refSNP" or "rs #") known to one of skill in the art and used, e.g., in the Single Nucleotide Polymorphism Database (dbSNP) of Nucleotide Sequence Variation available on the NCBI website.

The terms "linkage disequilibrium" or "in linkage disequilibrium" or "LD" refers to the non-random association of alleles in a collection of individuals, in other words it is the preferential segregation of a particular polymorphic form with another polymorphic form at a different chromosomal location more frequently than expected by chance. By opposition the alleles that co-occur at expected frequencies are said to be in 'linkage equilibrium".

The "rs" prefix refers to a SNP in the database found at the NCB1 SNP database http://www.ncbi.nlm.nih.gov/snp/?term. The "rs" numbers are the NCBI rsSNP ID form.

The term "sample" includes any biological sample taken from a patient or individual including a cell, tissue sample or body fluid. For example, a sample may include a skin sample, a cheek cell sample, saliva or blood cells. A sample can include, without limitation, a single cell, multiple cells, fragments of cells, an aliquot of a body fluid, whole blood, platelets, serum, plasma, red blood cells, white blood cells, endothelial cells, tissue biopsies, synovial fluid and lymphatic fluid. In particular "sample" refers to blood cells.

The term "therapeutic agents" refers to agents capable of treating or preventing cardiovascular disorder. As used herein, an agent "capable of treating or preventing cardiovascular disorder" refers to a molecule that is capable of treating and/or preventing a cardiovascular disorder in humans and/or in a cellular or animal model of said cardiovascular disorder.

An "improved response polymorphism", "improved response genotype" or "responsive genotype" as used herein refers to an allelic variant or genotype at one or more polymorphic sites within the ADCY9 gene as described herein (for example, rs11647778/CC), which predicts that a subject will respond therapeutically and benefit from treatment with an HDL-raising or HDL mimicking agent (which may be measured by a decreased number of cardiovascular events) as compared to an allelic variant or genotype or polymorphism (for example, rs11647778/CG or rs11647778/GG) which predicts that a subject will respond less to HDL-raising or HDL mimicking agent administration. "Reduced response" "partial response", "non response" or "lack of therapeutic efficacy", may be measured by a relative increase in number of cardiovascular events relative to subjects having an "improved response genotype". Alternately, "improved response", "responder" or "therapeutic efficacy" may be measured by a relative decrease in number of cardiovascular events relative to subjects that carry polymorphisms associated with "non response" or "partial response" to a HDL-raising or HDL mimicking agent. In particular rs11647778/CC, and optionally rs12595857/GG, rs1967309/AA, rs111590482/AG, rs111590482/GG, rs11647828/GG, rs12935810/GG, rs17136707/GG, rs2239310/GG, rs2283497/AA, rs2531967/AA, rs3730119/AA, rs4786454/AA, rs74702385/GA, rs74702385/AA, rs8049452/GG, rs8061182/AA and rs2238448/TT are improved response genotypes. More particularly, rs11647778/CC and optionally rs1967309/AA, and rs2238448/TT is and improved response genotype. Most particularly, rs11647778/CC and rs1967309/AA is improved response genotype.

"Cardiovascular events" as used herein refers to cardiovascular death, non-fatal myocardial infarction (MI), non-fatal stroke of ischemic origin, hospitalization for unstable angina and coronary revascularization.

"Oligonucleotides" as used herein are variable length nucleic acids or polynucleotides. Such oligonucleotides may be useful as probes, primers and in the manufacture of microarrays (arrays) for the detection and/or amplification of specific nucleic acids. Such DNA or RNA strands may be synthesized by the sequential addition (5'-3' or 3 '-5') of activated monomers to a growing chain, which may be linked to an insoluble support. Numerous methods are known in the art for synthesizing oligonucleotides for subsequent individual use or as a part of the insoluble support, for example in arrays (BERNFIELD M R. and ROTTMAN F M. J. Biol. Chem. (1967) 242(18):4134-43; SULSTON J. et al. PNAS (1968) 60(2):409-415; GILLAM S. et al. Nucleic Acid Res. (1975) 2(5):613-624; BONORA G M. et al. Nucleic Acid Res. (1990) 18(11):3155-9; LASHKARI D A. et al. PNAS (1995) 92(17):7912-5; MCGALL G. et al. PNAS (1996) 93(24): 13555-60; ALBERT T J. et al. Nucleic Acid Res. (2003) 31(7):e35; GAO X. et al. Biopolymers (2004) 73(5):579-96; and MOORCROFT M J. et al. Nucleic Acid Res. (2005) 33(8):e75). In general, oligonucleotides are synthesized through the stepwise addition of activated and protected monomers under a variety of conditions depending on the method being used. Subsequently, specific protecting groups may be removed to allow for further elongation and subsequently and once synthesis is complete all the protecting groups may be removed and the oligonucleotides removed from their solid supports for purification of the complete chains if so desired.

The term "genotype" refers to the genetic constitution of an organism, usually in respect to one gene or a few genes or a region of a gene relevant to a particular context (i.e. the genetic loci responsible for a particular phenotype). In particular, the specific combination of alleles at a given position in a gene, such as for example, the genotypes AA, AG, or GG which are possible genotypes of the rs1967309 SNP.

A "phenotype" is defined as the observable characters of an organism. Tables 2, 3, 4 and 5 show a genotype correlation for ADCY9 SNP with values representing an indication of responsiveness to treatment of cardiovascular disorders with a HDL-raising or HDL mimicking agent.

The term "biomarker" as used herein refers to a sequence characteristic of a particular variant allele (polymorphic site, such as a SNP) or wild-type allele. Biomarker also refers to a peptide or epitope encoded by a particular variant or wild-type allele.

The term "surrogate marker" as used herein refers to a genetic variant, including a SNP, that is present in linkage disequilibrium with an improved response genotype of the invention, in particular rs11647778/CC.

The term "genetic marker" as used herein refers to variants of polymorphic sites of a particular gene that are associated with response to a HDL-raising or HDL mimicking agent, in particular CETP inhibitor/modulator. In particular 'genetic marker' as used herein refers to variants of polymorphic sites in the ADCY9 gene that are associated with response to a HDL-raising or HDL mimicking agent, in particular a CETP inhibitor/modulator.

Three genotypes at rs11647778 are predictive of an individual's response to an HDL-raising drug, in particular a CETP inhibitor: CC, CG and GG. Of these, the CC genotype is associated with an improved therapeutic response in patients to an HDL-raising drug, the CG genotype is associated with a partial response, and the GG genotype is associated with a lack of response (non-response). For the purpose of the present invention: patients who carry the CC genotype can benefit from treatment with an HDL-raising drug; patients who carry the CG genotype can benefit from treatment with an HDL-raising drug, and patients who carry the GG genotype cannot benefit from treatment with an HDL-raising drug. The CC and CG genotypes at rs11647778 in patients with a cardiovascular disorder indicate a therapeutic response to a CETP inhibitor, in particular dalcetrapib. In particular, the CC genotype at rs11647778 in patients with a cardiovascular disorder is indicative of a greater therapeutic response to a CETP inhibitor, in particular dalcetrapib.

Three genotypes at rs2238448 are predictive of an individual's response to an HDL-raising drug, in particular a CETP inhibitor: TT, TC and CC. Of these three genotypes, the TT genotype is associated with an improved therapeutic response in patients treated with an HDL-raising drug, whereas the CC genotype is associated with a lack of response (non-response). Patients who carry the TC genotype can benefit from treatment with an HDL-raising drug as this genotype is associated with a partial response. For the purpose of the present invention: patients who carry the TT or CT genotype can benefit from treatment with an HDL-raising drug and patients who carry the CC genotype cannot benefit from treatment with an HDL-raising drug. The TT genotype at rs2238448 in patients with a cardiovascular disorder indicates a greater therapeutic response to a CETP inhibitor, in particular dalcetrapib, as compared to other genotypes.

In certain methods described herein one or more biomarkers are used to identify or select individuals who will benefit from treatment with a HDL-raising or HDL mimicking agent, in particular a CETP inhibitor/modulator. A SNP biomarker for use in the invention can be predictive of either a therapeutic response (R) to treatment or non-response to treatment (NR). Table 2 shows genotypes observed in the dal-Outcomes cohort, present at the polymorphic site rs1967309, which can be used as a biomarker to predict response to dalcetrapib or HDL-raising or HDL mimicking agent, in particular to other CETP inhibitor/modulator. Table 4 shows genotypes observed in the dal-Outcomes and dal-Plaque-2 cohorts, present at the polymorphic site rs11647778, which can be used as a biomarker to predict response to dalcetrapib or HDL-raising or HDL mimicking agent, in particular to other CETP inhibitor/modulator. Each genotype shown in Table 2, to 5 alone or in combination with genotypes at other polymorphic sites can be used as a biomarker for predicting response to a HDL-raising or HDL mimicking agent, in particular to a CETP inhibitor/modulator).

TABLE 2 genetic markers and predicted response to treatment with HDL-raising or HDL mimicking agent

| SNP | Genotype | Responsiveness to treatment |
|---|---|---|
| rs1967309 | AA | R |
| rs1967309 | AG | PR |
| rs1967309 | GG | NR |

R: Responsive
PR: Partial Responsive
NR: Non Responsive

TABLE 3 genetic markers and predicted response to treatment with HDL-raising or HDL mimicking agent

| SNP | Genotype | Responsiveness to treatment |
|---|---|---|
| rs12595857 | AA | NR |
| rs12595857 | AG | PR |
| rs12595857 | GG | R |

R: Responsive
PR: Partial Responsive
NR: Non Responsive

TABLE 4 genetic markers and predicted response to treatment with HDL-raising or HDL mimicking agent

| SNP | Genotype | Responsiveness to treatment |
|---|---|---|
| rs11647778 | GG | NR |
| rs11647778 | CG | PR |
| rs11647778 | CC | R |

R: Responsive
PR: Partial Responsive
NR: Non Responsive

TABLE 5 genetic markers and predicted response to treatment with HDL-raising or HDL mimicking agent

| SNP | Genotype | Responsiveness to Treatment |
|---|---|---|
| rs2238448 | TT | R |
| | TC | PR |
| | CC | NR |
| rs111590482 | AA | NR |
| | AG | R |
| | GG | R |
| rs11647828 | AA | NR |
| | AG | PR |
| | GG | R |
| rs12935810 | GG | R |
| | GA | NR |
| | AA | NR |
| rs13337675 | AA | NR |
| | AG | PR |
| | GG | PR |
| rs17136707 | AA | NR |
| | AG | PR |
| | GG | R |
| rs2239310 | AA | NR |
| | AG | PR |
| | GG | R |
| rs2283497 | CC | NR |
| | CA | PR |
| | AA | R |
| rs2531967 | GG | NR |
| | GA | PR |
| | AA | R |
| rs3730119 | GG | NR |
| | GA | PR |
| | AA | R |
| rs4786454 | GG | NR |
| | GA | PR |
| | AA | R |
| rs74702385 | GG | NR |
| | GA | R |
| | AA | R |
| rs8049452 | GG | R |
| | GA | PR |
| | AA | NR |
| rs8061182 | AA | R |
| | AG | PR |
| | GG | NR |

R: Responsive
PR: Partial Responsive
NR: Non Responsive

Rs11647778, rs1967309 and rs12595857 are located in an intronic (non-coding) region of the ADCY9 gene in a region that is concordant with having regulatory activity on the ADCY9 gene expression.

In certain methods described herein individuals who will respond therapeutically to treatment with a HDL-raising or HDL mimicking agent, in particular with a CETP inhibitor/modulator are identified and selected for treatment using the genotyping methods of the invention. In particular patients who carry rs11647778/CC and optionally one or more of the following improved response genotypes, are selected for treatment in the methods of the invention: rs12595857/GG, rs1967309/AA, rs111590482/AG, rs111590482/GG, rs11647828/GG, rs12935810/GG, rs17136707/GG, rs2239310/GG, rs2283497/AA, rs2531967/AA, rs3730119/ AA, rs4786454/AA, rs74702385/GA, rs74702385/AA, rs8049452/GG, rs8061182/AA, rs2238448/TT. More particularly, patients who carry rs11647778/CC and optionally rs12595857/GG, rs2238448/TT and/or rs1967309/AA genotypes are selected for treatment in the methods of the invention: Most particularly, patients who carry rs11647778/ CC and rs1967309/AA genotypes are selected for treatment in the methods of the invention.

In another embodiment the invention provides, a method for identifying a subject benefiting from a HDL-raising or HDL mimicking agent, the method comprising determining a genotype of said subject (e.g., genotyping) at one or more of polymorphic sites in the ADCY9 gene.

In another embodiment the invention provides, a method for determining an individual's responsiveness to a HDL-raising or HDL mimicking agent, in particular a CETP inhibitor, the method comprising determining a genotype of said subject (e.g., genotyping) at rs11647778 and optionally at one or more of rs1967309, rs12595857, rs2239310, rs11647828, rs8049452, rs12935810, rs74702385, rs17136707, rs8061182, rs111590482, rs4786454, rs2283497, rs2531967, rs3730119, rs13337675, rs12920508, rs12599911, rs2531971 or rs2238448, using one or more of the primers or probes disclosed herein.

In another embodiment the invention provides, a method for determining an individual's responsiveness to a HDL-raising or HDL mimicking agent, in particular a CETP inhibitor, the method comprising determining a genotype of said subject (e.g., genotyping) at rs11647778 and optionally at one or more of rs1967309, rs12595857, rs2239310, rs11647828, rs8049452, rs12935810, rs74702385, rs17136707, rs8061182, rs111590482, rs4786454, rs2283497, rs2531967 or rs3730119, rs13337675, using one or more of the primers or probes disclosed herein.

In a particular embodiment, the invention provides the method herein described wherein the polymorphic sites comprise rs11647778 and optionally one or more of the following sites selected from the group consisting of: rs1967309, rs12595857, rs2239310, rs11647828, rs8049452, rs12935810, rs74702385, rs17136707, rs8061182, rs111590482, rs4786454, rs2283497, rs2531967, rs3730119, rs13337675, rs12920508, rs12599911, rs2531971 or rs2238448, particularly wherein the polymorphic site is selected from the group consisting of rs2239310, rs11647828, rs8049452, rs12935810, rs74702385, rs17136707, rs8061182, rs111590482, rs4786454, rs2283497, rs2531967, rs3730119 and rs13337675, more particularly wherein the polymorphic site is rs11647778 and optionally rs1967309 or rs12595857, more particularly wherein the polymorphic site is rs11647778 and optionally rs1967309, in particular wherein the corresponding genotypes comprises CC and AA respectively.

In a particular embodiment, the invention provides methods of genotyping one or more polymorphic sites, wherein at least one polymorphic site is rs11647778 and optionally one or more polymorphic sites selected from the group consisting of: rs1967309, rs12595857, rs2239310, rs11647828, rs8049452, rs12935810, rs74702385, rs17136707, rs8061182, rs111590482, rs4786454, rs2283497, rs2531967, rs3730119, rs13337675, rs12920508, rs12599911, rs2531971 or rs2238448, particularly wherein the optionally polymorphic site is elected from the group consisting of rs2239310, rs11647828, rs8049452, rs12935810, rs74702385, rs17136707, rs8061182, rs111590482, rs4786454, rs2283497, rs2531967, rs3730119 and rs13337675 more particularly wherein the optional polymorphic site is rs1967309 or, rs12595857, more particularly wherein the optional polymorphic site is rs1967309.

In a particular embodiment, the invention provides a method wherein a subject carrying rs11647778/CC and optionally one or more of rs12595857/GG, rs1967309/AA, rs111590482/AG, rs111590482/GG, rs11647828/GG, rs12935810/GG, rs17136707/GG, rs2239310/GG, rs2283497/AA, rs2531967/AA, rs3730119/AA, rs4786454/ AA, rs74702385/GA, rs74702385/AA, rs8049452/GG, rs8061182/AA, or rs2238448/TT benefits from treatment with an HDL-raising or HDL mimicking agent, particularly wherein the HDL-raising or HDL mimicking agent is a CETP inhibitor/modulator, and more particularly wherein the HDL-raising or HDL mimicking agent is S-(2-{[1-(2-ethyl-butyl)-cyclohexanecarbonyl]-amino}-phenyl) ester. In a particular embodiment, the invention provides the method wherein a HDL-raising or HDL mimicking agent is administered to said subject.

In a particular embodiment, the invention provides a method wherein a subject carrying rs11647778/CC and optionally one or more of rs12595857/GG, rs1967309/AA, rs111590482/AG, rs111590482/GG, rs11647828/GG, rs12935810/GG, rs17136707/GG, rs2239310/GG, rs2283497/AA, rs2531967/AA, rs3730119/AA, rs4786454/ AA, rs74702385/GA, rs74702385/AA, rs8049452/GG, rs8061182/AA, or rs2238448/TT is treated with an HDL-raising or HDL mimicking agent, particularly wherein the HDL-raising or HDL mimicking agent is a CETP inhibitor/modulator, and more particularly wherein the HDL-raising or HDL mimicking agent is S-(2-{[1-(2-ethyl-butyl)-cyclohexanecarbonyl]-amino}-phenyl) ester.

In a particular embodiment, the invention provides a method wherein a subject carrying rs11647778/CC and optionally one or more of rs12595857/GG, rs1967309/AA, rs111590482/AG, rs111590482/GG, rs11647828/GG, rs12935810/GG, rs17136707/GG, rs2239310/GG, rs2283497/AA, rs2531967/AA, rs3730119/AA, rs4786454/ AA, rs74702385/GA, rs74702385/AA, rs8049452/GG, rs8061182/AA, or rs2238448/TT is administered with an HDL-raising or HDL mimicking agent, particularly wherein the HDL-raising or HDL mimicking agent is a CETP inhibitor/modulator, and more particularly wherein the HDL-raising or HDL mimicking agent is S-(2-{[1-(2-ethylbutyl)-cyclohexanecarbonyl]-amino}-phenyl) ester.

In particular embodiments, the invention provides a method wherein the subject, has a cardiovascular disorder, in particular wherein the cardiovascular disorder is selected from the group consisting of atherosclerosis, peripheral vascular disease, dyslipidemia, hyperbetalipoproteinemia, hypoalphalipoproteinemia, hypercholesterolemia, hypertriglyceridemia, familial-hypercholesterolemia, angina, ischemia, cardiac ischemia, stroke, myocardial infarction, reperfusion injury, angioplastic restenosis, hypertension, and vascular complications of diabetes, obesity or endotoxemia in a mammal, more particularly wherein the cardiovascular disorder is selected from the group consisting of cardiovascular disease, coronary heart disease, coronary artery disease, hypoalphalipoproteinemia, hyperbetalipoproteinemia, hypercholesterolemia, hyperlipidemia, atherosclerosis, hypertension, hypertriglyceridemia, hyperlipidoproteinemia, peripheral vascular disease, angina, ischemia, and myocardial infarction.

In another embodiment the invention provides a method of treating or preventing a cardiovascular disorder in a subject in need thereof, the method comprising:
(a) selecting a subject having an improved response genotype at rs11647778 and optionally at one or more of the following sites: rs1967309, rs12595857, rs2239310, rs11647828, rs8049452, rs12935810, rs74702385, rs17136707, rs8061182, rs111590482, rs4786454, rs2283497, rs2531967, rs3730119, rs13337675, rs12920508, rs12599911, rs2531971 or rs2238448;
(b) administering to said subject a HDL-raising or HDL mimicking agent, in particular a CETP inhibitor/modulator.

In another embodiment the invention provides a method of treating or preventing a cardiovascular disorder in a subject in need thereof, the method comprising:
(a) selecting a subject having an improved response genotype at rs11647778 and optionally one or more of the following sites: rs1967309, rs12595857, rs2239310, rs11647828, rs8049452, rs12935810, rs74702385, rs17136707, rs8061182, rs111590482, rs4786454, rs2283497, rs2531967, rs3730119, rs13337675;
(b) administering to said subject a HDL-raising or HDL mimicking agent, in particular a CETP inhibitor/modulator.

In a particular embodiment the invention provides a method of treating a cardiovascular disorder in a subject in need thereof, the method comprising:
(a) selecting a subject having an improved response polymorphism at rs11647778 and optionally rs1967309 and/or rs2238448, in particular wherein the subject has CC genotype at rs11647778 AA genotype at rs1967309 and TT genotype at rs2238448;
(b) administering to said subject a HDL-raising or HDL mimicking agent, in particular a CETP inhibitor/modulator.

In a particular embodiment the invention provides a method of treating or preventing a cardiovascular disorder in a subject in need thereof, the method comprising:
(a) selecting a subject having an improved response polymorphism at rs11647778 and optionally rs1967309, in particular wherein the subject has CC genotype at rs11647778 and AA genotype at rs1967309;
(b) administering to said subject a HDL-raising or HDL mimicking agent, in particular a CETP inhibitor/modulator.

In another embodiment the invention provides a method of treating or preventing a cardiovascular disorder in a subject in need thereof, the method comprising:
(a) genotyping a subject at rs11647778 and optionally at one or more of the following sites: rs1967309, rs12595857, rs2239310, rs11647828, rs8049452, rs12935810, rs74702385, rs17136707, rs8061182, rs111590482, rs4786454, rs2283497, rs2531967, rs3730119, rs13337675, rs12920508, rs12599911, rs2531971 or rs2238448;
(b) administering to said subject a HDL-raising or HDL mimicking agent, in particular a CETP inhibitor/modulator.

In another embodiment the invention provides a method of treating or preventing a cardiovascular disorder in a subject in need thereof, the method comprising:
(a) genotyping a subject at rs11647778 and optionally one or more of the following sites: rs1967309, rs12595857, rs2239310, rs11647828, rs8049452, rs12935810, rs74702385, rs17136707, rs8061182, rs111590482, rs4786454, rs2283497, rs2531967, rs3730119, rs13337675;
(b) administering to said subject a HDL-raising or HDL mimicking agent, in particular a CETP inhibitor/modulator.

The invention also provides a method of treating or preventing a patient comprising:
a. analyzing a patient sample for the presence of genetic marker rs11647778/CC and optionally one or more genetic markers selected from the group consisting of rs12595857/GG, rs1967309/AA, rs111590482/AG, rs111590482/GG, rs11647828/GG, rs12935810/GG, rs17136707/GG, rs2239310/GG, rs2283497/AA, rs2531967/AA, rs3730119/AA, rs4786454/AA, rs74702385/GA, rs74702385/AA, rs8049452/GG and rs8061182/AA and
b. administering to a patient who carries one or more of said genetic markers with a HDL-raising or HDL mimicking agent, in particular a CETP inhibitor/modulator.

The invention also provides a method of treating a patient comprising:
a. analyzing a patient sample for the presence of genetic marker rs11647778/CC and optionally one or more genetic markers selected from the group consisting of rs12595857/GG, rs1967309/AA, rs111590482/AG, rs111590482/GG, rs11647828/GG, rs12935810/GG, rs17136707/GG, rs2239310/GG, rs2283497/AA, rs2531967/AA, rs3730119/AA, rs4786454/AA, rs74702385/GA, rs74702385/AA, rs8049452/GG and rs8061182/AA and
b. treating a patient who carries one or more of said genetic markers with a HDL-raising or HDL mimicking agent, in particular a CETP inhibitor/modulator.

In a particular embodiment, the invention provides the method wherein a genotype is determined at rs11647778 and optionally one or more sites selected from: rs1967309 and rs12595857.

In a particular embodiment, the present invention provides a method of determining individuals responsiveness to a HDL-raising drug comprising:
a. obtaining a sample from the individual, wherein the sample comprising genetic material;
b. contacting the sample with a reagent, such as probes or primers, generating a complex between the reagent and a genetic marker selected from Table 10;
c. detecting the complex to obtain a dataset associated with the sample and
d. analyzing the dataset to determine the presence or absence of a genetic marker.

In a particular embodiment, the present invention provides a method of determining responsiveness to an HDL-raising drug in a patient having one or more symptoms of a cardiovascular disease comprising:
a. obtaining a sample from the patient, wherein the sample comprises genetic material;
b. contacting the genetic material with a reagent, such as a probe or primer set to generate a complex between the reagent and a genetic marker selected from Table 10;

c. detecting the complex to obtain a dataset associated with the sample;
d. analyzing the dataset to determine the presence or absence of a genetic marker; and
e. identifying a patient who has one or more genetic markers as a candidate to receive an HDL-raising drug.

The complex between the reagent (such as probes or primers) and a genetic marker generated in the genotyping methods provided can be generated by either polymerase chain reaction (PCR) or DNA sequencing. Such methods are described herein and are well known to those of skill in the art.

The invention provides reagents (such as probes or primers) for genotyping a genetic marker selected from rs11647778/CC, rs12595857/GG; rs1967309/AA; rs111590482/AG; rs111590482/GG; rs11647828/GG; rs12935810/GG; rs17136707/GG; rs2239310/GG; rs2283497/AA; rs2531967/AA; rs3730119/AA; rs4786454/AA; rs74702385/GA; rs74702385/AA; rs8049452/GG; rs11647778/CG, rs8061182/AA; rs1967309/GA, rs12595857/AG, rs13337675/AG, rs13337675/GG, rs17136707/AG, rs2239310/AG, rs2283497/CA, rs2531967/GA, rs3730119/GA, rs4786454/GA, rs8049452/GA, rs8061182/AG, rs12595857/GG, rs1967309/AA, rs111590482/AG, rs111590482/GG, rs11647828/GG, rs12935810/GG, rs17136707/GG, rs2239310/GG, rs2283497/AA, rs2531967/AA, rs3730119/AA, rs4786454/AA, rs74702385/GA, rs74702385/AA, rs8049452/GG, rs8061182/AA, rs12935810/GA, rs12935810/AA, rs11647828/AA, rs2531967/GG, rs3730119/GG, rs2239310/AA, rs12595857/AA, rs111590482/AA, rs74702385/GG, rs11647778/GG, rs1967309/GG, rs2283497/CC, rs8061182/GG, rs17136707/AA, rs2238448/TT, rs2238448/TC, rs2238448/CC, rs8049452/AA, rs4786454/GG, rs13337675/AA and rs11647828/AG, preferably rs11647778, in particular a primer or a probe.

In a particular embodiment, the primer comprises strand of DNA that is 15 to 30 nucleotides in length and hybridizes under high stringency conditions to a region of chromosome 16 adjacent to rs11647778, rs1967309, rs12595857, rs2239310, rs11647828, rs8049452, rs12935810, rs74702385, rs17136707, rs8061182, rs111590482, rs4786454, rs2283497, rs2531967, rs3730119, rs13337675, rs12920508, rs12599911, rs2531971 or rs2238448.

In a particular embodiment the primer comprises a strand of DNA that is 15 to 30 nucleotides in length and hybridizes under high stringency conditions to a region of chromosome 16 adjacent to rs11647778.

In a particular embodiment, the primer comprises a strand of DNA that is 15 to 30 nucleotides in length and hybridizes under high stringency conditions to a region of chromosome 16 adjacent to rs11647778, rs1967309, rs12595857, rs2239310, rs11647828, rs8049452, rs12935810, rs74702385, rs17136707, rs8061182, rs111590482, rs4786454, rs2283497, rs2531967, rs3730119, rs2238448 or rs13337675.

In a particular embodiment, the primer comprises strand of DNA that is 15 to 30 nucleotides in length and hybridizes under high stringency conditions to a region of chromosome 16 adjacent to rs11647778.

In another embodiment, the reagent is a primer comprising a strand of DNA that is 15 to 30 nucleotides in length and hybridizes under high stringency conditions to a region of chromosome 16 overlapping with rs11647778, rs1967309, rs12595857, rs2239310, rs11647828, rs8049452, rs12935810, rs74702385, rs17136707, rs8061182, rs111590482, rs4786454, rs2283497, rs2531967, rs3730119, rs13337675, rs12920508, rs12599911, rs2531971 or rs2238448.

In another embodiment the reagent is a primer comprising a strand of DNA that is 15 to 30 nucleotides in length and hybridizes under high stringency conditions to a region of chromosome 16 overlapping with rs11647778.

In another embodiment the reagent is a primer a comprising strand of DNA that is 15 to 30 nucleotides in length and hybridizes under high stringency conditions to a region of chromosome 16 overlapping with rs11647778, rs1967309, rs12595857, rs2239310, rs11647828, rs8049452, rs12935810, rs74702385, rs17136707, rs8061182, rs111590482, rs4786454, rs2283497, rs2531967, rs3730119, rs2238448 or rs13337675.

In another embodiment the reagent is a primer comprising a strand of DNA that is 15 to 30 nucleotides in length and hybridizes under high stringency conditions to a region of chromosome 16 overlapping with rs11647778.

In another embodiment the probe is a nucleic acid that is 15 to 30 nucleotides in length and hybridizes under high stringency conditions to a region of chromosome 16 overlapping with rs11647778, rs1967309, rs12595857, rs2239310, rs11647828, rs8049452, rs12935810, rs74702385, rs17136707, rs8061182, rs111590482, rs4786454, rs2283497, rs2531967, rs3730119, rs13337675, rs12920508, rs12599911, rs2531971 or rs2238448.

In another embodiment the probe is a nucleic acid that is 15 to 30 nucleotides in length and hybridizes under high stringency conditions to a region of chromosome 16 overlapping with rs11647778.

In another embodiment the probe is a nucleic acid that is 15 to 30 nucleotides in length and hybridizes under high stringency conditions to a region of chromosome 16 overlapping with rs11647778, rs1967309, rs12595857, rs2239310, rs11647828, rs8049452, rs12935810, rs74702385, rs17136707, rs8061182, rs111590482, rs4786454, rs2283497, rs2531967, rs3730119, rs2238448 or rs13337675.

In another embodiment the probe is a nucleic acid that is 15 to 30 nucleotides in length and hybridizes under high stringency conditions to a region of chromosome 16 overlapping with rs11647778.

In another embodiment the probe is a nucleic acid that is 15 to 30 nucleotides in length and hybridizes under high stringency conditions to an oligonucleotide selected from SEQ. ID. NO. 1 to SEQ. ID. NO 21.

In another embodiment the probe is a nucleic acid that is 15 to 30 nucleotides in length and hybridizes under high stringency conditions to an oligonucleotide having the sequence of SEQ. ID NO 21.

In another embodiment, the probe is a nucleic acid that is 15 to 30 nucleotides in length and hybridizes under high stringency conditions to an oligonucleotide having the sequence of SEQ. ID NO. 19.

In a particular embodiment, the invention provides the method wherein the HDL-raising or HDL mimicking agents a CETP inhibitor/modulator, in particular, wherein the HDL-raising or HDL mimicking agent is S-(2-{[1-(2-ethyl-butyl)-cyclohexanecarbonyl]-amino}-phenyl) ester.

In yet another embodiment, the invention provides a use of HDL-raising or HDL mimicking agent, in particular a CETP inhibitor/modulator, in the manufacture of a medicament for the treatment or prevention of a cardiovascular disorder in a subject in need thereof, wherein the subject has an improved response genotype at rs11647778 and optionally one or more of the following sites: rs1967309, rs12595857, rs2239310, rs11647828, rs8049452, rs12935810, rs74702385, rs17136707, rs8061182, rs111590482, rs4786454, rs2283497, rs2531967, rs3730119, rs2238448, or rs13337675.

In a particular embodiment, the invention provides the use as defined herein, wherein the subject has an improved response polymorphism at rs11647778.

In another embodiment, the invention provides a HDL-raising or HDL mimicking agent, in particular a CETP inhibitor/modulator for use in the treatment or prevention of a cardiovascular disorder in a subject in need thereof, wherein the subjects carries genetic marker rs11647778/CC and optionally one or more genetic markers selected from: rs12595857/GG; rs1967309/AA; rs111590482/AG; rs111590482/GG; rs11647828/GG; rs12935810/GG; rs17136707/GG; rs2239310/GG; rs2283497/AA; rs2531967/AA; rs3730119/AA; rs4786454/AA; rs74702385/GA; rs74702385/AA; rs8049452/GG; rs8061182/AA; rs1967309/GA, rs12595857/AG, rs13337675/AG, rs13337675/GG, rs17136707/AG, rs2239310/AG, rs2283497/CA, rs2531967/GA, rs3730119/GA, rs4786454/GA, rs8049452/GA, rs8061182/AG, rs12595857/GG, rs1967309/AA, rs111590482/AG, rs111590482/GG, rs11647828/GG, rs12935810/GG, rs17136707/GG, rs2239310/GG, rs2283497/AA, rs2531967/AA, rs3730119/AA, rs4786454/AA, rs74702385/GA, rs74702385/AA, rs8049452/GG, rs8061182/AA, rs12935810/GA, rs12935810/AA, rs11647828/AA, rs2531967/GG, rs3730119/GG, rs2239310/AA, rs12595857/AA, rs111590482/AA, rs74702385/GG, rs1967309/GG, rs2283497/CC, rs8061182/GG, rs17136707/AA, rs8049452/AA, rs4786454/GG, rs13337675/AA, rs2238448/TT, and rs11647828/AG.

In another embodiment, the invention provides methods for treating or preventing a cardiovascular disorder, comprising administering to a subject in need thereof a therapeutically effective amount of a HDL-raising or HDL mimicking agent, in particular a CETP inhibitor/modulator, wherein the subject has an improved response genotype at rs11647778 and optionally at one or more of the following sites: rs1967309, rs12595857, rs2239310, rs11647828, rs8049452, rs12935810, rs74702385, rs17136707, rs8061182, rs111590482, rs4786454, rs2283497, rs2531967, rs3730119 rs2238448, and rs13337675.

In another embodiment, the invention provides methods for treating or preventing a cardiovascular disorder, comprising administering to a subject in need thereof an amount of a HDL-raising or HDL mimicking agent, in particular a CETP inhibitor/modulator, that is effective for treating or preventing the cardiovascular disorder, wherein the subject has an improved response genotype at rs11647778 and optionally at one or more of the following sites: rs1967309, rs12595857, rs2239310, rs11647828, rs8049452, rs12935810, rs74702385, rs17136707, rs8061182, rs111590482, rs4786454, rs2283497, rs2531967, rs3730119, rs2238448, and rs13337675.

In another embodiment, the invention provides a method for treating or preventing a cardiovascular disorder, comprising administering to a subject having an improved response genotype at rs11647778 and optionally at one or more of the following sites: rs1967309, rs12595857, rs2239310, rs11647828, rs8049452, rs12935810, rs74702385, rs17136707, rs8061182, rs111590482, rs4786454, rs2283497, rs2531967, rs3730119, rs13337675, rs2238448a therapeutically effective amount of a HDL-raising or HDL mimicking agent, in particular a CETP inhibitor/modulator.

In another embodiment, the invention provides a method for treating or preventing a cardiovascular disorder, comprising administering to a subject having an improved response genotype at rs11647778 and optionally at one or more of the following sites: rs1967309, rs12595857, rs2239310, rs11647828, rs8049452, rs12935810, rs74702385, rs17136707, rs8061182, rs111590482, rs4786454, rs2283497, rs2531967, rs3730119, rs13337675, rs2238448 an amount of an HDL-raising or HDL mimicking agent, in particular a CETP inhibitor/modulator that is effective for treating or preventing the cardiovascular disorder.

In a particular embodiment, the invention provides method for treating a cardiovascular disorder, comprising administering to a patient in need thereof a therapeutically effective amount of a HDL-raising or HDL mimicking agent, in particular a CETP inhibitor/modulator, wherein the subjects treated have an improved response genotype, wherein the genotype is rs11647778/CC and optionally rs12595857/GG, rs1967309/AA, rs111590482/AG, rs111590482/GG, rs11647828/GG, rs12935810/GG, rs17136707/GG, rs2239310/GG, rs2283497/AA, rs2531967/AA, rs3730119/AA, rs4786454/AA, rs74702385/GA, rs74702385/AA, rs8049452/GG and or rs8061182/AA.

In a particular embodiment, the invention provides methods for treating or preventing a cardiovascular disorder, comprising administering to a subject in need thereof an amount of an HDL-raising or HDL mimicking agent, in particular a CETP inhibitor/modulator, that is effective for treating or preventing the cardiovascular disorder, wherein the subject carries the genotype rs11647778/CC and optionally rs12595857/GG, rs1967309/AA, rs111590482/AG, rs111590482/GG, rs11647828/GG, rs12935810/GG, rs17136707/GG, rs2239310/GG, rs2283497/AA, rs2531967/AA, rs3730119/AA, rs4786454/AA, rs74702385/GA, rs74702385/AA, rs8049452/GG, rs2238448/TT, and/or rs8061182/AA.

In another embodiment, the invention provides a method for treating or preventing a cardiovascular disorder, comprising administering to a subject having an improved response genotype at rs11647778/CC and optionally rs12595857/GG, rs1967309/AA, rs111590482/AG, rs111590482/GG, rs11647828/GG, rs12935810/GG, rs17136707/GG, rs2239310/GG, rs2283497/AA, rs2531967/AA, rs3730119/AA, rs4786454/AA, rs74702385/GA, rs74702385/AA, rs8049452/GG and or rs8061182/AA, a therapeutically effective amount of a HDL-raising or HDL mimicking agent, in particular a CETP inhibitor/modulator.

In another embodiment, the invention provides a method for treating or preventing a cardiovascular disorder, comprising administering to a subject having the genotype rs11647778/CC and optionally rs12595857/GG, rs1967309/AA, rs111590482/AG, rs111590482/GG, rs11647828/GG, rs12935810/GG, rs17136707/GG, rs2239310/GG, rs2283497/AA, rs2531967/AA, rs3730119/AA, rs4786454/AA, rs74702385/GA, rs74702385/AA, rs8049452/GG, rs2238448/TT, and/or rs8061182/AA, an amount of an HDL-raising or HDL mimicking agent, in particular a CETP inhibitor/modulator that is effective for treating or preventing the cardiovascular disorder.

In another embodiment, the invention provides a method for treating or preventing a cardiovascular disorder, comprising administering to a subject in need thereof a therapeutically effective amount of a HDL-raising or HDL mimicking agent, in particular a CETP inhibitor/modulator, wherein the subjects treated have an improved response genotype at rs11647778 and optionally rs1967309, rs2238448 or rs12595857.

In another embodiment, the invention provides a method for treating or preventing a cardiovascular disorder, comprising administering to a subject in need thereof an amount of an HDL-raising or HDL mimicking agent, in particular a CETP inhibitor/modulator, that is effective for treating or preventing the cardiovascular disorder, wherein the subject has an improved response genotype at rs11647778 and optionally rs1967309, rs2238448, or rs12595857.

In another embodiment, the invention provides a method for treating or preventing a cardiovascular disorder, comprising administering to a subject having an improved response genotype at rs11647778 and optionally rs1967309, rs2238448 or rs12595857, a therapeutically effective amount of a HDL-raising or HDL mimicking agent, in particular a CETP inhibitor/modulator.

In another embodiment, the invention provides a method for treating or preventing a cardiovascular disorder, comprising administering to a subject having an improved response genotype at rs11647778 and optionally rs1967309, rs2238448, or rs12595857, an amount of an HDL-raising or HDL mimicking agent, in particular a CETP inhibitor/modulator that is effective for treating or preventing the cardiovascular disorder.

In another embodiment, the invention provides a method for treating or preventing a cardiovascular disorder, comprising administering to a subject in need thereof a therapeutically effective amount of a HDL-raising or HDL mimicking agent, in particular a CETP inhibitor/modulator, wherein the subjects treated have an improved response genotype at rs11647778 and optionally rs1967309.

In another embodiment, the invention provides a method for treating or preventing a cardiovascular disorder, comprising administering to a subject in need thereof an amount of an HDL-raising or HDL mimicking agent, in particular a CETP inhibitor/modulator, that is effective for treating or preventing the cardiovascular disorder, wherein the subject has an improved response genotype at rs11647778 and optionally rs1967309.

In another embodiment, the invention provides a method for treating or preventing a cardiovascular disorder, comprising administering to a subject having an improved response genotype at rs11647778 and optionally rs1967309, a therapeutically effective amount of a HDL-raising or HDL mimicking agent, in particular a CETP inhibitor/modulator.

In another embodiment, the invention provides a method for treating or preventing a cardiovascular disorder, comprising administering to a subject having an improved response genotype at rs11647778 and optionally rs1967309, an amount of an HDL-raising or HDL mimicking agent, in particular a CETP inhibitor/modulator that is effective for treating or preventing the cardiovascular disorder.

In a particular embodiment, the invention provides the HDL-raising or HDL mimicking agent, in particular a CETP inhibitor/modulator for use in the treatment or prevention of cardiovascular disorder, wherein the subject treated carries an improved response genotype rs11647778.

In a particular embodiment, the invention provides the HDL-raising or HDL mimicking agent as herein defined wherein the improved response genotype is CC.

In a particular embodiment, the invention provides the HDL-raising or HDL mimicking agent, in particular a CETP inhibitor/modulator, for use in the treatment or prevention of a cardiovascular disorder in a subject, wherein the subject carries an improved response genotype rs11647778. In a particular embodiment, the invention provides the HDL-raising or HDL mimicking agent as herein defined, wherein the improved response genotype at rs11647778 is CC.

In a particular embodiment, the invention provides an HDL-raising or HDL mimicking agent as herein described, wherein the cardiovascular disorder is selected from the group consisting of atherosclerosis, peripheral vascular disease, dyslipidemia, hyperbetalipoproteinemia, hypoalphalipoproteinemia, hypercholesterolemia, hypertriglyceridemia, familial-hypercholesterolemia, angina, ischemia, cardiac ischemia, stroke, myocardial infarction, reperfusion injury, angioplastic restenosis, hypertension, and vascular complications of diabetes, obesity or endotoxemia in a mammal.

In a particular embodiment, the invention provides the HDL-raising or HDL mimicking agent as herein described, wherein the cardiovascular disorder is cardiovascular disease, coronary heart disease, coronary artery disease, hypoalphalipoproteinemia, hyperbetalipoproteinemia, hypercholesterolemia, hyperlipidemia, atherosclerosis, hypertension, hypertriglyceridemia, hyperlipidoproteinemia, peripheral vascular disease, angina, ischemia or myocardial infarction.

In a particular embodiment, the invention provides the HDL-raising or HDL mimicking agent as herein described, wherein the HDL-raising or mimicking agent is a HDL-raising agent, particularly a CETP inhibitor/modulator, more particularly is S-(2-{[1-(2-ethyl-butyl)-cyclohexanecarbonyl]-amino}-phenyl) ester.

In another embodiment, the invention provides S-(2-{[1-(2-ethyl-butyl)-cyclohexanecarbonyl]-amino}-phenyl) ester for treating or preventing a cardiovascular disorder in a subject in need thereof, who has the genotype rs11647778/CC and optionally rs12595857/GG, rs1967309/AA, rs111590482/AG, rs111590482/GG, rs11647828/GG, rs12935810/GG, rs17136707/GG, rs2239310/GG, rs2283497/AA, rs2531967/AA, rs3730119/AA, rs4786454/AA, rs74702385/GA, rs74702385/AA, rs8049452/GG, rs2238448/TT, or rs8061182/AA, more particularly wherein the genotype is rs11647778/CC and optionally rs1967309/AA.

In another embodiment, the invention provides S-(2-{[1-(2-ethyl-butyl)-cyclohexanecarbonyl]-amino}-phenyl) ester for treating or preventing patient with cardiovascular disorder, who carries an improved response genotype, in particular wherein the genotype is rs11647778/CC and optionally rs12595857/GG, rs1967309/AA, rs111590482/AG, rs111590482/GG, rs11647828/GG, rs12935810/GG, rs17136707/GG, rs2239310/GG, rs2283497/AA, rs2531967/AA, rs3730119/AA, rs4786454/AA, rs74702385/GA, rs74702385/AA, rs8049452/GG or rs8061182/AA, more particularly wherein the genotype is rs11647778/CC and optionally rs1967309/AA.

In a particular embodiment, the invention provides S-(2-{[1-(2-ethyl-butyl)-cyclohexanecarbonyl]-amino}-phenyl) ester for treating or preventing a patient with a cardiovascular disorder who carries an improved response genotype, wherein the cardiovascular disorder is selected from the group consisting of atherosclerosis, peripheral vascular disease, dyslipidemia, hyperbetalipoproteinemia, hypoalphalipoproteinemia, hypercholesterolemia, hypertriglyceridemia, familial-hypercholesterolemia, angina, ischemia, cardiac ischemia, stroke, myocardial infarction, reperfusion injury, angioplastic restenosis, hypertension, and vascular complications of diabetes, obesity or endotoxemia in a mammal.

In a particular embodiment, the invention provides S-(2-{[1-(2-ethyl-butyl)-cyclohexanecarbonyl]-amino}-phenyl) ester for treating or preventing a cardiovascular disorder in a subject in need thereof who has an improved response genotype, wherein the cardiovascular disorder is atherosclerosis, peripheral vascular disease, dyslipidemia, hyperbetalipoproteinemia, hypoalphalipoproteinemia, hypercholesterolemia, hypertriglyceridemia, familial-hypercholesterolemia, angina, ischemia, cardiac ischemia, stroke, myocardial infarction, reperfusion injury, angioplastic restenosis, hypertension, and a vascular complication of diabetes, obesity or endotoxemia.

In a particular embodiment, the invention provides S-(2-{[1-(2-ethyl-butyl)-cyclohexanecarbonyl]-amino}-phenyl) ester for treating or preventing a patient with a cardiovascular disorder who carries an improved response genotype, wherein the cardiovascular disorder is selected from the group consisting of cardiovascular disease, coronary heart disease, coronary artery disease, hypoalphalipoproteinemia, hyperbetalipoproteinemia, hypercholesterolemia, hyperlipidemia, atherosclerosis, hypertension, hypertriglyceridemia, hyperlipidoproteinemia, peripheral vascular disease, angina, ischemia, and myocardial infarction.

In a particular embodiment, the invention provides S-(2-{[1-(2-ethyl-butyl)-cyclohexanecarbonyl]-amino}-phenyl) ester for treating or preventing a cardiovascular disorder in a subject in need thereof who has an improved response genotype, wherein the cardiovascular disorder is cardiovascular disease, coronary heart disease, coronary artery disease, hypoalphalipoproteinemia, hyperbetalipoproteinemia, hypercholesterolemia, hyperlipidemia, atherosclerosis, hypertension, hypertriglyceridemia, hyperlipidoproteinemia, peripheral vascular disease, angina, ischemia, or myocardial infarction.

In another embodiment, the invention provides a method of predicting whether a patient diagnosed with or having one or more symptoms of a cardiovascular disease has an increased likelihood of benefiting from treatment with an HDL-raising or HDL mimicking agent, in particular a CETP inhibitor/modulator, comprising screening a sample obtained from said patient for a genetic marker in the Adenylate Cyclase Type 9 gene (ADCY9) selected from rs11647778/CC, rs12595857/GG, rs1967309/AA, rs111590482/AG, rs111590482/GG, rs11647828/GG, rs12935810/GG, rs17136707/GG, rs2239310/GG, rs2283497/AA, rs2531967/AA, rs3730119/AA, rs4786454/AA, rs74702385/GA, rs74702385/AA, rs8049452/GG, rs2238448/TT, or rs8061182/AA, wherein the presence of the genetic marker indicates that the patient has an increased likelihood of benefiting from said treatment with an HDL-raising or HDL mimicking agent. In a particular embodiment, the genetic marker screened is rs11647778/CC and optionally rs12595857/GG, rs2238448/TT, and/or rs1967309/AA. More particularly the genetic marker screened is rs11647778/CC and optionally rs1967309/AA.

In another embodiment, the invention provides a method of predicting whether a cardiovascular disorder patient has an increased likelihood of benefiting from treatment with a HDL-raising or HDL mimicking agent, in particular a CETP inhibitor/modulator, comprising screening a sample isolated from said patient for a genetic marker in the Adenylate Cyclase Type 9 gene (ADCY9) selected from rs11647778/CC, rs12595857/GG, rs1967309/AA, rs111590482/AG, rs111590482/GG, rs11647828/GG, rs12935810/GG, rs17136707/GG, rs2239310/GG, rs2283497/AA, rs2531967/AA, rs3730119/AA, rs4786454/AA, rs74702385/GA, rs74702385/AA, rs8049452/GG, rs8061182/AA, wherein the patient has an increased likelihood of benefiting from said treatment with an HDL-raising or HDL mimicking agent. In a particular embodiment, the genetic marker screened is rs11647778/CC and optionally selected from rs12595857/GG; rs1967309/AA. More particularly the genetic marker screened is rs11647778/CC and optionally rs1967309/AA.

In a further embodiment, the invention provides a method of selecting a patient who is likely to respond to an HDL-raising or HDL mimicking agent, the method comprising:
(a) determining the genotype at rs11647778 in a sample from a patient diagnosed with or having one or more symptoms of a cardiovascular disorder, and
(b) selecting a patient with genotype CC as more likely to respond to an HDL-raising or HDL mimicking agent.

In yet a further embodiment, the method further comprises determining the genotype at rs1967309 and/or rs2238448, and selecting a patient with genotype AA at rs1967309 and/or genotype TT at rs2238448 as likely to respond to an HDL-raising or HDL mimicking agent. In certain embodiments, the method further comprises administering an HDL-raising or HDL mimicking agent (e.g. dalcetrapib) to the selected patient.

In a further embodiment, the invention provides a method of selecting a patient with a cardiovascular disorder as likely to respond to a therapy comprising HDL-raising or HDL mimicking agent, the method comprising:
(a) detecting an CC genotype at rs11647778 in a sample from the patient,
(b) selecting the patient as more likely to respond to a therapy comprising HDL-raising or HDL mimicking agent when rs11647778 with CC genotype is detected in the sample from the patient.

In yet a further embodiment, the invention provides a method of selecting a patient with a cardiovascular disorder as likely to respond to a therapy comprising HDL-raising or HDL mimicking agent, the method comprising:
(a) detecting an CC genotype at rs11647778 and AA genotype at rs1967309 in a sample from the patient,
(b) selecting the patient as more likely to respond to a therapy comprising HDL-raising or HDL mimicking agent when rs11647778 with CC and rs1967309 with AA genotype is detected in the sample from the patient.

In a particular embodiment, the invention provides the method herein described, wherein the presence of an CC genotype at rs11647778 in a reference sample (prior to the therapy with a HDL-raising or HDL mimicking agent according to the invention) indicates that the patient is more likely to respond to the therapy with a HDL-raising or HDL mimicking agent.

In a particular embodiment, the invention provides the method herein described, wherein the presence of CC genotype at rs11647778 and AA genotype at rs1967309 in a reference sample indicates that the patient is more likely to respond to the therapy with a HDL-raising or HDL mimicking agent.

In a particular embodiment, the invention provides the method herein described which further comprises c) selecting the therapy comprising a HDL-raising or HDL mimicking agent.

In a particular embodiment, the invention provides the method herein described wherein determining the genotype at rs11647778 in a sample from the patient comprises contacting the sample with a genotype-specific reagent (e.g. primer and/or probe) that binds to the rs11647778 sequence, thereby forming a complex between the reagent and rs11647778 sequence, and detecting the complex formed, thereby determining the genotype at rs11647778.

A method for determining the prognosis of a clinical response in a human patient to a HDL-raising or HDL mimicking agent, comprising determining the presence of at least one polymorphism in the ADCY9 gene of the patient in which the polymorphism site is associated with a delayed, partial sub-optimal or lacking clinical response to said HDL-raising or mimicking agent wherein at least one polymorphism site is rs11647778.

A method for determining the prognosis of a clinical response in a human patient to a HDL-raising or HDL mimicking agent, comprising determining the presence of at least one polymorphism in the ADCY9 gene of the patient in which the polymorphism site is associated with a delayed, partial sub-optimal or lacking clinical response to said HDL-raising or mimicking agent wherein at least two polymorphism sites are rs11647778 and rs1967309.

In another embodiment, the invention provides a method for determining the prognosis of a clinical response in a human patient to a HDL-raising or HDL mimicking agent, comprising determining the genotype of at least one polymorphism site in the ADCY9 gene of the patient in which the polymorphism site is associated with a delayed, partial sub-optimal or lacking clinical response to said HDL-raising or mimicking agent. In one embodiment, the polymorphism site is rs11647778 and the GG genotype is indicative of a delayed, partial sub-optimal or lacking clinical response to said HDL-raising or mimicking agent. In another embodiment, the polymorphism site is rs1967309 and the GG genotype is indicative of a delayed, partial sub-optimal or lacking clinical response to said HDL-raising or mimicking agent. In another embodiment, the polymorphism site is rs2238448 and the CC genotype is indicative of a delayed, partial sub-optimal or lacking clinical response to said HDL-raising or mimicking agent.

In a particular embodiment, the invention provides the method herein described, wherein the polymorphism is determined by a genotyping analysis.

In a particular embodiment, the invention provides the method herein described, wherein the genotyping analysis comprises a microarray analysis or a mass-spectrometric analysis or the use of polymorphism-specific primers and/or probes, in particular a primer extension reaction.

In a particular embodiment, the invention provides the method herein described, wherein HDL-raising or HDL mimicking agent is a HDL-raising agent, in particular a CETP inhibitor/modulator, more particularly S-(2-{[1-(2-ethyl-butyl)-cyclohexanecarbonyl]-amino}-phenyl) ester.

In a particular embodiment, the "CETP inhibitor/modulator" is thioisobutyric acid S-(2-{[1-(2-ethyl-butyl)-cyclohexanecarbonyl]-amino}-phenyl) ester, also known as S-[2-([[1-(2-ethylbutyl)-cyclohexyl]-carbonyl]amino)phenyl]2-methylpropanethioate, dalcetrapib or a compound of formula I

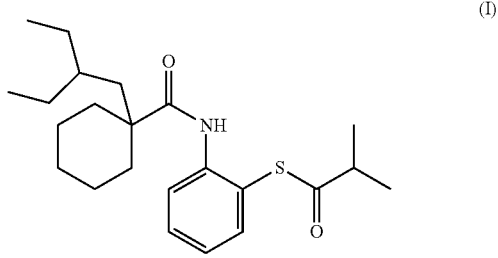 [SMILES: CCC(CC)CC1(C(=O)Nc2ccccc2SC(=O)C(C)C)CCCCC1]

(I)

S-[2-([[1-(2-ethylbutyl)cyclohexyl] carbonyl] amino) phenyl] 2-methylpropanethioate has been shown to be an inhibitor of CETP activity in humans (de Grooth et al., Circulation, 105, 2159-2165 (2002)) and rabbits (Shinkai et al., J. Med. Chem., 43, 3566-3572 (2000); Kobayashi et al., Atherosclerosis, 162, 131-135 (2002); and Okamoto et al., Nature, 406 (13), 203-207 (2000)). S-[2-([[1-(2-ethylbutyl) cyclohexyl] carbonyl] amino) phenyl] 2-methylpropanethioate has been shown to increase plasma HDL cholesterol in humans (de Grooth et al., supra) and in rabbits (Shinkai et al., supra; Kobayashi et al., supra; Okamoto et al., supra). Moreover, S-[2-([[1-(2-ethylbutyl) cyclohexyl] carbonyl] amino) phenyl] 2-methylpropanethioate has been shown to decrease LDL cholesterol in humans (de Grooth et al., supra) and rabbits (Okamoto et al., supra). S-[2-([[1-(2-ethylbutyl) cyclohexyl] carbonyl] amino) phenyl] 2-methylpropanethioate, as well as methods of making and using the compound, are described in EP1020439, Shinkai et al., J. Med. Chem. 43:3566-3572 (2000) or WO 2007/051714, WO 2008/074677 or WO2011/000793.

In a preferred embodiment the CETP inhibitor/modulator (e.g. compound of formula I) is a solid in crystalline or amorphous form, or more preferably in crystalline form. In a particular embodiment S-[2-([[1-(2-ethylbutyl)-cyclohexyl]-carbonyl]amino)phenyl]2-methylpropanethioate is in crystalline form A as disclosed in WO2012/069087. Form A is characterized by an X-ray powder diffraction pattern having peaks at about 7.9°, 8.5°, 11.7°, 12.7°, 17.1°, 18.0°, 18.5°, 20.2°, 22.1°, 24.7°±0.2°, particularly by an XRPD peaks observed at an angle of diffraction 2Theta of 7.9°, 11.7°, 17.1°, 18.5° (±0.2°).

Other CETP inhibitors known in the art and useful in the present invention include: evacetrapib, anacetrapib and torcetrapib, particularly evacetrapib and anacetrapib.

Accordingly, the invention provides a method for the treatment or prevention of a cardiovascular disorder in a mammal, which method comprises administering to a mammal (preferably a mammal in need thereof) a therapeutically effective amount of the pharmaceutical composition. The mammal preferably is a human (i.e., a male or female human). The human can be of any race (e. g., Caucasian or Oriental).

The cardiovascular disorder particularly is atherosclerosis, peripheral vascular disease, dyslipidemia, hyperbetalipoproteinemia, hypoalphalipoproteinemia, hypercholesterolemia, hypertriglyceridemia, familial-hypercholesterolemia, angina, ischemia, cardiac ischemia, stroke, myocardial infarction, reperfusion injury, angioplastic restenosis, hypertension, and vascular complications of diabetes, obesity or endotoxemia. More particularly, the cardiovascular disorder is cardiovascular disease, coronary heart disease, coronary artery disease, hypoalphalipoproteinemia, hyperbetalipoproteinemia, hypercholesterolemia, hyperlipidemia, atherosclerosis, hypertension, hypertriglyceridemia, hyperlipidoproteinemia, peripheral vascular disease, angina, ischemia or myocardial infarction.

In certain embodiments of the present invention, the subjects or patients are administered between 100 mg to 600 mg of S-[2-([[1-(2-ethylbutyl)-cyclohexyl-carbonyl]amino) phenyl]2-methylpropanethioate. In particular, the subjects or patients are administered between 150 mg to 450 mg of S-[2-([[1-(2-ethylbutyl)-cyclohexyl]-carbonyl]amino)phenyl]2-methylpropanethioate. More particularly, the subjects or patients are administered between 250 mg to 350 mg of S-[2-([[1-(2-ethylbutyl)-cyclohexyl]-carbonyl]amino)phenyl]2-methylpropanethioate. Most particularly, the subjects or patients are administered between 250 mg to 350 mg of S-[2-([[1-(2-ethylbutyl)-cyclohexyl]-carbonyl]amino)phenyl]2-methylpropanethioate.

In another embodiment of the present invention, the subject for pediatric use are administered between 25 mg to 300 mg of S-[2-([[1-(2-ethylbutyl)-cyclohexyl]-carbonyl]amino)phenyl]2-methylpropanethioate. In particular the subject for pediatric use are administered 75 mg to 150 mg of S-[2-([[1-(2-ethylbutyl)-cyclohexyl]-carbonyl]amino)phenyl]2-methylpropanethioate.

The CETP inhibitor can be administered to the mammal at any suitable dosage (e. g., to achieve a therapeutically effective amount). For example, a suitable dose of a therapeutically effective amount of S-[2-([[1-(2-ethylbutyl)-cyclohexyl]-carbonyl]amino)phenyl]2-methylpropanethioate for administration to a patient will be between approximately 100 mg to about 1800 mg per day. A desirable dose is preferably about 300 mg to about 900 mg per day. A preferred dose is about 600 mg per day.

Genotyping Methods

Identification of the particular genotype of a DNA sample may be performed by any of a number of methods well known to one of skill in the art. For example, identification of the polymorphism can be accomplished by cloning of the allele and sequencing it using techniques well known in the art. Alternatively, the gene sequences can be amplified from genomic DNA, e.g. using PCR, and the product sequenced. Numerous methods are known in the art for isolating and analyzing a subject's DNA for a given genetic marker including polymerase chain reaction (PCR), ligation chain reaction (LCR) or ligation amplification and amplification methods such as self sustained sequence replication. Several non-limiting methods for analyzing a patient's DNA for mutations at a given genetic locus are described below.

DNA microarray technology, e.g., DNA chip devices and high-density microarrays for high-throughput screening applications and lower-density microarrays, may be used. Methods for microarray fabrication are known in the art and include various inkjet and microjet deposition or spotting technologies and processes, in situ or on-chip photolithographic oligonucleotide synthesis processes, and electronic DNA probe addressing processes. The DNA microarray hybridization applications has been successfully applied in the areas of gene expression analysis and genotyping for point mutations, single nucleotide polymorphisms (SNPs) and short tandem repeats (STRs). Additional methods include interference RNA microarrays and combinations of microarrays and other methods such as laser capture microdissection (LCM), comparative genomic hybridization (CGH) and chromatin immunoprecipitation (ChiP). See, e.g., He et al. (2007) Adv. Exp. Med. Biol. 593: 117-133 and Heller (2002) Annu. Rev. Biomed. Eng. 4: 129-153. Other methods include PCR, xMAP, invader assay, mass spectrometry, and pyrosequencing (Wang et al. (2007) Microarray Technology and Cancer Gene Profiling Vol 593 of book series Advances in Experimental Medicine and Biology, pub. Springer New York).

Another detection method is allele specific hybridization using probes overlapping the polymorphic site and having about 5, or alternatively 10, or alternatively 20, or alternatively 25, or alternatively 30 nucleotides around the polymorphic region. For example, several probes capable of hybridizing specifically to the allelic variant or genetic marker of interest are attached to a solid phase support, e.g., a "chip". Oligonucleotide probes can be bound to a solid support by a variety of processes, including lithography. Mutation detection analysis using these chips comprising oligonucleotides, also termed "DNA probe arrays" is described e.g., in Cronin et al. (1996) Human Mutation 7':244.

In other detection methods, it is necessary to first amplify at least a portion of the gene prior to identifying the allelic variant. Amplification can be performed, e.g., by PCR and/or LCR or other methods well known in the art.

In some cases, the presence of the specific allele in DNA from a subject can be shown by restriction enzyme analysis. For example, the specific nucleotide polymorphism can result in a nucleotide sequence comprising a restriction site which is absent from the nucleotide sequence of another allelic variant.

In a further embodiment, protection from cleavage agents (such as a nuclease, hydroxylamine or osmium tetroxide and with piperidine) can be used to detect mismatched bases in RNA/RNA DNA/DNA, or RNA/DNA heteroduplexes (see, e.g., Myers et al. (1985) Science 230: 1242). In general, the technique of "mismatch cleavage" starts by providing duplexes formed by hybridizing a probe, e.g., RNA or DNA, which is optionally labeled, comprising a nucleotide sequence of the allelic variant of the gene with a sample nucleic acid, obtained from a tissue sample. The double-stranded duplexes are treated with an agent that cleaves single-stranded regions of the duplex such as those formed from base pair mismatches between the control and sample strands. For instance, RNA/DNA duplexes can be treated with RNase and DNA/DNA hybrids treated with SI nuclease to enzymatically digest the mismatched regions. Alternatively, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine whether the control and sample nucleic acids have an identical nucleotide sequence or in which nucleotides they are different. See, for example, U.S. Pat. No. 6,455,249; Cotton et al. (1988) Proc. Natl. Acad. Sci. USA 85:4397; Saleeba et al. (1992) Meth. Enzymol. 217:286-295.

Alterations in electrophoretic mobility may also be used to identify the particular allelic variant. For example, single strand conformation polymorphism (SSCP) may be used to detect differences in electrophoretic mobility between mutant and wild type nucleic acids (Orita et al. (1989) Proc Natl. Acad. Sci USA 86:2766; Cotton (1993) Mutat. Res. 285: 125-144 and Hayashi (1992) Genet. Anal. Tech. Appl. 9:73-79). Single-stranded DNA fragments of sample and control nucleic acids are denatured and allowed to renature. The secondary structure of single-stranded nucleic acids varies according to sequence; the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In another preferred embodiment, the subject method utilizes heteroduplex analysis to separate double stranded heteroduplex molecules on the basis of changes in electrophoretic mobility (Keen et al. (1991) Trends Genet. 7:5).

The identity of the allelic variant or genetic marker may also be obtained by analyzing the movement of a nucleic acid comprising the polymorphic region in polyacrylamide gels containing a gradient of denaturant, which is assayed using denaturing gradient gel electrophoresis (DGGE) (Myers et al. (1985) Nature 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys. Chem. 265: 1275).

Examples of techniques for detecting differences of at least one nucleotide between 2 nucleic acids include, but are not limited to, selective oligonucleotide hybridization, selective amplification, or selective primer extension. For example, oligonucleotide probes may be prepared in which the known polymorphic nucleotide is placed centrally (allele-specific probes) and then hybridized to target DNA under conditions which permit hybridization only if a perfect match is found (Saiki et al. (1986) Nature 324: 163); Saiki et al. (1989) Proc. Natl. Acad. Sci. USA 86:6230). Such allele specific oligonucleotide hybridization techniques are used for the detection of the nucleotide changes in the polymorphic region of the gene. For example, oligonucleotide probes having the nucleotide sequence of the specific allelic variant are attached to a hybridizing membrane and this membrane is then hybridized with labeled sample nucleic acid. Analysis of the hybridization signal will then reveal the identity of the nucleotides of the sample nucleic acid.

Alternatively, allele specific amplification technology which depends on selective PCR amplification may be used in conjunction with the instant invention. Oligonucleotides used as primers for specific amplification may carry the allelic variant of interest in the center of the molecule (so that amplification depends on differential hybridization) (Gibbs et al. (1989) Nucl. Acids Res. 17:2437-2448) or at the extreme 3' end of one primer where, under appropriate conditions, mismatch can prevent, or reduce polymerase extension (Prossner (1993) Tibtech 11:238 and Newton et al. (1989) Nucl. Acids Res. 17:2503). This technique is also termed "PROBE" for PRobeOligo Base Extension. In addition it may be desirable to introduce a novel restriction site in the region of the mutation to create cleavage-based detection (Gasparini et al. (1992) Mol. Cell. Probes 6: 1).

In another embodiment, identification of the allelic variant or genetic marker is carried out using an oligonucleotide ligation assay (OLA), as described, e.g., in U.S. Pat. No. 4,998,617 and in Laridegren, U. et al. Science 241: 1077-1080 (1988). The OLA protocol uses two oligonucleotide probes which are designed to be capable of hybridizing to abutting sequences of a single strand of a target. One of the oligonucleotides is linked to a separation marker, e.g., biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al. (1990) Proc. Natl. Acad. Sci. USA 87:8923-8927). In this method, PCR is used to achieve the exponential amplification of target DNA, which is then detected using OLA. A variation of the OLA method as described in Tobe et al. (1996) Nucleic Acids Res. 24: 3728 each allele specific primers is labeled with a unique hapten, i.e. digoxigein and florescein and each OLA reaction is detected using hapten specific antibodies labeled with reporter enzymes.

The invention provides methods for detecting a single nucleotide polymorphism (SNP) in ADCY9. Because single nucleotide polymorphisms are flanked by regions of invariant sequence, their analysis requires no more than the determination of the identity of the single variant nucleotide and it is unnecessary to determine a complete gene sequence for each patient. Several methods have been developed to facilitate the analysis of SNPs.

The single base polymorphism can be detected by using a specialized exonuclease-resistant nucleotide, as disclosed, e.g., in U.S. Pat. No. 4,656,127. According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

A solution-based method may also be used to determine the identity of the nucleotide of the polymorphic site (WO 91/02087). As above, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method is described in WO 92/15712. This method uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. The method is usually a heterogeneous phase assay, in which the primer or the target molecule is immobilized to a solid phase.

Many other primer-guided nucleotide incorporation procedures for assaying polymorphic sites in DNA have been described (Komher, J. S. et al. (1989) Nucl. Acids. Res. 17:7779-7784; Sokolov, B. P. (1990) Nucl. Acids Res. 18:3671; Syvanen, A.-C, et al. (1990) Genomics 8:684-692; Kuppuswamy, M. N. et al. (1991) Proc. Natl. Acad. Sci. USA 88: 1143-1147; Prezant, T. R. et al. (1992) Hum. Mutat. 1: 159-164; Ugozzoli, L. et al. (1992) GATA 9: 107-112; Nyren, P. et al. (1993) Anal. Biochem. 208: 171-175). These methods all rely on the incorporation of labeled deoxynucleotides to discriminate between bases at a polymorphic site.

Moreover, it will be understood that any of the above methods for detecting alterations in a gene or gene product or polymorphic variants can be used to monitor the course of treatment or therapy.

The methods described herein may be performed, for example, by utilizing pre-packaged diagnostic kits, such as those described below, comprising at least one probe, primer nucleic acid, or reagent which may be conveniently used for genotyping, e.g., analyzing a genetic marker present in the ADCY9 gene to determine whether an individual has an increased likelihood of benefiting from treatment with HDL-raising or mimicking agent including a HDL-raising or HDL mimicking agent, in particular a CETP inhibitor/modulator. In particular the genetic markers are as described herein.

Primers or probes of the present invention, for use as reagents for genotyping genetic markers present in the ADCY9 gene, comprise a synthetic nucleotide sequence that is complimentary to and hybridizes with a contiguous sequence within the ADCY9 gene, of preferably 12 to 30 nucleotides, adjacent to or encompassing one or more SNPs selected from rs11647778, rs1967309, rs12595857, rs2239310, rs11647828, rs8049452, rs12935810, rs74702385, rs17136707, rs8061182, rs111590482, rs4786454, rs2283497, rs2531967, rs3730119, rs2238448 and rs13337675, preferably rs11647778. In other aspects a primer comprises 100 or fewer nucleotides, in certain aspects from 12 to 50 nucleotides or from 12 to 30 nucleotides. The primer is at least 70% identical to the contiguous sequence or to the complement of the contiguous nucleotide sequence, preferably at least 80% identical, and more preferably at least 90% identical. A primer or probe of the invention is preferably 15-50 nucleotides in length comprising a region of 15 to 20 nucleotides that is complimentary to a sequence selected from SEQ. ID. NO 1-21, in particular is complementary to sequence SEQ. ID No 1, 19 or 21. The degree of complimentary between a probe or primer and SEQ. ID. NO. 1-21 maybe 100%, 95%, 90%, 85%, 80% or 75%.

Oligonucleotides, including probes and primers, "specific for" a genetic allele or genetic marker bind either to the polymorphic region of a gene or bind adjacent to the polymorphic region of the gene. For oligonucleotides that are to be used as primers for amplification, primers are adjacent if they are sufficiently close to be used to produce a polynucleotide comprising the polymorphic region. In one embodiment, oligonucleotides are adjacent if they bind within about 1-2 kb, e.g. less than 1 kb from the polymorphism. Specific oligonucleotides are capable of hybridizing to a sequence, and under suitable conditions will not bind to a sequence differing by a single nucleotide.

Oligonucleotides of the invention, whether used as probes or primers, can be detectably labeled. Labels can be detected either directly, for example for fluorescent labels, or indirectly. Indirect detection can include any detection method known to one of skill in the art, including biotin-avidin interactions, antibody binding and the like. Fluorescently labeled oligonucleotides also can contain a quenching molecule. Oligonucleotides can be bound to a surface. In some embodiments, the surface is silica or glass. In some embodiments, the surface is a metal electrode.

Probes can be used to directly determine the genotype of the sample or can be used simultaneously with or subsequent to amplification. The term "probes" includes naturally occurring or recombinant single- or double-stranded nucleic acids or chemically synthesized nucleic acids. They may be labeled by nick translation, Klenow fill-in reaction, PCR or other methods known in the art. Probes of the present invention, their preparation and/or labeling are described in Sambrook et al. (1989) supra. A probe can be a polynucleotide of any length suitable for selective hybridization to a nucleic acid containing a polymorphic region of the invention. Length of the probe used will depend, in part, on the nature of the assay used and the hybridization conditions employed.

Labeled probes also can be used in conjunction with amplification of a polymorphism. (Holland et al. (1991) Proc. Natl. Acad. Sci. USA 88:7276-7280). U.S. Pat. No. 5,210,015 describes fluorescence-based approaches to provide real time measurements of amplification products during PCR. Such approaches have either employed intercalating dyes (such as ethidium bromide) to indicate the amount of double-stranded DNA present, or they have employed probes containing fluorescence-quencher pairs (also referred to as the "TaqMan®" approach) where the probe is cleaved during amplification to release a fluorescent molecule whose concentration is proportional to the amount of double-stranded DNA present. During amplification, the probe is digested by the nuclease activity of a polymerase when hybridized to the target sequence to cause the fluorescent molecule to be separated from the quencher molecule, thereby causing fluorescence from the reporter molecule to appear. The TaqMan® approach uses a probe containing a reporter molecule-quencher molecule pair that specifically anneals to a region of a target polynucleotide containing the polymorphism.

Probes can be affixed to surfaces for use as "gene chips." Such gene chips can be used to detect genetic variations by a number of techniques known to one of skill in the art. In one technique, oligonucleotides are arrayed on a gene chip for determining the DNA sequence of a by the sequencing by hybridization approach, such as that outlined in U.S. Pat. Nos. 6,025,136 and 6,018,041. The probes of the invention also can be used for fluorescent detection of a genetic sequence. Such techniques have been described, for example, in U.S. Pat. Nos. The probes of the invention also can be used for fluorescent detection of a genetic sequence. Such techniques have been described, for example, in U.S. Pat. Nos. 5,968,740 and 5,858,659. A probe also can be affixed to an electrode surface for the electrochemical detection of nucleic acid sequences such as described in U.S. Pat. No. 5,952,172 and by Kelley, S. O. et al. (1999) Nucl. Acids Res. 27:4830-4837. One or more probes for detecting the SNP of the invention (Table 2, 3, 4, 5 or 10, in particular Table 4) can be affixed to a chip and such a device used to predict response to HDL-raising or HDL mimicking agent, in particular CETP inhibitor/modulator and select an effective treatment for an individual with cardiovascular disease. It is conceivable that probes for detecting the SNP of the invention could be included on a chip with a variety of other probes for uses other than predicting response to a HDL-raising or HDL mimicking agent, in particular CETP inhibitor/modulator.

Additionally, synthetic oligonucleotides used as probes or primers may be modified to become more stable. Exemplary nucleic acid molecules which are modified include uncharged linkages such as phosphoramidate, phosphothioate and methylphosphonate analogs of DNA (see also U.S. Pat. Nos. 5,176,996; 5,264,564 and 5,256,775). Primers and probes of the invention can include for example, labeling methylation, inter-nucleotide modification such as pendent moieties (e.g., polypeitides), intercalators (e.g., acridine, psoralen), chelators, alkylators, and modified linkages (e.g., alpha anomeric nucleic acids). Also included are synthetic molecules that mimic nucleotide acid molecules in the ability to bind to a designated sequence by hydrogen bonding and other chemical interactions, including peptide linkages that substitute for phosphate linkages in the nucleotide backbone.

The invention relates to synthetic oligonucleotide molecules, primers and probes that hybridize under high stringency hybridization conditions to naturally occurring oligonucleotides described herein, gene markers of the ADCY9 gene. Oligonucleotides can be detected and/or isolated by specific hybridization, under high stringency conditions. "High stringency conditions" are known in the art and permit specific hybridization of a first oligonucleotide to a second oligonucleotide where there is a high degree of complimentarity between the first and second oligonucleotide. For the genotyping methods disclosed herein this degree of complimentarity is between 80% and 100% and preferably between 90% and 100%

The SNPs of the invention can also be detected from pre-existing data, such as whole genome sequence data present in a data base. The invention provides a computer implemented method of querying genomic data to determine a genotype for predicting the response of a patient to a CETP inhibitor and treating said patient accordingly i.e. treating responder patients with a CETP inhibitor.

Sample nucleic acid for use in the genotyping methods, treatment selection or methods of treatment can be obtained from any cell type or tissue of a subject. For example, a subject's bodily fluid, a sample, (e.g. blood) can be obtained by known techniques. Alternatively, nucleic acid tests can be performed on dry samples (e.g., hair or skin). More particularly, the sample nucleic acid for genotyping methods, treatment selection or methods of treatment will be obtained from blood cell type.

Figure 8:
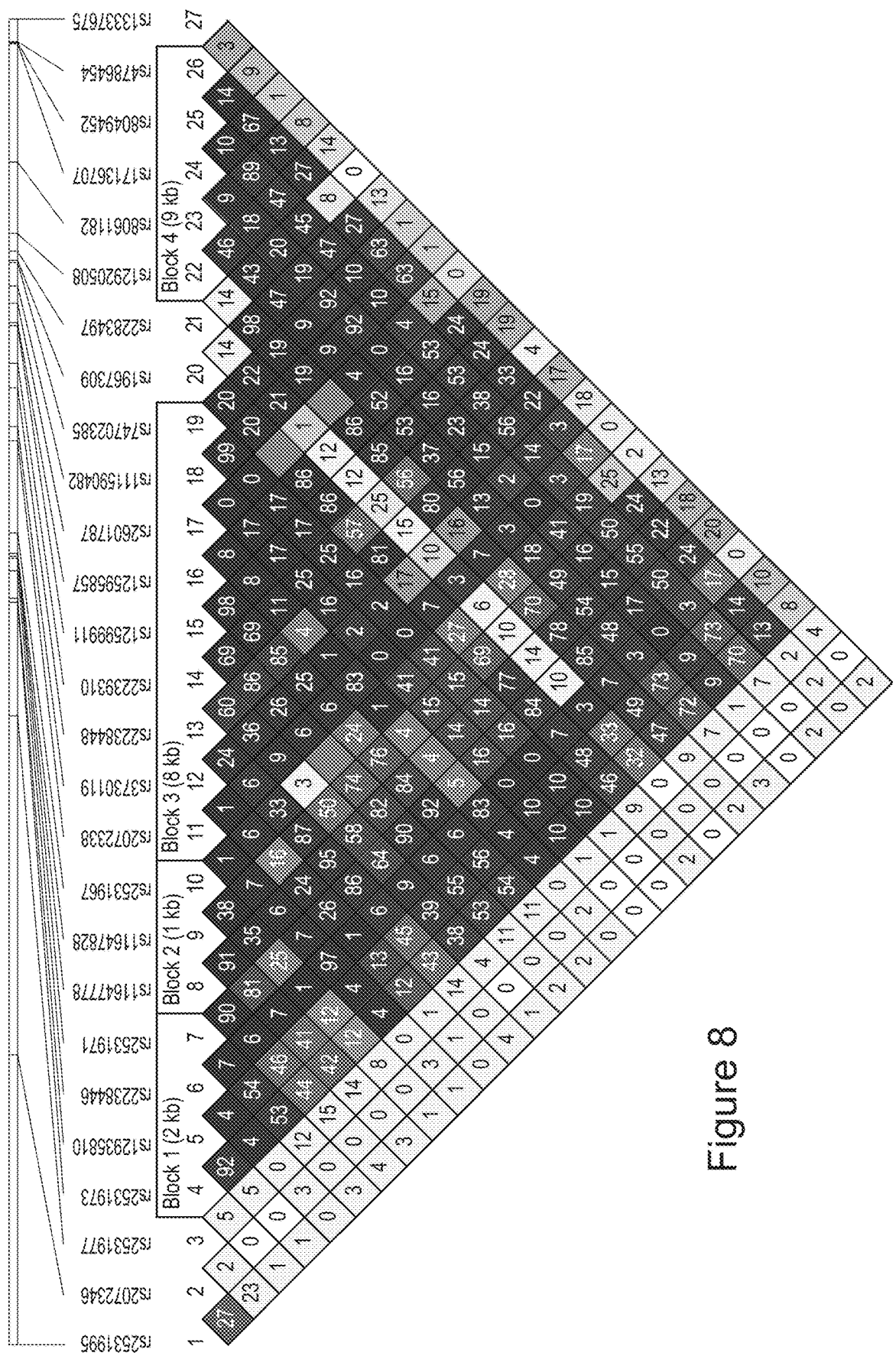
FIG. 8: Linkage disequilibrium of 27 genotyped SNPs in the ADCY9 gene showing $r^2$ values, linkage disequilibrium blocks calculated using the confidence interval method are shown in black and the D' statistic is shown in shades of red. Linkage disequilibrium in 5686 Caucasians from the dal-Outcomes study.
Figure 9:
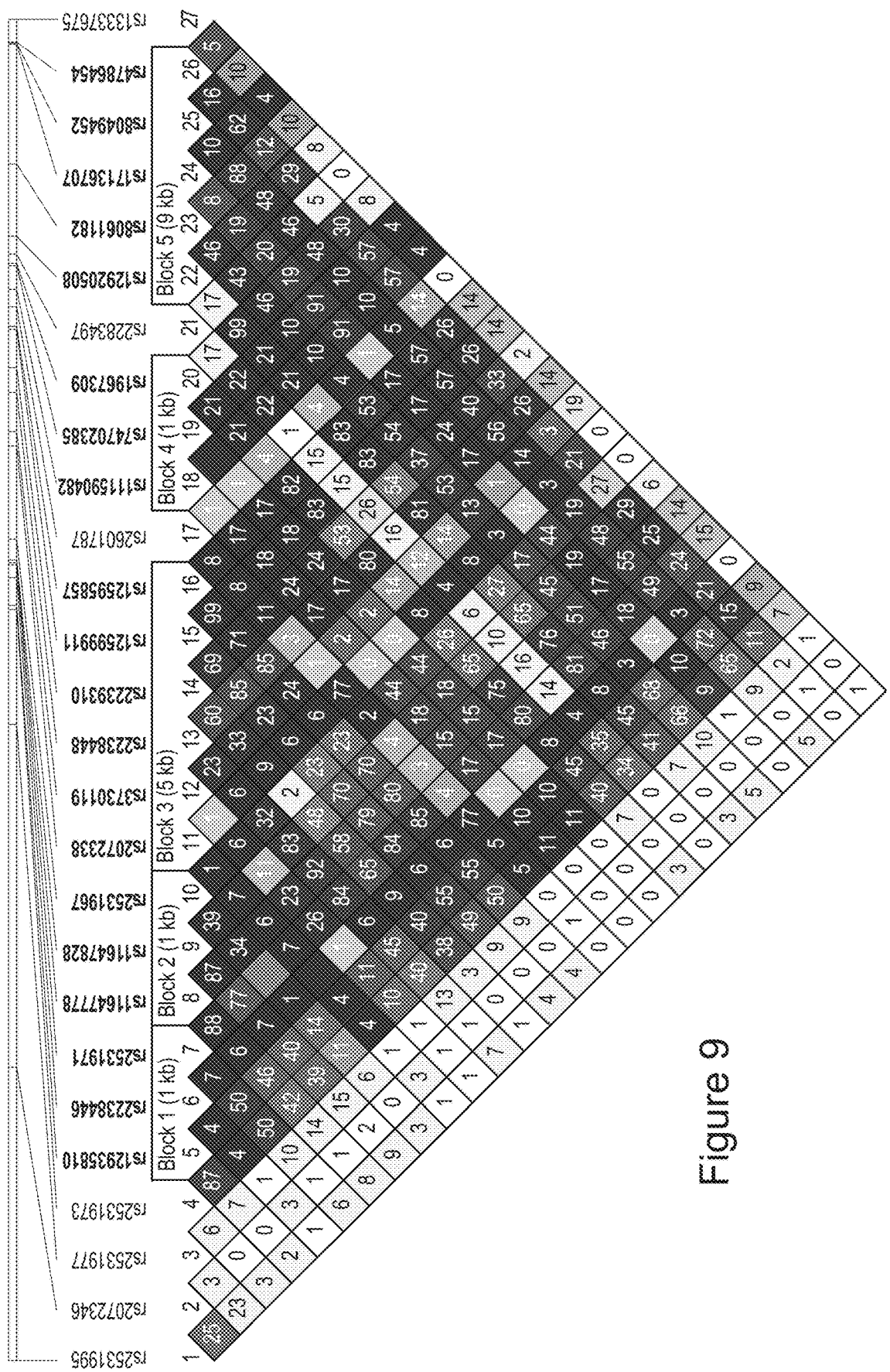
FIG. 9: Linkage disequilibrium of 27 genotyped SNPs in the ADCY9 gene showing $r^2$ values, linkage disequilibrium blocks calculated using the confidence interval method are shown in black and the D' statistic is shown in shades of red. Linkage disequilibrium in 386 participants of the dal-Plaque-2 study.

The invention described herein relates to methods and reagents useful for determining and identifying the allele present on the ADCY9 gene at rs11647778 and optionally rs1967309, rs2238448 or rs12595857, or any other genetic variant in linkage disequilibrium with these SNPs such as displayed in FIGS. 8 and 9, spanning from position chr16: 4049365 to chr16:4077178 (assembly GRCh37/hg19). In particular the invention also relates to methods and reagents for determining and identifying the allele present in the ADCY9 gene at rs11647778 and optionally rs1967309, rs12595857, rs2239310, rs11647828, rs8049452, rs12935810, rs74702385, rs17136707, rs8061182, rs111590482, rs4786454, rs2283497, rs2531967, rs3730119, rs13337675, rs2238448 more particularly at rs11647778 and optionally rs1967309 and/or rs12595857, and most particularly at rs11647778 and optionally rs1967309.

As set forth herein, the invention also provides treatment selection methods comprising detecting one or more genetic markers present in the ADCY9 gene. In some embodiments, the methods use probes or primers comprising nucleotide sequences which are complementary to a polymorphic region of ADCY9. Accordingly, the invention provides kits comprising probes and primers for performing the genotyping methods of the invention.

In some embodiments, the invention provides kits useful for determining whether a patient with a cardiovascular disorder has an increased likelihood of benefiting from treatment with a HDL-raising or HDL mimicking agent, in particular a CETP inhibitor/modulator. Such kits contain one of more of the reagents, in particular primers or probes, described herein and instructions for use. As an example only, the invention also provides kits useful for determining whether a patient with cardiovascular disorder has an increased likelihood of benefiting from treatment with thioisobutyric acid S-(2-{[1-(2-ethyl-butyl)-cyclohexanecarbonyl]-amino}-phenyl) ester comprising a first oligonucleotide and a second oligonucleotides specific for a CC polymorphism in the ADCY9 rs11647778 SNP and optionally for a AA polymorphism in the ADCY9 rs1967309 SNP.

The kits can comprise at least one probe or primer that is capable of specifically hybridizing to the polymorphic region of ADCY9 and instructions for use. The kits can comprise at least one of the above described nucleic acids. Kits useful for amplifying at least a portion of ADCY9 generally comprise two primers, at least one of which is capable of hybridizing to the allelic variant sequence. Such kits are suitable for detection of genotype by, for example, fluorescence detection, by electrochemical detection, or by other detection.

Yet other kits of the invention comprise at least one reagent useful to perform the assay. For example, the kit can comprise an enzyme. Alternatively the kit can comprise a buffer or any other useful reagent.

The kits can include all or some of the positive controls, negative controls, reagents, primers, sequencing markers, probes and antibodies described herein for determining the subject's genotype in the polymorphic region of ADCY9.

The following examples are intended merely to illustrate the practice of the present invention and are not provided by way of limitation.

The present invention refers to the following nucleotide and amino acid sequences:

The sequences provided herein are available in the NCBI database and can be retrieved from www.ncbi.nlm.nih.gov/sites/entrez?db=gene; Theses sequences also relate to annotated and modified sequences. The present invention also provides techniques and methods wherein homologous sequences, and variants of the concise sequences provided herein are used. Preferably, such "variants" are genetic variants. ON NCB1 database the Nucleotide sequence encoding *Homo sapiens* Adenylate Cyclase Type 9 (ACDY9) is available.

*Homo sapiens* Adenylate Cyclase Type 9 (ADCY9), RefSeqGene on chromosome 16 NCBI Reference Sequence: NCBI accession number NG_011434.1

*Homo sapiens* chromosome 16 genomic contig, GRCh37.p10 Primary Assembly NCBI Reference Sequence: NCBI accession number NT_010393.16

The intronic sequences for *Homo sapiens* ACDY9 gene SNPs providing the "rs" designation, alleles and corresponding SEQ ID number designations is disclosed in Tables 6, 7 and 8. The polymorphisms are identified in bold and within bracket.

TABLE 6

| | | ACDY9 SNPs and respective intronic sequence | |
|---|---|---|---|
| SNP rs ID | SEQ. ID. NO.: | Intronic sequence[1] | HGVS Names |
| rs11647778 | 21 | GGACCTGCCTGGTG CTTTCTCAGAG[C/G] AGACTGAGGTTTGG GGTTTGCGGAA | NC_000016.10:g.4001379C > G NG_011434.1:g.119807G > C NM_001116.3:c.1884 + 5989G > C NT_010393.17:g.3991379C > G |

TABLE 6-continued

ACDY9 SNPs and respective intronic sequence

| SNP rs ID | SEQ. ID. NO.: | Intronic sequence[1] | HGVS Names |
|---|---|---|---|
| rs1967309 | 20 | TTAACCTATTTATTT CTTTCAACCCT[C/T] AGCCCAGATCCTAA CCTTCGGTAAG | NC_000016.9:g.4065583A > G NG_011434.1:g.105604T > C NM_001116.3:c.1694 - 802A > C NT_010393.16:g.4005583A > G |
| rs12595857 | 2 | CATTGATTTTAAAC CTCAACAACAGC[A/G] ATGTCTTTTATCA GCTTAATTTTAC | NC_000016.9:g.4062592G > A NG_011434.1:g.108595C > T NM_001116.3:c.1694-5033C > T NT_010393.16:g.4002592G > A |

[1]Source from NCBI Genome reference Build 37.3

TABLE 7

List of genetic variants in gene ADCY9 on chr16 which have provided evidence of association (P < 0.05) with response to treatment with dalcetrapib from the GWAS study with reference sequence from the genotyping chip used for the experiment (Illumina OMNI2.5S):

| Chr. | Position (GRCh37/ hg19) | SNPrs identifier (NCBI) | P value | Sequence[1,2] | SEQ. ID NO. |
|---|---|---|---|---|---|
| 16 | 4,065,583 | rs1967309 | 4.11E-08 | TTCATGCACCCA GCAGACTAAATG TTTACTGAGTAC TTACCGAAGGTT AGGATCTGGGCT [A/G]AGGGTTGA AAGAAATAAATA GGTTAAAAAAGA AAAAAAGCCACC TAGGTGACTTTC ACTC[1] | 1 |
| 16 | 4,062,592 | rs12595857 | 4.53E-07 | TTAATATGATTT CTTATATTCTTTC CTGGTTATCCAT TGATTTTAAACC TCAACAACAGC [A/G]ATGTCTTTT ATCAGCTTAATT TTACAAAGGCTA CAGAGAGGGGT GGGCATTTCCTA ATGG[2] | 2 |
| 16 | 4,060,661 | rs2239310 | 1.29E-06 | CCTGTGTGGAGC CCATTACCTGAA GAGGGGCCAAG AGGACAAGCAG GTATGACTATGG TC[A/G]GGCGTG CCAAGTCCCAGG ACAAGGAAGGA CGGGTGCTCCAG GAAGCACAGGA GGGGGCAT[2] | 3 |
| 16 | 4,051,513 | rs11647828 | 2.76E-06 | TACCGGATGGCA GTGAGCAGGGA GGCTCACCTGGA TCATTTGGTGAA GGTGGCATCTGC C[T/C]GGTTTGTC CACTGTGAAGTT CCTATTCCTACC CCGCCCCCCACC TTTCTTTTTTGAG ATG[2] | 4 |

TABLE 7-continued

List of genetic variants in gene ADCY9 on chr16 which have provided evidence of association (P < 0.05) with response to treatment with dalcetrapib from the GWAS study with reference sequence from the genotyping chip used for the experiment (Illumina OMNI2.5S):

| Chr. | Position (GRCh37/ hg19) | SNPrs identifier (NCBI) | P value | Sequence[1,2] | SEQ. ID NO. |
|---|---|---|---|---|---|
| 16 | 4,076,094 | rs8049452 | 6.63E-06 | ACTTAACTATTT GTTGGGTGAATA TAGAAATGAATG AATGAATGGATG GATGAGCAGATA [T/C]ATCAAGAA GTTAATTCACAA ATTAAAGCCCAT TATGAAACTAAA GTAGAGGCTGGG CGCG[1] | 5 |
| 16 | 4,049,365 | rs12935810 | 2.98E-05 | ACCCGTGAACAA GTCGGGCCCCCA TCCACGCAATAT CTGCAGTCTCGA CTGTATGATCTC [A/G]TCCTTTGCA GCCACACTGTGA GGCAGCAATGAT CATTCCGCAGAC GGCCACAGACTC CAG[2] | 6 |
| 16 | 4,065,495 | rs74702385 | 8.87E-05 | GACGACACCCAG CACACCCAGCAC ACCCAGCACACC AGCGAACAGCCC ACCAGGTGCTAT [T/C]GCTGTCATT CATTTGCTCATT CGCTCGTTCATG CACCCAGCAGAC TAAATGTTTACT GAG[1] | 7 |
| 16 | 4,076,047 | rs17136707 | 9.11E-05 | AAAACAGTGCTC CAAAGGCAAAG AAATAGCAAAG ACAGAAGTAAG GCACTTAACTAT TTG[T/C]TGGGTG AATATAGAAATG AATGAATGAATG GATGGATGAGCA GATACATCAAGA AGTTAA[1] | 8 |
| 16 | 4,070,333 | rs8061182 | 1.51E-04 | GGCAGCTATGTA GGAAGCAGTGA AGATCCACATCC TTCCTTATTGGT GAAAGGAATGA AT[T/C]GGAAAC AGAAAGTTCTTT TTTACCTTTATTA AATAAACGTGAA GTCATAAGAACT ACTAA[2] | 9 |
| 16 | 4,064,368 | rs111590482 | 1.64E-04 | AGACTTTGTCTC AAAAAAGAAAA AAAAAAAAAA GAAGTCCCAAAT AATAAAATATGA GA[T/C]GGATTT ATGGAAGAAAGT GAAAGAAACAA AGGGTAGGCACC TTGCCTGTTTAA TTTGATC[1] | 10 |

TABLE 7-continued

List of genetic variants in gene ADCY9 on chr16 which have provided evidence of association (P < 0.05) with response to treatment with dalcetrapib from the GWAS study with reference sequence from the genotyping chip used for the experiment (Illumina OMNI2.5S):

| Chr. | Position (GRCh37/ hg19) | SNPrs identifier (NCBI) | P value | Sequence[1,2] | SEQ. ID NO. |
|---|---|---|---|---|---|
| 16 | 4,076,136 | rs4786454 | 1.98E-04 | TGGATGGATGAG CAGATACATCAA GAAGTTAATTCA CAAATTAAAGCC CATTATGAAACT [A/G]AAGTAGAG GCTGGGCGCGGT GGATCACGCCTA TAATCCCAGCAC TTTGGGAGGTCA AGGC[2] | 11 |
| 16 | 4,066,061 | rs2283497 | 8.87E-04 | TGTGATATGATG GTCATATCATAG CACAGGGCTGTT GTGAGGATTAAA TGAGTTGATTCA [T/G]GTAAACAGG GACATCCGAAAA AGGGAAAGACG GTGCTTGTCCTG AGAACAGCTGTG AATG[1] | 12 |
| 16 | 4,052,486 | rs2531967 | 1.11E-03 | AGGTGAGTGGCC TTAAAGGGGAAG GAGAAACCTTTT GAAAGCAGGAC AGGTCCTCTCTG A[A/G]TCATCCCC GTATGGGTAAAT CTACATCACTAG CTTCATTACTGA CTGGTCCATGTA GAAA[1] | 13 |
| 16 | 4,057,603 | rs3730119 | 0.0108 | CAGGTATGTCTT CAAACCTATGAT GGATAAAAGTTA CAGTCAGCACAG ATTGAAAGCACC [A/G]TCTGTTGAA ACGCAGCTCCGT CTTGCTCTCTGG AGAGGACTCACT CCTGGAAAGTTG AGA[2] | 14 |
| 16 | 4,077,178 | rs13337675 | 0.0377 | TGTAACCAAGTA ACCAATGGTAAA CCTCTACAGGGT ATTAAGGCTCCA GAAAATTCTCTA [A/G]TCAGCCACT TGCTCCTGCTCG AGCCTGCTCCCA CTCCGTGGAGTG TACTTTCATTTCA GT[1] | 15 |

Chr: chromosome number; P value: for association with cardiovascular events (primary composite event or unanticipated coronary revascularization) in patients treated with the CETP inhibitor dalcetrapib; 1: Reference sequence from the 1000 Genomes public database, as presented in the ILLUMINA annotation file for the OMNI 2.5S Chip HumanOmni25Exome-8v1_A.csv; 2: Reference sequence from the dbSNP public database version 131 from NCBI, as presented in the ILLUMINA annotation file for the OMNI 2.5S Chip HumanOmni25Exome-8v_1A. csv.

TABLE 8

List of additional genetic variants in gene ADCY9 on chr16:

| Variation | Location[1] | Distance (bp) from a | r2[1] | D'[1] | Column[2] | HGV Names[2] | SEQ. ID NO. |
|---|---|---|---|---|---|---|---|
| rs12920508 | 16:4066891 | 1308 | 0.952954 | 1 | TTTGGGGTGACG AAAATGTAAAAT TA[C/G/T]GTTGT GGTGATGGTTGC ACAACACC | NC_000016.9:g.4066891 G > C<br>NC_000016.9:g.4066891 G > T<br>NG_011434.1:g.104296 C > A<br>NG_011434.1:g.104296 C > G<br>NM_001116.3:c.1694 - 9332C > A<br>NM_001116.3:c.1694 - 9332C > G<br>NT_010393.16:g.400689 1G > C<br>NT_010393.16:g.400689 1G > T | 16 |
| rs12599911 | 16:4062436 | 3147 | 0.908417 | 1 | GAATAACCACAC ACATGGACCCTG GG[G/T]TCCAAG TTCATTAGAATG GCTCTTT | NC_000016.9:g.4062436 G > T<br>NG_011434.1:g.108751 C > A<br>NM_001116.3:c.1694 - 4877C > A<br>NT_010393.16:g.400243 6G > T | 17 |
| rs2531971 | 16:4051261 | 14322 | 0.840627 | 0.973493 | AAGACAGAGGA ACCCCCATAGGC TGG[G/T]GGTGA GCAGGGGGCATG AGGGCTAA | NC_000016.9:g.4051261 C > A<br>NG_011434.1:g.119926 G > T<br>NM_001116.3:c.1884 + 6108G > T<br>NT_010393.16:g.399126 1C > A | 18 |
| rs2238448 | 16:4059439 | 6144 | 0.840582 | 0.973467 | TGTCCAACTATT TCTTTCTTTCTTT T[C/T]TGAGATGG GGGTCTCACTGT GTTGG | NC_000016.9:g.4059439 T > C<br>NG_011434.1:g.111748 A > G<br>NM_001116.3:c.1694 - 1880A > G<br>NT_010393.16:g.399943 9T > C | 19 |

References:
a. rs1967309
[1]Location r2 and D' values from the 1000 Genomes public database
[2]Reference sequence &HGV Names from the dbSNP public database version 137 from NCBI Example 1

Dal-OUTCOMES trial (NC20971) was a double blind, randomized, placebo-controlled, parallel group, multi-center, phase III study to assess the safety and efficacy of the CETP inhibitor dalcetrapib in patients recently hospitalized for an Acute Coronary Syndrome (ACS). At time of the interim analysis the study included 15871 randomized patients, distributed over two treatment arms: placebo (7933 patients) and dalcetrapib (600 mg daily; 7938 patients). The study has shown no evidence of reduction of the event rate in the primary efficacy endpoint in the dalcetrapib arm compared to the placebo arm. The dal-OUTCOMES study details can be found in G. Schwartz et al., N. Engl. J. Med. 367; 22, 2012.

dal-Outcomes patients were recruited 4 to 12 weeks following hospitalization for acute coronary syndrome characterized by elevated cardiac biomarkers, with symptoms of acute myocardial ischemia, ischemic electrocardiographic abnormalities that were new or presumed to be new, or loss of viable myocardium on imaging. Patients without elevated cardiac biomarkers were eligible to participate if symptoms of acute myocardial ischemia were accompanied by electrocardiographic changes that were new or presumed to be new and by additional evidence of obstructive coronary disease. (Schwartz G G et al. Am Heart J 2009; 158:896-901 e3). Patients who had a myocardial infarction associated with percutaneous coronary intervention were also eligible. All patients were following individualized programs to target LDL cholesterol levels of 100 mg per deciliter (2.6 mmol per liter) or lower by statin if tolerated and diet. No specific statin agent was specified, and patients were not excluded based on LDL cholesterol values. Patients with serum triglyceride levels of 400 mg per deciliter (4.5 mmol per liter) or higher were excluded. (Schwartz G G et al. N Engl J Med 2012; 367:2089-99) Eligible participants to the dal-Outcomes trial entered a single-blind placebo run-in period of approximately 4 to 6 weeks to allow for patients to stabilise and for completion of planned revascularisation procedures. At the end of the run-in period, eligible patients in stable condition were randomised in a 1:1 ratio to 600 mg of dalcetrapib or placebo on top of evidence-based medical care for acute coronary syndrome. Cardiovascular events were adjudicated by an independent clinical endpoint committee. For the pharmacogenomics study, 6338 patients were recruited from April 2008 through July 2010 at 461 sites in 14 countries and provided written informed consent to participate to the genetic study of the dal-OUTCOMES trial. DNA was extracted from whole blood. Following genomic data cleanup, samples from 5749 Caucasian patients were used for the discovery genome-wide association study (GWAS).

Genotyping

The Illumina Infinium HumanOmni2.5Exome-8v1_A BeadChip including 2,567,845 genetic variants (Illumina, San Diego, Calif.) was used for the discovery GWAS of 5749 Caucasian participants to the dal-OUTCOMES study. The chromosome 16 region including 5 genes upstream and downstream of the adenylate cyclase type 9 (ADCY9) gene (CHR16: 3,400,000-4,600,000) was imputed using IMPUTE2, providing 17,764 variants for analysis with an average completion rate of 99.76%. A Sequenom panel was used for the confirmation of imputed single nucleotide polymorphisms (SNPs) in the ADCY9 gene identified in dal-OUTCOMES and were tested in the dal-PLAQUE-2 study, including 20 SNPs with P values <0.05 from the discovery GWAS.

DNA was extracted from 1 ml of whole blood using the QiaSymphony DNA midi kit version 1.1 (Qiagen, Garstilgweg, Switzerland) and quantified using the Quanti-Fluor™ dsDNA System (Promega, Madison, Wis.) with an average concentration of 91.5 ng/µL and average yield of 18.3 µg. 97.9% of DNA samples had concentrations above 25 ng/µL. Agarose gel electrophoresis confirmed high quality of DNA with no signs of degradation. DNA was normalized to 50 ng/µL.

Genome-Wide Association Study (GWAS)—

Genome-wide genotyping was performed using 200 ng of genomic DNA in GLP-environment at the Beaulieu-Saucier Pharmacogenomics Centre (Montreal, Canada). The Illumina Infinium HumanOmni2.5Exome-8v1_A BeadChip (Illumina, San Diego, Calif.) including 2,567,845 genomic markers was used and processed according to the manufacturer's specifications. This chip includes over 200,000 exome variants identified through the Exome Chip Consortium. The remaining BeadChip content is a mix of rare and common SNPs from the 1000 Genome Project designed to be maximally informative for diverse world populations. Each BeadChip was scanned and analyzed using the Illumina iScan Reader. Scanned images were analyzed using Illumina's GenomeStudio version 2011.1 with the GenTrain 2.0 cluster algorithm, using a No-Call threshold of 0.15, without manual cluster adjustment and using the manufacturer's Illumina HumanOmni25Exome-8v1_A cluster file. Genotype data files were produced in three installments of comparable size as data became available.

Sequenom—

A single Sequenom panel was designed and validated using HapMap DNA samples. The panel included 27 SNPs in the ADCY9 gene selected according to: a P value ≤0.05 in the discovery GWAS (n=15), a P value <$10^{-6}$ by imputation (n=6; 1 failed in development), predicted regulatory function (n=5; 1 excluded due to low MAF), or literature (n=4; 1 failed in production). The Sequenom MassArray Maldi-TOF System (Sequenom, La Jolla, Calif.) was used with Sequenom's Typer 4.0.22 Software. Each plate was clustered using autocluster and manually modified as needed. Two Coriell Institute DNA samples (NA11993 and NA07357) used as controls on each genotyping plate showed 100% concordance on all plate replicates and 100% concordance of genotype calls with expectations for corresponding SNPs in the 1000 Genomes and HapMap reference database. 17 SNPs genotyped on both the GWAS and Sequenom panel provided a mean genotypic concordance of 99.95% (min: 99.41, max: 100.00%), and 11 SNPs previously imputed provided a mean genotypic concordance with the most likely genotype (>0.80 imputation probability) of 99.75 (min: 98.48, max: 99.96).

Genomic Quality Checks

Dal-Outcomes Discovery GWAS.

Three genotyping files in PLINK format generated by GenomeStudio were combined and transformed to binary PLINK format. GenomeStudio Final report files were used to generate gender plots, LRR and BAF graphics. PyGen-Clean (Lemieux Perreault L P et al. *Bioinformatics* 2013; 29:1704-5) and PLINK version 1.07 were used for the quality checks (QC) and genetic data cleanup process. The genotyping experiment consisted of 68 plates of DNA samples. On each plate, there were two controls, one Coriell DNA alternating from four pre-selected samples (NA11993, NA11992, NA10860 and NA12763) and one internal DNA control from four pre-selected samples. The pairwise concordance of Coriell samples ranged from 0.999807 to 0.999958. Pairwise concordance of the four internal controls ranged from 0.99976 to 0.99995. The comparison of Coriell genotypes to expectation from the 1000 Genomes data provided concordance ranging from 0.996028 to 0.997783.

Figure 5:
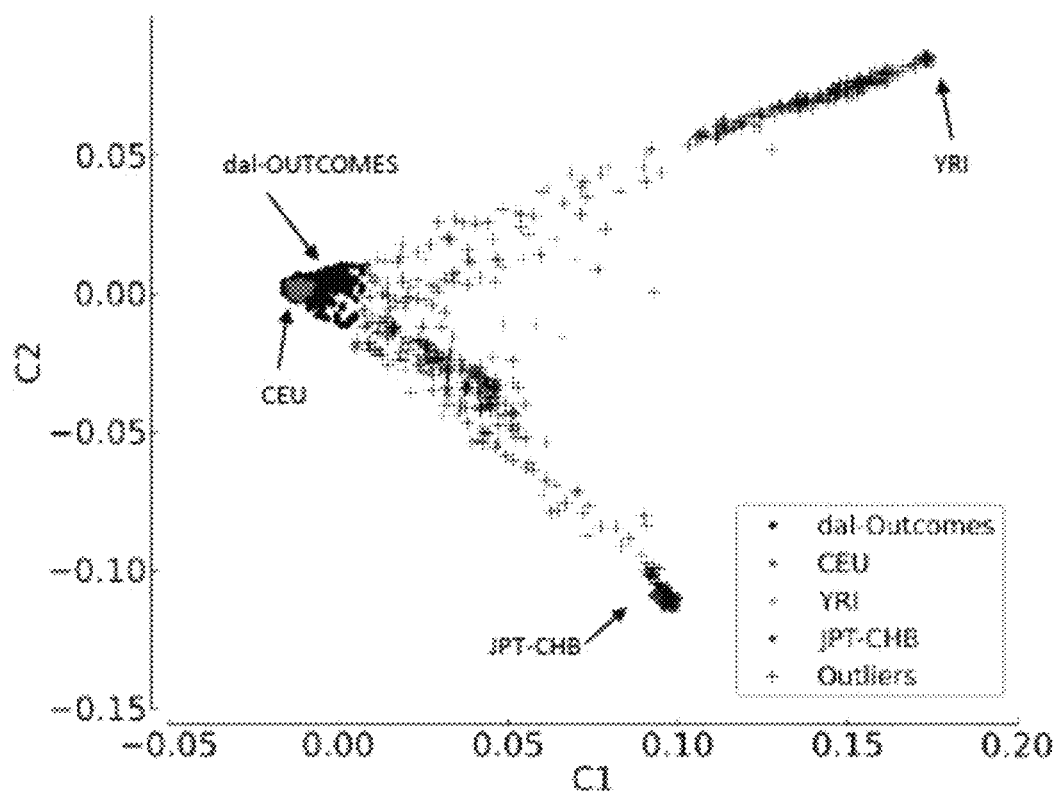
FIG. 5: Multi-dimensional scaling (MDS) plot showing the first two dimensions (C1, C2) from 76,854 SNPs for 6297 individuals from the genetic study of dal-Outcomes and 83 CEU founder, 186 JPT-CHB and 88 YRI founder from the 1000 genome data set. There were 436 ethnic outliers removed from the dataset (shown with +), and dal-Outcomes samples retained for analysis are shown.
Figure 6:
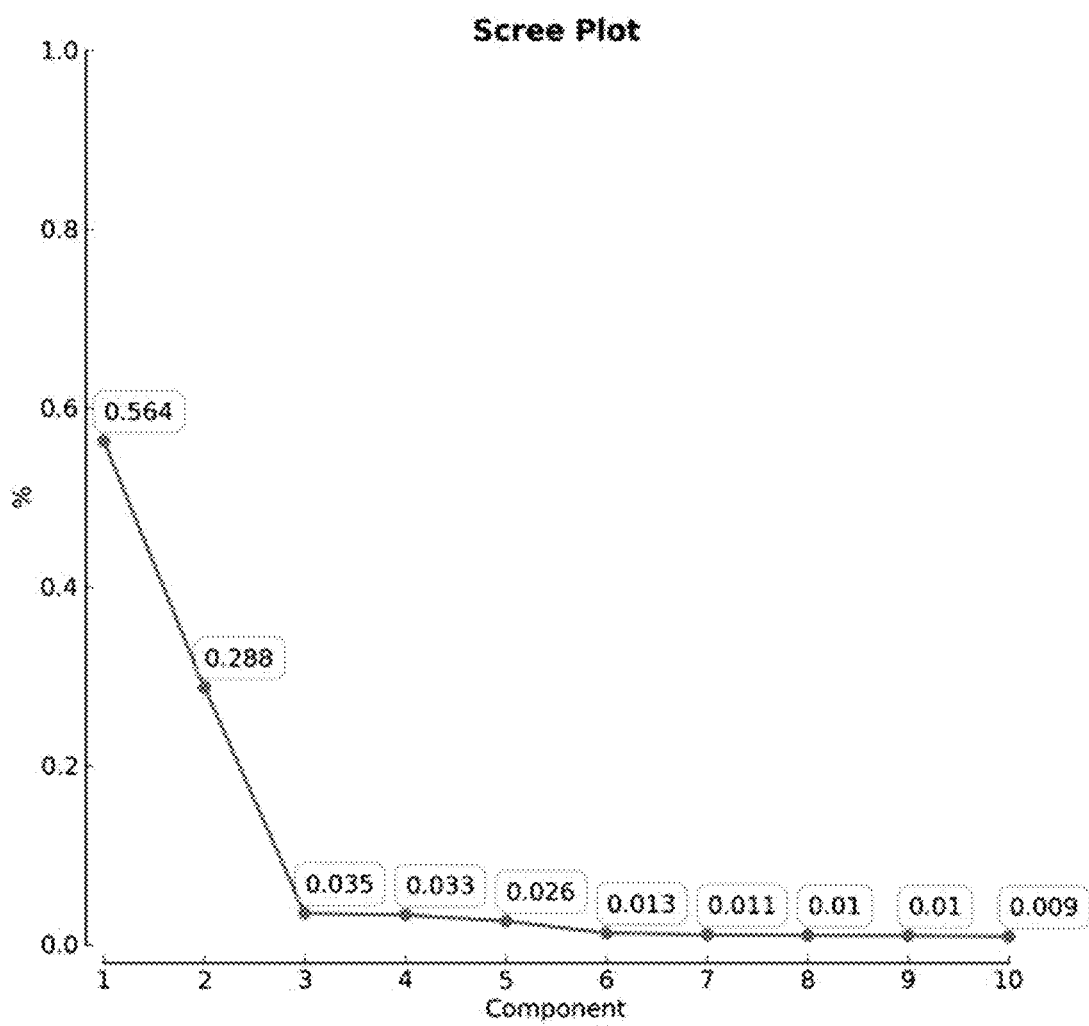
FIG. 6: Plot of the genomic variance explained by the first ten components from the principal component analysis from 76,854 SNPs for 6297 individuals from the genetic study of dal-Outcomes and 83 CEU founder, 186 JPT-CHB and 88 YRI founder from the 1000 genome data set.
Figure 7:
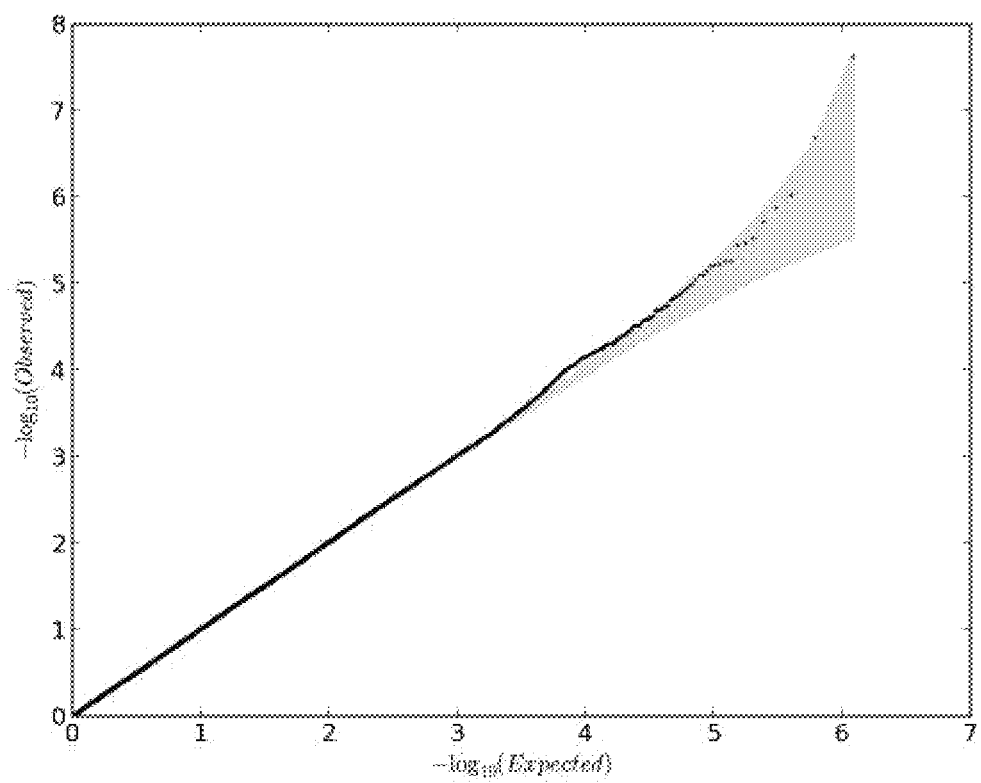
FIG. 7: Quantile-quantile (QQ) plot of observed $-\log_{10}$ (P values) versus the expectation under the null hypothesis for the genome-wide association of SNPs with MAF ≥0.05. The shaded region is the 95% concentration band formed by calculating the 2.5th and 97.5th percentiles of the distribution under the null hypothesis. Dots represent the ranked P values from the Cox proportional hazards model for time to occurrence of cardiovascular events of participants in the dalcetrapib arm and adjusted for sex and 5 principal components for genetic ancestry. The observed genomic inflation factor was 1.01.

Detailed genetic data cleanup steps are presented in Table 9. Duplicated SNPs were evaluated for concordance, completion rate, allele call and MAF. SNPs with different allele calls or different MAF were retained. Identical and concordant SNPs were merged. Genotyping completion rate for samples and SNPs was set to 98%. SNPs with genotyping plate bias (based on the 96 well plates used to dilute DNA samples) were flagged but not removed as the effect of genetic ancestry could not be excluded. Pairwise identity-by-state (IBD) was used to conduct close familial relationship checks. All but one pair-member of related pairs and sample duplicates (IBS2*ratio>0.80) were flagged and removed based on a selection of uncorrelated SNPs ($r^2$<0.1). The pairwise IBS matrix was used as a distance metric to identify cryptic relatedness among samples and sample outliers by multi-dimensional scaling (MDS). The first two MDS components of each subject were plotted including the genotypes of HapMap CEU, JPT-CHB, and YRI data (keeping only founder individuals). Outliers from the main Caucasian cluster were flagged and removed by k-nearest neighbour (FIG. 5). The scree plot and the cumulative explained variance were computed using the smartpca program of the EIGENSOFT suite (version 3.0). Options used were a numoutlieriter (maximum number of outlier removal iterations) of 0 (turned off) and altnormstyle (normalization formula) equal to NO. (Price A L Nat Genet 2006; 38:904-9) (FIG. 6)

Imputation

The chromosome 16 region including 5 genes upstream and downstream of ADCY9 (CHR16: 3,401,847-4,598,558; NCBI build GRCh37) was imputed using the programs IMPUTE2 (version 2.3.0) and GTOOL (version 0.7.0) on Linux with 1096 genotyped SNPs and 5749 dal-Outcomes Caucasian samples. (Howie B N et Al. PLoS Genet 2009; 5:e1000529) Strand alignment was solved by automatically flipping non A/T and C/G SNPs according to position. Ambiguous A/T and C/G SNPs were considered missing and were imputed. The Impute2 reference package ALL_1000G_phase1integrated_v3_chr16_impute was used for imputation. We used a cut-off of 0.80 for imputed genotype probabilities per genotype and per individual and a completion rate of 98% or higher. There remained 17,764 variants for analysis with an average completion rate of 99.76%.

Figure 10:
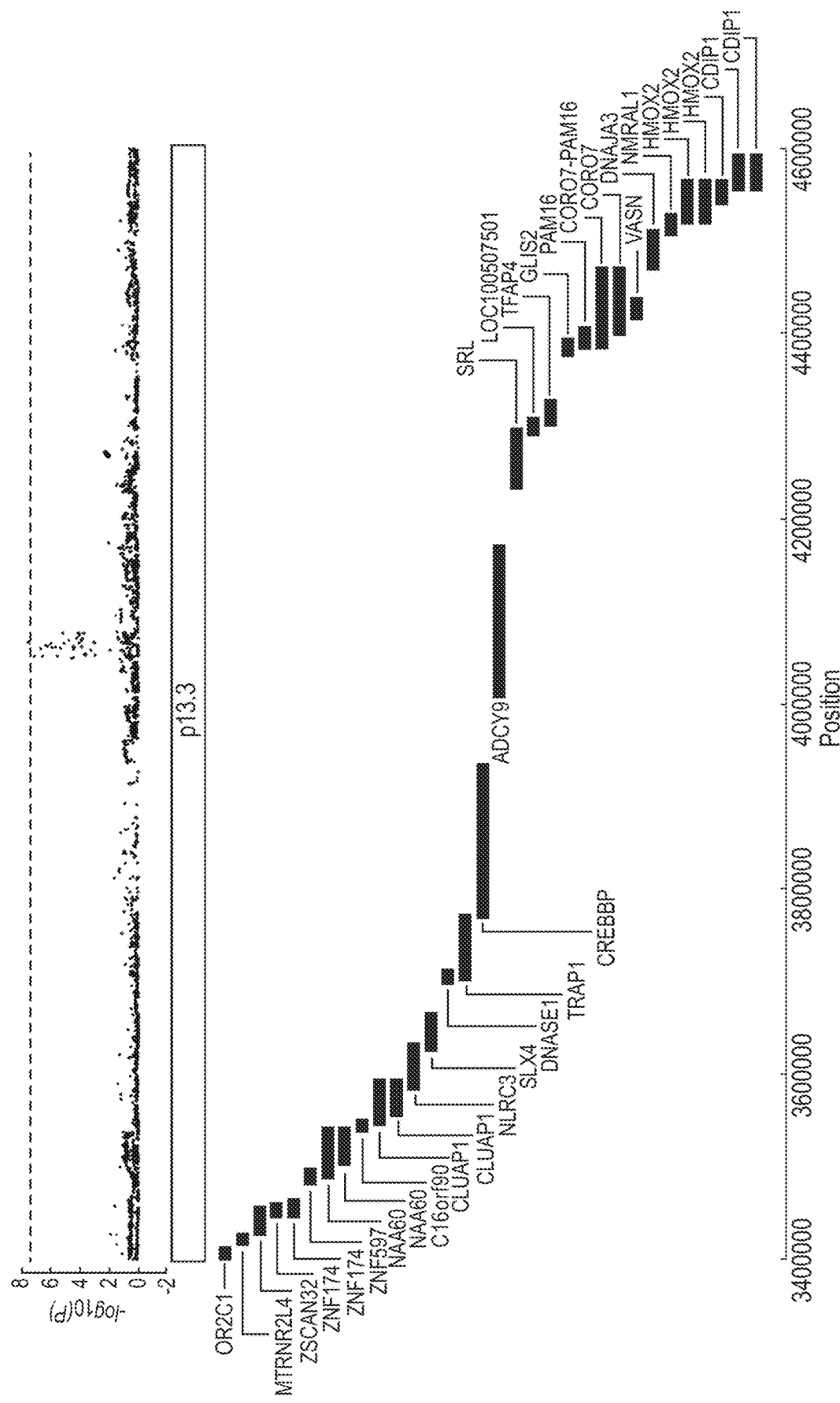
FIG. 10: Manhattan plot of association for genetic variants with events (primary composite endpoint) in the dal-Outcomes dalcetrapib arm, tested using dosage data of imputed SNPs within a logistic regression framework with PLINK software and adjusted for gender and 5 principal components for genetic ancestry.

Of 1,223,798 common SNPs analyzed, a single region with genome-wide significance was found to be associated with cardiovascular events by Cox proportional hazards modeling in the dalcetrapib arm, identifying a SNPs in the ADCY9 gene on chromosome 16: rs1967309 (P=$2.41 \times 10^{-8}$) (FIG. 1A). The genetic variant at this position has a minor allele frequency of 0.41, and the additive genetic effect of one allele (A) has a HR=0.65 (95% CI 0.56, 0.76) for cardiovascular events in the dalcetrapib arm (Table 12a). Neighbouring SNPs in linkage disequilibrium with rs1967309 and which provided lower, but supporting evidence for association were located in a common recombination block (FIG. 1B). Imputation in this region identified 9 additional SNPs in the ADCY9 gene with P<$10^{-5}$, including 6 with P<$10^{-6}$ (FIG. 10). None of the 835,255 rare SNPs analyzed in 36,268 SKAT gene sets passed the significance threshold for follow-up.

Figure 3:
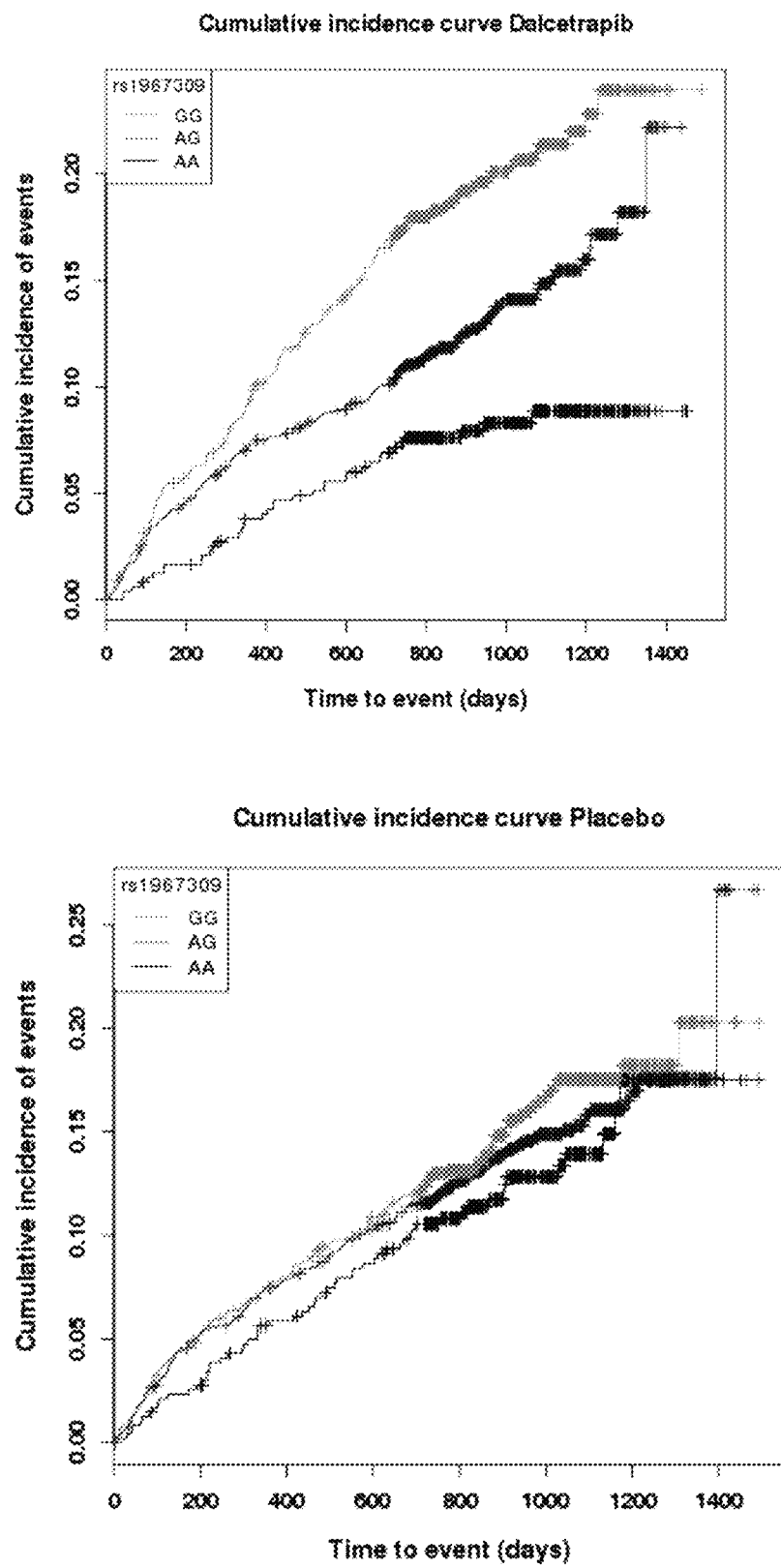
FIG. 3: Cumulative incidence of cardiovascular events (dal-OUTCOMES primary composite event or unanticipated coronary revascularization) for the dalcetrapib treatment arm and the placebo arm separately and stratified by the three genotypes at the rs1967309 SNP in the ADCY9 gene (GG, AG, AA).

There was no detectable genetic effect for rs1967309 in the placebo arm alone (Cox proportional-hazards, HR=0.92; P=0.25) (Table 12b). The gene-by-treatment arm interaction term was indicative of a statistical interaction (P=0.0014; beta: −0.340). Stratification by genotypes in the dalcetrapib arm shows that homozygotes for the minor allele (AA) and heterozygotes (AG) at rs1967309 have respectively HR=0.40 (95% CI 0.28, 0.57) and HR=0.68 (95% CI 0.55, 0.84) for cardiovascular events when compared to reference GG homozygotes (FIG. 3). Considering only patients with the homozygous genotype AA at rs1967309 (n=961), there was a 39% reduction in the pre-specified composite endpoint of coronary heart disease death, resuscitated cardiac arrest, non-fatal myocardial infarction, non-fatal ischemic stroke, unstable angina or unanticipated coronary revascularization with dalcetrapib compared to placebo (HR=0.61; 95% CI 0.41, 0.92). Similar results were observed when coronary revascularizations were removed from the primary endpoint (HR=0.60; 95% CI 0.35, 1.02). When considering only patients with the homozygous genotype GG at rs1967309 (n=1984), there was a 27% increase in cardiovascular events for treatment with dalcetrapib versus placebo (HR=1.27; 95% CI 1.02, 1.58). Heterozygous carriers had an intermediate response (n=2796; HR=0.94; 95% CI 0.77, 1.16). Results were confirmed by genotyping 27 SNPs in the ADCY9 gene by Sequenom technology (Table 10).

A total of eight polymorphisms (genotyped or imputed) were associated with P values less than $10^{-6}$ in the discovery cohort of 5749 patients from the pharmacogenomic study of the dal OUTCOMES trial, with the prespecified primary composite endpoint of coronary heart disease death, resuscitated cardiac arrest, non-fatal myocardial infarction, non-fatal ischemic stroke, unstable angina with objective evidence of ischemia or coronary revascularization. In this discovery genome-wide analysis, two of these eight SNPs in the ADCY9 gene were associated with P-values less than $5 \times 10^{-8}$. For the polymorphic nucleotide rs1967309, patients with the AA genotype (minor, or less common, allele) benefited from a reduction in cardiovascular events of 39% when treated with dalcetrapib compared to placebo, whereas those with the GG genotype (major allele) were exposed to a 27% increase in risk. Heterozygous patients with the AG genotype had an intermediate response. These results were only observed with dalcetrapib, not in the placebo arm, and there were statistical interactions between the polymorphisms and the study arm (dalcetrapib versus placebo) in the association with clinical events thus strengthening the link with the ADCY9 gene. Hazard ratios were similar when coronary revascularizations were removed from the analysis, which provided a direct comparison with the primary composite endpoint of the global dal-OUTCOMES trial (coronary heart disease, resuscitated cardiac arrest, non-fatal myocardial infarction, non-fatal ischemic stroke or unstable angina). All eight polymorphisms were in strong linkage disequilibrium ($r^2 > 0.77$), which reinforces the postulate that this region of the ADCY9 gene determines clinical responses to dalcetrapib.

Plasma LIPIDS

Figure 4:
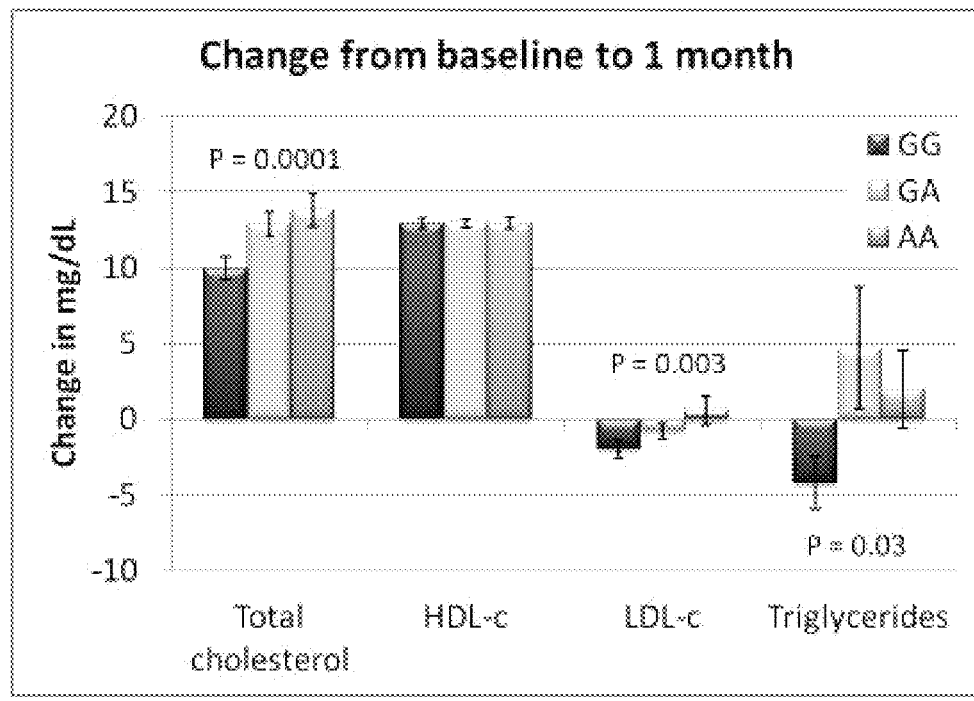
FIG. 4: Shows changes in lipid levels according to genotype during 24 months of dalcetrapib treatment. Panel A. Mean±SE (mg/dL) of change of lipid values from baseline to 1 month by genotype groups of the ADCY9 SNP rs1967309 for the dalcetrapib arm. P values are shown for univariate statistics between change in lipid and genotypes. Panel B. Mean±95% CI for absolute values of LDL-cholesterol during the follow up-period of the dal-Outcomes trial for patients in the dalcetrapib arm. P value for multivariate mixed regression model.
Figure 4:
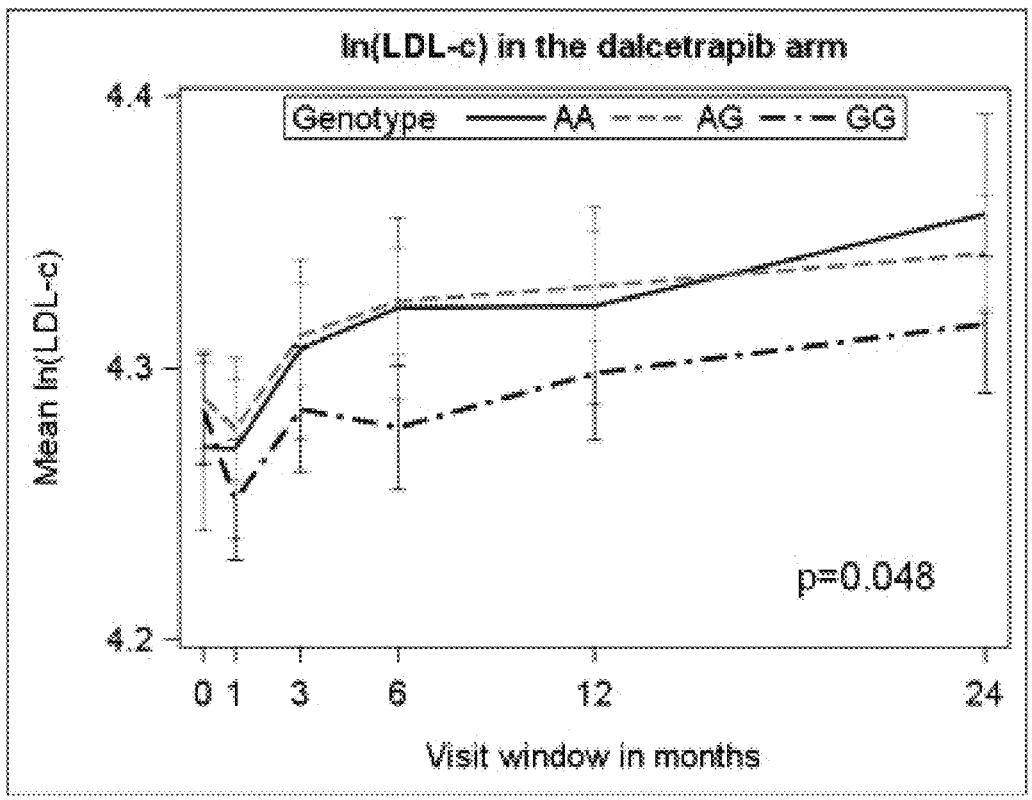

Genotypes of rs1967309 SNPs were significantly associated with changes over time in lipids induced by dalcetrapib in dal-OUTCOMES. Using univariate statistics, genotypes were associated with change in total cholesterol at 1 month (P=0.0001; P=0.004 when controlling for gender and genetic ancestry): GG genotype carriers had a smaller increase (10.0±23.3 mg/dl) compared to AG (12.9±30.3) and AA (13.8±24.0) carriers. This effect was not observed in the placebo arm. A similar result was observed for change in LDL-cholesterol after 1 month of dalcetrapib treatment: Changes were −2.0±20.0, −1.0±20.0 and +0.6±21.0 mg/dl in GG, AG and AA genotype carriers of rs1967309 respectively (P=0.003 univariate; adjusted P=0.006). During the dalcetrapib treatment period, GG carriers had overall slightly lower LDL-cholesterol levels (adjusted P=0.048; repeated measures analysis, FIG. 4).

TABLE 9

Summary information of the genetic data clean-up procedures performed prior to statistical analysis

| | | Procedure | |
|---|---|---|---|
| Clean-up step | N | SNP | IDs |
| Number of SNPs in genotyping file | 2,567,845 | | |
| Number of samples in genotyping file | 6,528 | | |
| SNPs without physical position removed | 6,913 | −6,913 | |
| Insertion/deletion variants removed | 169 | −169 | |
| Genotyping controls | | | |
| NA10860 | 17 | | |
| NA11992 | 17 | | −67 |
| NA11993 | 17 | | |
| NA12763 | 16 | | |
| Internal quality controls | 68 | | −68 |
| Samples destroyed due to duplicate ids | 68 | | −68 |
| Samples failed in lab | 25 | | −25 |
| Duplicate SNPs (by physical position) | 42,360 | | |
| Triplicate SNPs (by physical position) | 460 | | |
| Quadruplicate SNPs (by physical position) | 2 | | |
| Replicated SNPs merged (same alleles) | 42,722 | −42,722 | |
| Replicated SNPs not merged | 458 | | |
| Replicated SNPs with <98% concordance | 46 | −46 | |
| Samples with >10% missing genotypes | 3 | | −3 |
| SNPs with >2% missing genotypes | 46,542 | −46,542 | |
| Samples with >2% missing genotypes | 0 | | |
| SNPs with plate-bias P < $1 \cdot 10^{-7}$ | 275 | flagged | |
| SNPs used for IBS analysis | 77,689 | | |
| SNPs used for MDS analysis | 76,854 | | |
| No sex (missing from clinical file) | 64 | | |

TABLE 9-continued

Summary information of the genetic data clean-up procedures performed prior to statistical analysis

| Clean-up step | N | Procedure SNP IDs |
|---|---|---|
| Gender problem | 301 | |
| Related pairs | 16 | |
| Ethnicity other than Caucasian by MDS cluster | 436 | $-548^2$ |
| Internal QC controls | 12 | |
| Haploid genotypes (after gender issues processed) | 3,063,235 | Set to missing |
| SNPs with MAF = 0 | 408,652 | −408,652 |
| HWE test $2.46 \cdot 10^{-8} < P < 10^{-4}$ | 3,993 | flagged |
| HWE test $P < 2.46 \cdot 10^{-8}$ (0.05/2,062,801) | 3748 | −3,748 |
| Total number of SNPs for analysis | 2,059,053 | |
| Total number of samples for analysis | 5,749 | |

[1] One sample was identified as possible XO/XX mosaic and was removed from the analysis set.
[2] There were 10 samples having more than one reason for exclusion from the data set.

TABLE 10

Hazard Ratio (HR) for time to events (first occurrence of CHD death, MI, hospitalization for ACS, resuscitated cardiac arrest, atherothrombotic stroke or unanticipated coronary revascularization) on the dalcetrapib treatment arm versus the placebo arm stratified by genotypes of SNPs identified to be associated with cardiovascular events in the ADCY9 gene. Treatment effects of dalcetrapib versus placebo stratified by genotype for 20 validation SNPs genotyped in 5686 patients of the dal-Outcomes study population genotyped by Sequenom. MAF (minor allele frequency) and r2 were evaluated on all available individuals (n = 5686) NR = non-responsive; PR = partially responsive; R = responsive:

| SNP rs identifier | MAF | r² with rs1967309 | Genotype | N | Hazard ratio (dal vs placebo) | N patients with events | N patients without events | P value | Responsiveness to treatment | minor allele | major allele |
|---|---|---|---|---|---|---|---|---|---|---|---|
| rs1967309 | 0.4107 | 1 | GG | 1970 | 1.248 (1.002, 1.556) | 320 | 1650 | 0.048 | NR | A | G |
| | | | AG | 2761 | 0.953 (0.776, 1.172) | 362 | 2399 | 0.6498 | PR | | |
| | | | AA | 955 | 0.625 (0.415, 0.941) | 96 | 859 | 0.0242 | R | | |
| rs2531971 | 0.4341 | 0.849171 | CC | 1805 | 1.254 (0.997, 1.577) | 294 | 1511 | 0.0536 | NR | A | C |
| | | | AC | 2812 | 0.965 (0.787, 1.181) | 374 | 2438 | 0.727 | PR | | |
| | | | AA | 1057 | 0.660 (0.449, 0.968) | 108 | 949 | 0.0336 | R | | |
| rs2238448 | 0.4585 | 0.81182 | CC | 1659 | 1.291 (1.016, 1.641) | 271 | 1388 | 0.0364 | NR | T | C |
| | | | CT | 2830 | 0.974 (0.796, 1.192) | 377 | 2453 | 0.7984 | PR | | |
| | | | TT | 1188 | 0.657 (0.462, 0.934) | 128 | 1060 | 0.0192 | R | | |
| rs11647778 | 0.4586 | 0.778951 | GG | 1658 | 1.300 (1.023, 1.651) | 271 | 1387 | 0.0318 | NR | C | G |
| | | | CG | 2841 | 0.966 (0.79, 1.182) | 378 | 2463 | 0.7371 | PR | | |
| | | | CC | 1187 | 0.691 (0.488, 0.98) | 129 | 1058 | 0.038 | R | | |
| rs12599911 | 0.4442 | 0.869138 | TT | 1742 | 1.244 (0.984, 1.574) | 281 | 1461 | 0.068 | NR | G | T |
| | | | GT | 2832 | 0.982 (0.804, 1.200) | 384 | 2448 | 0.8609 | PR | | |
| | | | GG | 1108 | 0.672 (0.462, 0.98) | 112 | 996 | 0.0388 | R | | |
| rs12595857 | 0.4467 | 0.861475 | AA | 1730 | 1.255 (0.992, 1.586) | 281 | 1449 | 0.0584 | NR | G | A |
| | | | AG | 2828 | 0.954 (0.780, 1.167) | 379 | 2449 | 0.6469 | PR | | |
| | | | GG | 1124 | 0.719 (0.499, 1.038) | 117 | 1007 | 0.078 | R | | |
| rs12920508 | 0.4123 | 0.985041 | CC | 1891 | 1.205 (0.964, 1.506) | 310 | 1581 | 0.1016 | NR | G | C |
| | | | CG | 2672 | 0.946 (0.766, 1.169) | 345 | 2327 | 0.6072 | PR | | |
| | | | GG | 928 | 0.676 (0.451, 1.014) | 96 | 832 | 0.0585 | R | | |
| rs11647828 | 0.4378 | 0.696167 | TT | 1786 | 1.315 (1.04, 1.663) | 281 | 1505 | 0.0224 | NR | C | T |
| | | | CT | 2820 | 0.963 (0.788, 1.177) | 381 | 2439 | 0.7121 | PR | | |
| | | | CC | 1079 | 0.647 (0.447, 0.936) | 116 | 963 | 0.0209 | R | | |
| rs2239310 | 0.3613 | 0.567866 | AA | 2303 | 1.150 (0.937, 1.413) | 365 | 1938 | 0.1814 | NR | G | A |
| | | | AG | 2657 | 0.971 (0.785, 1.201) | 340 | 2317 | 0.7858 | PR | | |
| | | | GG | 726 | 0.623 (0.388, 0.998) | 73 | 653 | 0.049 | R | | |
| rs8049452 | 0.418 | 0.466547 | CC | 1909 | 0.804 (0.622, 1.041) | 234 | 1675 | 0.0978 | R | T | C |
| | | | CT | 2798 | 0.971 (0.794, 1.187) | 380 | 2418 | 0.771 | PR | | |
| | | | TT | 977 | 1.543 (1.13, 2.106) | 164 | 813 | 0.0064 | NR | | |
| rs12935810 | 0.4297 | 0.485354 | GG | 1830 | 0.796 (0.612, 1.036) | 224 | 1606 | 0.0898 | R | A | G |
| | | | AG | 2826 | 1.043 (0.853, 1.276) | 379 | 2447 | 0.6802 | NR | | |
| | | | AA | 1030 | 1.260 (0.935, 1.697) | 175 | 855 | 0.1286 | NR | | |
| rs111590482 | 0.1254 | 0.210392 | TT | 4348 | 1.054 (0.902, 1.231) | 637 | 3711 | 0.5095 | NR | C | T |
| | | | CT | 1250 | 0.856 (0.612, 1.198) | 137 | 1113 | 0.3643 | R | | |
| | | | CC | 88 | 0.333 (0.035, 3.205) | 4 | 84 | 0.3414 | R | | |
| rs74702385 | 0.1251 | 0.210876 | CC | 4351 | 1.053 (0.902, 1.23) | 639 | 3712 | 0.5147 | NR | T | C |
| | | | CT | 1247 | 0.854 (0.609, 1.197) | 135 | 1112 | 0.3593 | R | | |
| | | | TT | 88 | 0.348 (0.036, 3.348) | 4 | 84 | 0.3608 | R | | |
| rs8061182 | 0.4052 | 0.467552 | TT | 1996 | 0.815 (0.636, 1.044) | 252 | 1744 | 0.1055 | R | C | T |
| | | | CT | 2772 | 0.99 (0.809, 1.212) | 378 | 2394 | 0.9247 | PR | | |
| | | | CC | 918 | 1.52 (1.095, 2.11) | 148 | 770 | 0.0124 | NR | | |
| rs17136707 | 0.1214 | 0.19852 | TT | 4356 | 1.058 (0.906, 1.235) | 638 | 3718 | 0.4791 | NR | C | T |
| | | | CT | 1216 | 0.835 (0.592, 1.177) | 131 | 1085 | 0.3031 | PR | | |
| | | | CC | 78 | 0.552 (0.05, 6.096) | 3 | 75 | 0.6281 | R | A | G |

TABLE 10-continued

Hazard Ratio (HR) fortime to events (first occurrence of CHD death, MI, hospitalization for ACS, resuscitated cardiac arrest, atherothrombotic stroke or unanticipated coronary revascularization) on the dalcetrapib treatment arm versus the placebo arm stratified by genotypes of SNPs identified to be associated with cardiovascular events in the ADCY9 gene. Treatment effects of dalcetrapib versus placebo stratified by genotype for 20 validation SNPs genotyped in 5686 patients of the dal-Outcomes study population genotyped by Sequenom. MAF (minor allele frequency) and r2 were evaluated on all available individuals (n = 5686) NR = non-responsive; PR = partially responsive; R = responsive:

| SNP rs identifier | MAF | $r^2$ with rs1967309 | Genotype | N | Hazard ratio (dal vs placebo) | N patients with events | N patients without events | P value | Responsiveness to treatment | minor allele | major allele |
|---|---|---|---|---|---|---|---|---|---|---|---|
| rs4786454 | 0.1675 | 0.280233 | GG | 3931 | 1.062 (0.903, 1.25) | 582 | 3349 | 0.4677 | NR | | |
| | | | AG | 1579 | 0.91 (0.68, 1.217) | 182 | 1397 | 0.5231 | PR | | |
| | | | AA | 160 | 0.573 (0.187, 1.751) | 13 | 147 | 0.3285 | R | | |
| rs2531967 | 0.2314 | 0.28616 | GG | 3374 | 1.121 (0.94, 1.337) | 496 | 2878 | 0.2046 | NR | A | G |
| | | | AG | 1992 | 0.855 (0.668, 1.094) | 253 | 1739 | 0.2132 | PR | | |
| | | | AA | 320 | 0.786 (0.379, 1.63) | 29 | 291 | 0.5176 | R | | |
| rs2283497 | 0.3934 | 0.146627 | GG | 2081 | 1.226 (0.977, 1.538) | 301 | 1780 | 0.0781 | NR | T | G |
| | | | GT | 2735 | 0.999 (0.815, 1.224) | 372 | 2363 | 0.9926 | PR | | |
| | | | TT | 869 | 0.581 (0.39, 0.864) | 105 | 764 | 0.0074 | R | | |
| rs3730119 | 0.1766 | 0.16273 | GG | 3776 | 1.059 (0.894, 1.254) | 539 | 3237 | 0.5058 | NR | A | G |
| | | | AG | 1657 | 0.887 (0.676, 1.165) | 209 | 1448 | 0.3891 | PR | | |
| | | | AA | 159 | 0.472 (0.177, 1.259) | 18 | 141 | 0.1337 | R | | |
| rs13337675 | 0.247 | 0.141651 | AA | 3221 | 1.070 (0.891, 1.284) | 462 | 2759 | 0.4703 | NR | G | A |
| | | | AG | 2121 | 0.904 (0.715, 1.143) | 280 | 1841 | 0.3996 | PR | | |
| | | | GG | 344 | 1.034 (0.537, 1.989) | 36 | 308 | 0.9206 | PR | | |

TABLE 11 r2 value between all SNPs based on 5686 from the dal-Outcomes study.

| | rs-12935810 | rs-2531971 | rs-11647778 | rs-11647828 | rs2531967 | rs3730119 | rs2238448 | rs2239310 | rs12599911 | rs12595857 |
|---|---|---|---|---|---|---|---|---|---|---|
| rs12935810 | | 0.5390 | 0.4591 | 0.4143 | 0.1347 | 0.1255 | 0.4525 | 0.3865 | 0.5501 | 0.5586 |
| rs2531971 | | | 0.9026 | 0.8171 | 0.2639 | 0.2567 | 0.8608 | 0.6398 | 0.9073 | 0.9211 |
| rs11647778 | | | | 0.9121 | 0.3619 | 0.2324 | 0.9549 | 0.5764 | 0.8302 | 0.8410 |
| rs11647828 | | | | | 0.3900 | 0.1521 | 0.8722 | 0.4991 | 0.7502 | 0.7616 |
| rs2531967 | | | | | | 0.0607 | 0.3462 | 0.0384 | 0.2456 | 0.2523 |
| rs3730119 | | | | | | | 0.2316 | 0.3572 | 0.2461 | 0.2453 |
| rs2238448 | | | | | | | | 0.6011 | 0.8658 | 0.8589 |
| rs2239310 | | | | | | | | | 0.6925 | 0.6903 |
| rs12599911 | | | | | | | | | | 0.9850 |
| rs12595857 | | | | | | | | | | |
| rs111590482 | | | | | | | | | | |
| rs74702385 | | | | | | | | | | |
| rs1967309 | | | | | | | | | | |
| rs2283497 | | | | | | | | | | |
| rs12920508 | | | | | | | | | | |
| rs8061182 | | | | | | | | | | |
| rs17136707 | | | | | | | | | | |
| rs8049452 | | | | | | | | | | |
| rs4786454 | | | | | | | | | | |
| rs13337675 | | | | | | | | | | |

| | rs-111590482 | rs-74702385 | rs-1967309 | rs-2283497 | rs12920508 | rs8061182 | rs17136707 | rs8049452 | rs4786454 | rs13337675 |
|---|---|---|---|---|---|---|---|---|---|---|
| rs12935810 | 0.1083 | 0.1082 | 0.4854 | 0.3331 | 0.4907 | 0.7364 | 0.1022 | 0.7381 | 0.1415 | 0.1009 |
| rs2531971 | 0.1666 | 0.1666 | 0.8492 | 0.1037 | 0.8567 | 0.4836 | 0.1770 | 0.4975 | 0.2434 | 0.2067 |
| rs11647778 | 0.1514 | 0.1511 | 0.7790 | 0.1412 | 0.7842 | 0.5336 | 0.1633 | 0.5496 | 0.2280 | 0.1833 |
| rs11647828 | 0.1651 | 0.1647 | 0.6962 | 0.1078 | 0.7006 | 0.4903 | 0.1762 | 0.5042 | 0.2487 | 0.1293 |
| rs2531967 | 0.4159 | 0.4159 | 0.2862 | 0.0647 | 0.2906 | 0.1955 | 0.4198 | 0.2030 | 0.2530 | 0.0266 |
| rs3730119 | 0.0255 | 0.0256 | 0.1627 | 0.1032 | 0.1626 | 0.1248 | 0.0215 | 0.1296 | 0.0366 | 0.1796 |
| rs2238448 | 0.1734 | 0.1731 | 0.8118 | 0.1533 | 0.7994 | 0.5564 | 0.1670 | 0.5574 | 0.2309 | 0.1786 |
| rs2239310 | 0.2554 | 0.2541 | 0.5679 | 0.2531 | 0.5612 | 0.3668 | 0.2431 | 0.3772 | 0.3376 | 0.0497 |
| rs12599911 | 0.1851 | 0.1843 | 0.8691 | 0.1282 | 0.8585 | 0.5321 | 0.1757 | 0.5325 | 0.2455 | 0.1951 |
| rs12595857 | 0.1835 | 0.1827 | 0.8615 | 0.1254 | 0.8681 | 0.5212 | 0.1738 | 0.5353 | 0.2431 | 0.1968 |
| rs111590482 | | 0.9944 | 0.2104 | 0.2224 | 0.2030 | 0.1049 | 0.9276 | 0.1066 | 0.6329 | 0.0156 |
| rs74702385 | | | 0.2109 | 0.2228 | 0.2033 | 0.1048 | 0.9283 | 0.1069 | 0.6337 | 0.0156 |
| rs1967309 | | | | 0.1466 | 0.9850 | 0.4676 | 0.1985 | 0.4665 | 0.2802 | 0.1417 |
| rs2283497 | | | | | 0.1410 | 0.4353 | 0.2132 | 0.4492 | 0.0877 | 0.0011 |
| rs12920508 | | | | | | 0.4601 | 0.1917 | 0.4725 | 0.2740 | 0.1463 |

TABLE 11 r2-continued value between all SNPs based on 5686 from the dal-Outcomes study.

| rs8061182 | | | | 0.1022 | 0.8910 | 0.1342 | 0.0834 |
|---|---|---|---|---|---|---|---|
| rs17136707 | | | | | 0.1086 | 0.6780 | 0.0151 |
| rs8049452 | | | | | | 0.1456 | 0.0959 |
| rs4786454 | | | | | | | 0.0323 |
| rs13337675 | | | | | | | |

TABLE 12

Results with $P < 5 \times 10^{-8}$ in the dal-OUTCOMES discovery genome-wide association study (GWAS)

| SNP | Genotype group | Patients with events | Patients without events | $\beta_g^1$ | $\beta_g$ P value[2] | HR (95% CI) |
|---|---|---|---|---|---|---|
| a. Cox proportional-hazards results in the dal-OUTCOMES alcetrapib arm (n = 2845) | | | | | | |
| rs1967309 | AA | 38 | 447 | −0.429 | $2.41 \times 10^{-8}$ | 0.651 (0.560, 0.757) |
| | AG | 176 | 1203 | | | |
| | GG | 176 | 802 | | | |
| b. Cox proportional-hazards results in the dal-OUTCOMES placebo arm (n = 2904) | | | | | | |
| rs1967309 | AA | 59 | 417 | −0.085 | 0.248 | 0.916 (0.793, 1.06) |
| | AG | 192 | 1225 | | | |
| | GG | 146 | 860 | | | |

[1]Estimate of the regression parameter for the additive genetic effect adjusted for gender and 5 principal components for genetic ancestry, and where homozygotes for the common allele are coded 0, heterozygotes 1, and homozygotes for the rare allele are coded 2;
[2]Likelihood ratio test of the genotype effect,
where $H_0: \beta_g = 0$;
HR: hazard ratio;
SNP: single nucleotide polymorphism.

Example 2

The dal-PLAQUE-2 study (Tardif J C et al, Circulation Cardiovascular imaging 2011; 4:319-33) was a phase 3b multicenter, double-blind, randomized, placebo-controlled, parallel group trial designed to evaluate the effect of dalcetrapib on atherosclerotic disease progression in patients with evidence of coronary artery disease and carotid intima media thickness of at least 0.65 mm in the far wall of the common carotid arteries, as assessed by B-mode ultrasonography. A total of 931 patients were randomized to receive dalcetrapib 600 mg daily or matching placebo with intended treatment duration of 24 months. However, the trial was terminated prematurely concurrent with the termination of dal OUTCOMES (the latter due to futility). Patients continued study medication until they returned for follow-up carotid imaging at 12 months. Carotid B-mode ultrasound recordings at baseline, month 6, and month 12 were analyzed centrally at the core laboratory of the Montreal Heart Institute. Intima-media thickness (IMT) was analyzed on the far wall of the common carotid arteries. A segment of 10 mm in length of the common carotid artery was analyzed on serial examinations using an automated edge detection software (Carotid Analyzer, Medical Imaging Applications, Coralville, Iowa). Among the 411 participants in the dal-PLAQUE-2 trial who consented to the genetic study, 386 had imaging measures at baseline, 6 months and 12 months (194 and 192 in the dalcetrapib and placebo arms respectively). DNA was extracted from whole blood. The research protocols were approved by the relevant institutional review boards or ethics committees and all human participants gave written informed consent.

Central Analysis of Carotid Imaging Examinations in the Dal-Plaque-2 Trial

All acquired carotid ultrasound recordings were analyzed at the core laboratory of the Montreal Heart Institute by experienced technicians supervised by a physician. Images were required to meet quality and inclusion and exclusion criteria for eligibility prior to random assignment to study treatment. The methods for carotid intima-media thickness analysis included side-by-side viewing of baseline and follow-up studies.

Carotid arterial wall segments were assessed in a longitudinal view, perpendicular to the ultrasound beam, with a horizontal display of the arterial image in order to view the interfaces between blood and vascular structures on the longest possible segment. The localization of the end of the common carotid artery was used as the landmark in repositioning and analyzing comparative length of segments in baseline and follow-up studies. Intima-media thickness was analyzed on the far wall of the right and left common carotid arteries, to reduce variability of measurements. The average of the mean intima-media thickness values of the right and left common carotid arteries was used. A matched segment of 10 mm in length of the common carotid artery was analyzed on serial examinations (baseline, 6 months and 12 months), starting 5 mm proximal to the carotid bifurcation. The edge detection software Carotid Analyzer (Medical Imaging Applications LLC, Coralville, Iowa) was used to analyze intima-media thickness using the automated option. Two sets of carotid artery borders were identified: First, the media-adventitia borders were determined and verified by the reader. When required, their locations were semi-automatically modified to the correct location. When these borders were approved, the lumen-intima boundaries were automatically detected using the media-adventitia borders for guidance. Frames from looped sequences of intima-media thickness were selected for reading, and poor quality outlier frames were removed from the analysis when required.

Of the 27 SNPs selected for genotyping by Sequenom, 20 SNPs in the ADCY9 gene had P<0.05 in the discovery cohort. We tested for association with those SNPs in the dal-PLAQUE-2 trial in order to obtain supporting evidence for association by relying on imaging data obtained after 6 and 12 months of treatment in the dalcetrapib arm (n=194). Ten out of 20 SNPs provided association with IMT measures in dal-PLAQUE-2 (P<0.05, Table 13). Notably, marker rs2238448 (which was in linkage disequilibrium with rs1967309 ($r^2$=0.80)) was associated with IMT in dal-plaque-2 (P=0.009) and with events in dal-OUTCOMES (P=8.88×10$^{-8}$; HR=0.67, 95% CI 0.58, 0.78). After 12 months of treatment with dalcetrapib, changes in IMT were −0.027±0.079 mm in homozygote carriers of the minor allele (TT), 0.000±0.048 mm for heterozygotes, and +0.009±0.038 mm for homozygous carriers of the common allele (CC) at rs2238448 (P=0.009). This effect emerged at 6 months. All 20 SNPs displayed a decrease in IMT in agreement with the genotype group that showed reduced cardiovascular risk in the dal-OUTCOMES trial (Table 13). None of the genotyped SNPs showed association in the placebo arm (all P>0.05). Only the gene-by-treatment interaction term of rs2531967 reached significance (P=0.024) in dal-PLAQUE-2, probably due to the small sample size. SNP rs1967309 did not reach significance in dal-PLAQUE-2 (P=0.114), but the reduction in IMT was of similar magnitude to that with rs2238448 and consistent with the findings in dal-OUTCOMES. After 12 months of treatment with dalcetrapib, changes in IMT were −0.021±0.083 mm in AA homozygotes, −0.001±0.048 mm for heterozygotes, and +0.005±0.042 mm for GG homozygotes at rs1967309.

TABLE 13

Change from baseline in carotid intima-media thickness after 6 and 12 months of dalcetrapib treatment. 20 SNPs with P < 0.05 in dal-OUTCOMES are shown with results for the dal-PLAQUE-2 study.

| | | | | dal-PLAQUE-2 | | | |
|---|---|---|---|---|---|---|---|
| | | | | Homozygotes for minor allele | | Heterozygotes | |
| SNP | Position[1] | MAF[2] | visit | N | Mean (±STD) mm | N | Mean (±STD) mm |
| rs1967309 | 16:4065583 | 0.411 | M06 | 30 | −0.005 (±0.058) | 99 | −0.003 (±0.040) |
| | | | M12 | 26 | −0.021 (±0.083) | 90 | −0.001 (±0.048) |
| rs2531971 | 16:4051261 | 0.434 | M06 | 28 | −0.010 (±0.065) | 109 | −0.002 (±0.040) |
| | | | M12 | 25 | −0.016 (±0.069) | 99 | 0.002 (±0.045) |
| rs2238448 | 16:4059439 | 0.459 | M06 | 32 | −0.010 (±0.061) | 111 | −0.003 (±0.040) |
| | | | M12 | 28 | −0.027 (±0.079) | 102 | 0.000 (±0.048) |
| rs11647778 | 16:4051380 | 0.459 | M06 | 34 | −0.013 (±0.062) | 109 | −0.002 (±0.039) |
| | | | M12 | 30 | −0.026 (±0.079) | 99 | 0.001 (±0.047) |
| rs12599911 | 16:4062436 | 0.444 | M06 | 35 | −0.008 (±0.068) | 108 | −0.003 (±0.036) |
| | | | M12 | 31 | −0.019 (±0.086) | 99 | −0.002 (±0.044) |
| rs12595857 | 16:4062592 | 0.447 | M06 | 36 | −0.008 (±0.067) | 107 | −0.003 (±0.036) |
| | | | M12 | 32 | −0.018 (±0.085) | 98 | −0.002 (±0.044) |
| rs12920508 | 16:4066891 | 0.42 | M06 | 30 | −0.005 (±0.058) | 99 | −0.003 (±0.040) |
| | | | M12 | 26 | −0.021 (±0.083) | 90 | −0.001 (±0.048) |
| rs2239310 | 16:4060661 | 0.361 | M06 | 22 | −0.001 (±0.070) | 98 | −0.004 (±0.041) |
| | | | M12 | 19 | −0.002 (±0.074) | 90 | −0.003 (±0.050) |
| rs11647828 | 16:4051513 | 0.438 | M06 | 29 | −0.018 (±0.050) | 106 | −0.002 (±0.045) |
| | | | M12 | 25 | −0.020 (±0.077) | 97 | −0.003 (±0.052) |
| rs8049452 | 16:4076094 | 0.418 | M06 | 31 | 0.020 (±0.049) | 97 | −0.002 (±0.035) |
| | | | M12 | 30 | 0.006 (±0.033) | 90 | 0.003 (±0.046) |
| rs12935810 | 16:4049365 | 0.43 | M06 | 30 | 0.021 (±0.050) | 91 | −0.003 (±0.035) |
| | | | M12 | 30 | 0.010 (±0.040) | 83 | −0.001 (±0.043) |
| rs8061182 | 16:4070333 | 0.405 | M06 | 30 | 0.016 (±0.050) | 94 | 0.000 (±0.035) |
| | | | M12 | 29 | −0.001 (±0.045) | 87 | 0.007 (±0.042) |
| rs74702385 | 16:4065495 | 0.125 | M06 | 3 | −0.015 (±0.035) | 46 | −0.006 (±0.039) |
| | | | M12 | 3 | −0.008 (±0.058) | 37 | −0.002 (±0.047) |
| rs17136707 | 16:4076047 | 0.121 | M06 | 3 | −0.015 (±0.035) | 46 | −0.006 (±0.038) |
| | | | M12 | 3 | −0.008 (±0.058) | 37 | −0.004 (±0.053) |
| rs111590482 | 16:4064368 | 0.125 | M06 | 3 | −0.015 (±0.035) | 46 | −0.006 (±0.039) |
| | | | M12 | 3 | −0.008 (±0.058) | 37 | −0.002 (±0.047) |
| rs4786454 | 16:4076136 | 0.168 | M06 | 8 | −0.020 (±0.046) | 59 | −0.007 (±0.040) |
| | | | M12 | 7 | −0.049 (±0.122) | 50 | −0.005 (±0.046) |
| rs2283497 | 16:4066061 | 0.393 | M06 | 31 | −0.005 (±0.053) | 88 | −0.001 (±0.038) |
| | | | M12 | 27 | −0.006 (±0.058) | 80 | 0.005 (±0.049) |
| rs2531967 | 16:4052486 | 0.231 | M06 | 13 | −0.007 (±0.024) | 68 | −0.008 (±0.042) |
| | | | M12 | 12 | −0.031 (±0.086) | 57 | −0.006 (±0.053) |
| rs3730119 | 16:4057603 | 0.177 | M06 | 6 | 0.006 (±0.103) | 49 | −0.002 (±0.050) |
| | | | M12 | 6 | −0.028 (±0.087) | 47 | 0.004 (±0.052) |
| rs13337675 | 16:4077178 | 0.247 | M06 | 7 | 0.016 (±0.107) | 66 | 0.002 (±0.044) |
| | | | M12 | 8 | −0.011 (±0.115) | 62 | 0.005 (±0.042) |

TABLE 13-continued

Change from baseline in carotid intima-media thickness after 6 and 12 months of dalcetrapib treatment. 20 SNPs with P < 0.05 in dal-OUTCOMES are shown with results for the dal-PLAQUE-2 study.

| SNP | dal-PLAQUE-2 Homozygotes for major allele | | | dal-OUTCOMES | | |
|---|---|---|---|---|---|---|
| | N | Mean (±STD) mm | P value[3] | P value[4] | HR[4] | Origin[5] |
| rs1967309 | 62 | 0.006 (±0.047) | 0.114 | 2.41×10⁻⁸ | 0.651 | GWAS |
| | 60 | 0.005 (±0.042) | | | (0.560, 0.757) | |
| rs2531971 | 54 | 0.008 (±0.042) | 0.1415 | 7.74×10⁻⁸ | 0.664 | Sequenom |
| | 52 | −0.002 (±0.059) | | | (0.572, 0.771) | |
| rs2238448 | 48 | 0.011 (±0.043) | 0.009 | 8.88×10⁻⁸ | 0.671 | Sequenom |
| | 46 | 0.009 (±0.038) | | | (0.58, 0.777) | |
| rs11647778 | 48 | 0.011 (±0.043) | 0.0087 | 1.72×10⁻⁷ | 0.678 | Sequenom |
| | 47 | 0.008 (±0.040) | | | (0.586, 0.784) | |
| rs12599911 | 48 | 0.011 (±0.044) | 0.0205 | 1.72×10⁻⁷ | 0.674 | Sequenom |
| | 46 | 0.010 (±0.038) | | | (0.582, 0.782) | |
| rs12595857 | 48 | 0.011 (±0.044) | 0.0193 | 2.02×10⁻⁷ | 0.677 | GWAS |
| | 46 | 0.010 (±0.038) | | | (0.584, 0.784) | |
| rs12920508 | 62 | 0.006 (±0.047) | 0.114 | 3.18×10⁻⁷ | 0.669 | Sequenom |
| | 60 | 0.005 (±0.042) | | | (0.574, 0.781) | |
| rs2239310 | 71 | 0.004 (±0.041) | 0.6456 | 9.58×10⁻⁷ | 0.674 | GWAS |
| | 67 | 0.001 (±0.051) | | | (0.576, 0.789) | |
| rs11647828 | 56 | 0.011 (±0.041) | 0.0051 | 1.32×10⁻⁶ | 0.696 | GWAS |
| | 54 | 0.009 (±0.038) | | | (0.601, 0.806) | |
| rs8049452 | 63 | −0.008 (±0.054) | 0.0126 | 1.93×10⁻⁶ | 1.413 | GWAS |
| | 56 | −0.013 (±0.069) | | | (1.225, 1.629) | |
| rs12935810 | 70 | −0.006 (±0.053) | 0.0186 | 1.03×10⁻⁵ | 1.377 | GWAS |
| | 63 | −0.007 (±0.069) | | | (1.194, 1.587) | |
| rs8061182 | 67 | −0.009 (±0.054) | 0.0182 | 4.72×10⁻⁵ | 1.343 | GWAS |
| | 60 | −0.014 (±0.067) | | | (1.165, 1.547) | |
| rs74702385 | 142 | 0.002 (±0.048) | 0.3881 | 7.31×10⁻⁵ | 0.599 | GWAS |
| | 136 | −0.001 (±0.055) | | | (0.465, 0.772) | |
| rs17136707 | 142 | 0.002 (±0.048) | 0.3249 | 7.40×10⁻⁵ | 0.594 | GWAS |
| | 136 | −0.001 (±0.054) | | | (0.459, 0.768) | |
| rs111590482 | 142 | 0.002 (±0.048) | 0.3881 | 1.25×10⁻⁴ | 0.606 | GWAS |
| | 136 | −0.001 (±0.055) | | | (0.469, 0.783) | |
| rs4786454 | 124 | 0.004 (±0.047) | 0.0222 | 1.91×10⁻⁴ | 0.668 | GWAS |
| | 119 | 0.003 (±0.049) | | | (0.540, 0.825) | |
| rs2283497 | 72 | 0.001 (±0.050) | 0.9875 | 5.23×10⁻⁴ | 0.766 | GWAS |
| | 69 | −0.007 (±0.055) | | | (0.659, 0.891) | |
| rs2531967 | 110 | 0.005 (±0.048) | 0.0184 | 6.67×10⁻⁴ | 0.734 | GWAS |
| | 107 | 0.004 (±0.048) | | | (0.615, 0.877) | |
| rs3730119 | 136 | −0.000 (±0.040) | 0.8982 | 9.61×10⁻³ | 0.763 | GWAS |
| | 123 | −0.002 (±0.052) | | | (0.621, 0.936) | |
| rs13337675 | 118 | −0.003 (±0.041) | 0.1915 | 4.02×10⁻² | 0.834 | GWAS |
| | 106 | −0.005 (±0.053) | | | (0.702, 0.992) | |

GWAS: genome-wide association study;
HR: hazards ratio;
MAF: minor allele frequency;
OR: odds ratio;
SNP: single nucleotide polymorphism;
M06, M12: measures after 6 and 12 months of dalcetrapib treatment.
[1]Position of variants from NCBI Build GRCh37 assembly
[2]Calculated using 386 samples from the dal-Plaque-2 study population
[3]Calculated using a mixed regression model for measures of cIMT at 6 and 12 months with adjustment for baseline values
[4]Cox proportional hazards model analyzed in SAS with adjustment for gender and 5 principal components for genetic ancestry and reporting the HR for the additive genetic model for increasing copies of the minor allele.
[5]Results based on genotyped SNPs from the OMNI2.5, and from the Sequenom panel for those that had been imputed.
† HR > 1 indicate that homozygotes for the minor allele are more at risk than homozygotes for the major allele.at this SNP Statistical Analyses for Both Examples 1 and 2

Genome-wide association tests were performed using JMP Genomics software version 6.1. significant results were validated in SAS software (v. 9.3) (SAS Institute Inc., Cary, N.C., USA). The 1-degree of freedom additive genetic test was used where genotypes were coded as 0, 1 or 2, according to the count of minor alleles. In the presence of covariates, the P value for the additive genetic test is adjusted for the covariate such that $$\log\left(\frac{r}{1-r}\right) = b_0 + b_1 add + \sum_j b_j cov_j \text{ or}$$

$$\log(\text{event rate}) = b_0 + b_1 add + \sum_j b_j cov_j;$$

where r is the probability of having the event and where the null ($H_0$) under the additive genetic test is of $b_1=0$. A Cox proportional hazards regression model was used to test for gene-by-treatment interaction according to: log (event rate) ~genotype+treatment arm+genotype*treatment arm+sex+ principal components, using both treatment and placebo arm samples. The GWAS discovery models included adjustment for sex and the 5 principal components for genetic ancestry. MAF were calculated using samples from both treatment arms. Rare variants (MAF<0.05) were analyzed jointly within genes using the sequence kernel association test (SKAT) (Wu M C et al, Am J Hum Genet 2011; 89:82-93). including covariates and using a beta-weighting function with parameters $\alpha_1$ set to 1 and $\alpha_2$ set to 25. Variants positioned between two genes were analyzed as a distinct set.

For the dal-Plaque-2 population, mixed regression models for repeated measures analysis were tested in SAS software. The dal-Plaque-2 tested endpoint was the mean of IMT measures of common carotid arteries at the 6-month and the 12-month visits, using the baseline measure as covariate. Adjustment of the significance threshold for multiple testing of the 27 SNPs genotyped on the Sequenom panel was not performed, due to the highly correlated nature of the selected SNPs. As reference, the number of independent tests ($M_{eff}$) was estimated using the method of Gao et al, Genet Epidemiol 2008; 32:361-9. to $M_{eff}=8$, using the dal-Outcomes population sample.

For the linkage disequilibrium plots (FIGS. 8 and 9), Haploview (version 4.2) (Barrett J C et al. Bioinformatics 2005; 21:263-5) was used to display linkage disequilibrium $r^2$ values in a pair-wise matrix plot with a colour heat plot of D' values. Blocks of linkage disequilibrium were constructed using the confidence interval method set to [0.70, 0.98], upper confidence maximum for strong recombination 0.9 and the fraction of strong LD in informative comparisons ≥0.95.

The invention claimed is:

1. A method for increasing HDL in a subject in need thereof, the method comprising administering to the subject an effective amount of dalcetrapib, wherein the administering occurs with knowledge that the subject carries genotype rs11647778/CC or rs11647778/CG.

2. The method of claim 1, wherein the subject also carries a responsive genotype at rs1967309, rs12595857, rs2239310, rs11647828, rs8049452, rs12935810, rs74702385, rs17136707, rs8061182, rs111590482, rs4786454, rs2283497, rs2531967, rs3730119, rs2238448, or rs13337675.

3. The method of claim 1, wherein the subject carries a responsive genotype at rs1967309 or rs12595857.

4. The method of claim 1, wherein the subject carries a responsive genotype at rs1967309.

5. The method of claim 1, wherein the subject also carries one or more of the following responsive genotypes: rs12595857/GG, rs1967309/AA, rs111590482/AG, rs111590482/GG, rs11647828/GG, rs12935810/GG, rs17136707/GG, rs2239310/GG, rs2283497/AA, rs2531967/AA, rs3730119/AA, rs4786454/AA, rs74702385/GA, rs74702385/AA, rs8049452/GG, and rs8061182/AA.

6. The method of claim 1, wherein the amount of dalcetrapib is about 100 mg to about 1800 mg per day.

7. The method of claim 1, wherein the amount of dalcetrapib is about 300 mg to about 900 mg per day.

8. The method of claim 1, wherein the amount of dalcetrapib is about 600 mg per day.

9. The method of claim 1, wherein the subject has a cardiovascular disorder.

10. The method of claim 9, wherein the cardiovascular disorder is coronary heart disease, coronary artery disease, hypoalphalipoproteinemia, hyperbetalipoproteinemia, hypercholesterolemia, hyperlipidemia, atherosclerosis, hypertension, hypertriglyceridemia, hyperlipidoproteinemia, peripheral vascular disease, angina, ischemia, myocardial infarction, dyslipidemia, familial-hypercholesterolemia, cardiac ischemia, stroke, cardiovascular disease, reperfusion injury, angioplastic restenosis, or a vascular complication of diabetes, obesity, or endotoxemia.

11. The method of claim 1, wherein increasing HDL reduces the risk of a cardiovascular event in the subject.

12. The method of claim 11, wherein the cardiovascular event is coronary heart disease death, resuscitated cardiac arrest, non-fatal myocardial infarction, nonfatal ischemic stroke, unstable angina, or unanticipated coronary revascularization.

13. The method of claim 1, wherein the subject is a human.

* * * * *